US007943388B2

(12) United States Patent
Baetzold et al.

(10) Patent No.: US 7,943,388 B2
(45) Date of Patent: May 17, 2011

(54) ACOUSTIC SENSORS AND METHODS

(75) Inventors: John P. Baetzold, North St. Paul, MN (US); Karl E. Benson, St. Paul, MN (US); G. Marco Bommarito, Stillwater, MN (US); Michael P. Daniels, Inver Grove Heights, MN (US); Albert I. Everaerts, Oakdale, MN (US); Peggy-Jean P. Flanigan, Woodbury, MN (US); M. Benton Free, St. Paul, MN (US); Cary A. Kipke, Woodbury, MN (US); Brinda B. Lakshmi, Woodbury, MN (US); Charles M. Leir, Falcon Heights, MN (US); George G. I. Moore, Afton, MN (US); Lang N. Nguyen, St. Paul, MN (US); Rahul R. Shah, Woodbury, MN (US); Peter A. Stark, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1103 days.

(21) Appl. No.: 10/596,953

(22) PCT Filed: Dec. 17, 2004

(86) PCT No.: PCT/US2004/042382
§ 371 (c)(1),
(2), (4) Date: Mar. 9, 2007

(87) PCT Pub. No.: WO2005/066092
PCT Pub. Date: Jul. 21, 2005

(65) Prior Publication Data
US 2007/0190662 A1     Aug. 16, 2007

Related U.S. Application Data

(60) Provisional application No. 60/533,169, filed on Dec. 30, 2003.

(51) Int. Cl.
*G01N 33/00* (2006.01)
*G01N 31/00* (2006.01)
*G01N 9/24* (2006.01)
*G01S 15/00* (2006.01)

(52) U.S. Cl. .......................................... 436/92; 436/164
(58) Field of Classification Search .................... 436/92, 436/164
See application file for complete search history.

(56) References Cited

U.S. PATENT DOCUMENTS

| | | | |
|---|---|---|---|
| 2,995,542 A | 8/1961 | Brown |
| 3,442,815 A | 5/1969 | Rauhut et al. |
| 3,637,845 A | 1/1972 | Moore et al. |
| 3,801,533 A | 4/1974 | Tetenbaum et al. |
| 4,195,023 A | 3/1980 | Mulvey et al. |
| 4,233,029 A | 11/1980 | Columbus |
| 4,335,238 A | 6/1982 | Moore et al. |
| 4,338,237 A | 7/1982 | Sulzbach et al. |
| 4,558,142 A | 12/1985 | Holland et al. |
| 4,713,389 A | 12/1987 | Salzburg et al. |
| 4,738,708 A | 4/1988 | Borrod et al. |
| 5,076,094 A | 12/1991 | Frye et al. |
| 5,117,146 A | 5/1992 | Martin et al. |
| 5,151,110 A | 9/1992 | Bein et al. |
| 5,235,235 A | 8/1993 | Martin et al. |
| 5,238,950 A | 8/1993 | Clader et al. |
| 5,246,846 A | 9/1993 | Pittner et al. |
| 5,285,002 A | 2/1994 | Grootaert |
| 5,583,114 A | 12/1996 | Barrows et al. |
| 5,587,513 A | 12/1996 | Pohmer et al. |
| 5,674,742 A | 10/1997 | Northrup et al. |
| 5,700,612 A | 12/1997 | Kato et al. |
| 5,747,244 A | 5/1998 | Sheridan et al. |
| 5,763,283 A | 6/1998 | Cernosek et al. |
| 5,814,525 A | 9/1998 | Renschler et al. |
| 5,836,203 A | 11/1998 | Martin et al. |
| 5,874,500 A | 2/1999 | Rhee et al. |
| 5,880,552 A | 3/1999 | McGill et al. |
| 5,888,594 A | 3/1999 | David et al. |
| 5,948,166 A | 9/1999 | David et al. |
| 6,156,270 A | 12/2000 | Buechler |
| 6,232,139 B1 | 5/2001 | Casalnuovo et al. |
| 6,369,893 B1 | 4/2002 | Christel et al. |
| 6,573,338 B2 | 6/2003 | Halverson et al. |
| 6,632,872 B1 | 10/2003 | Pellerite et al. |
| 6,656,428 B1 | 12/2003 | Clark et al. |
| 7,078,172 B1 | 7/2006 | Okamura et al. |
| 7,078,517 B2 | 7/2006 | Takahashi et al. |
| 7,169,933 B2 | 1/2007 | Benson et al. |
| 7,175,876 B2 | 2/2007 | Free et al. |

(Continued)

FOREIGN PATENT DOCUMENTS

CA        2 369 720 A1      7/2003

(Continued)

OTHER PUBLICATIONS

Branch et al.; "Low-level detection of *Bacillus anthracis* stimulant using Love-wave biosensors on 36°YXLiTaO3;" *Biosensors and Bioelectronics*; 19 (2004) pp. 849-859.
David et al.; "Plasma Deposition and Etching of Diamond-Like Carbon Films;" *AIChE Journal*; Mar. 1991, vol. 37, No. 3 pp. 367-376.
Grate et al.; "Acoustic Wave Sensors;" vol. 2, pp. 38-83, 1996 (XP-002334970).
Tseng et al., J.Org. Chem., vol. 44, No. 23, 1979, pp. 4113-4116 (XP-002331678).

(Continued)

*Primary Examiner* — Susannah Chung
*Assistant Examiner* — Samantha L Shterengarts
(74) *Attorney, Agent, or Firm* — X. Christina Huang

(57) ABSTRACT

Acoustic sensors, preferably surface acoustic wave sensors, and more preferably shear horizontal surface acoustic wave sensors that include soluble mixed with oligomers and/or polymers formed from such monomers), or multifunctional compounds, for example, that can function as either waveguide materials, immobilization materials for secondary capture agents (e.g., antibodies), or both.

27 Claims, 3 Drawing Sheets

U.S. PATENT DOCUMENTS

| | | | |
|---|---|---|---|
| 7,179,923 | B2 | 2/2007 | Benson et al. |
| 7,211,445 | B2 | 5/2007 | Pozsgay |
| 2003/0010474 | A1 | 1/2003 | Araki et al. |
| 2003/0170881 | A1 | 9/2003 | Davis et al. |
| 2005/0106709 | A1 | 5/2005 | Benson et al. |
| 2005/0227076 | A1 | 10/2005 | Benson et al. |
| 2007/0068256 | A1 | 3/2007 | Xu et al. |

FOREIGN PATENT DOCUMENTS

| | | |
|---|---|---|
| EP | 0 010 844 A1 | 5/1980 |
| EP | 0 177 740 | 5/1986 |
| EP | 0 446 047 A1 | 9/1992 |
| EP | 0 535 236 B1 | 4/1993 |
| EP | 0 657 737 A2 | 6/1995 |
| EP | 0 814 381 B1 | 12/1997 |
| JP | 53 063375 | 6/1978 |
| JP | 03055544 | 7/1989 |
| JP | 1-114861 | 8/1989 |
| JP | 5-188663 | 7/1993 |
| JP | 9-054463 | 2/1997 |
| JP | 1-1109630 | 4/1999 |
| JP | 2003-322860 | 11/2003 |
| WO | WO 00/16903 | 3/2000 |
| WO | WO 01/11370 | 2/2001 |
| WO | WO 01/23892 A1 | 4/2001 |
| WO | WO 01/66820 A1 | 9/2001 |
| WO | WO 01/67086 | 9/2001 |
| WO | WO 02/088296 A1 | 11/2002 |
| WO | WO 02/094890 | 11/2002 |
| WO | WO 02/095940 A1 | 11/2002 |
| WO | WO 03/068712 A2 | 8/2003 |
| WO | WO 03/084982 A2 | 10/2003 |
| WO | WO 03/093785 A2 | 11/2003 |
| WO | WO 2004/067732 A2 | 8/2004 |
| WO | WO 2005/075973 A2 | 8/2005 |

OTHER PUBLICATIONS

Adams et al., Journal of American Chemical Society, 78, 3825-3828, 1956, (XP-002331677).

Mustafa et al, Journal of American Chemical Society, 79, 1945-1949, 1957, (XP-002331676).

Guo et al., Journal of Fluorine Chemistry, 52, 29-36, 1991, (XP-002331675).

Yoshio et al., Database accession No. 1979: 492034 (XP-002331680).

Toshiaki et al, Database accession No. 1995: 708887 (XP-002331681).

Satoshi et al., Database accession No. 2004: 1125476 (XP-00231679).

Bozhinov et al., "Synthesis of new flame retardable sulfonamides in phase-transfer catalysis conditions", *Chemical Abstracts*, 117:235734, 1992.

Chiyomaru et al., "Fungicides for agricultural use", Database accession No. 1973: 144282 XP-002331203.

Chiyomaru et al., "2-Substituted 1,2-benzoisothiazolin-3-one 1,1-dioxides", Database accession No. 1972: 77 :164667 XP-002331204.

Chiyomaru et al., 2-Substitued 1,2-benzoisothiazolin-3-one 1-dioxide, 1975, *Chemical Abstracts* 82:140119.

Hashimoto et al., "Preparation of N-(phenylsulfenyl)-2-chloroacetamides as herbicides", 1991, *CAS*: 115:207678.

Iwakura et al., "Benzenesulfonamide derivatives", 1980, *CAS*: 92:41570.

Kato, et al., 1973, "Syntheses of imide derivatives", *Chemical Abstracts* 78:124224.

Kato et al., "Electrophotographic material for lithographic plate preparation" *Chemical Abstracts*, 120:65816, 1994.

Kharasch et al., "Reactions of atoms and free radicals in solution." *Chemical Abstracts*, 47:1656c-1, 1953.

Lahiri, J., et al., "Patterning Ligands on Reactive SAMs by Microcontact Printing", *Langmuir*, 1999, 15, 2055-2060.

Luheshi et al., "Heterocycles by Intramolecular Aza-Wittig Reactions of Iminophosphoranes Obtained from 2-Azidobenzoyl- and 2-Azidobenzylidene Derivatives", 1990, *Tetrahedron Letters*, 31(45), pp. 6561-6564.

Lukovits, "Decomposition of the Wiener Topological Index. Application to Drug-Receptor Interactions", *Journal of the Chemical Society Perkins Transactions II*, 1988, pp. 1667-1671.

Mandel'baum, et al., "Synthesis of derivatives of S-[1-(N-methyl-N-methylsulfonyl)carbamoylethyl]thio-and -dithiophosphoric acid" 1975, *Chemical Abstracts*: 82:57814.

Mine, et al., 1972, "2-Carbamoyl-1, 2-benzisothiazolin-3-one 1,1-dioxides", *Chemical Abstracts*: 76:14533.

Naumov et al., "Spectra-structure correlations in solid metal saccharinates" 2002, *Chemical Abstracts*: 137:83888.

Niculescu, M., et al., "Redox Hydrogel-Based Amperometric Bienzyme Electrodes for Fish Freshness Monitoring", *Anal. Chem.* 2000, 72, 1591-1597.

Schrader's, "Esters of mono- or dithiophosphoric, phosphonic, and phosphinic acids", 1964, CAS: 60:3301.

Shah, R.R., et al., "Using Liquid Crystals to Image Reactants and Products of Acid-Base Reactions on Surfaces with Micrometer Resolution", *J. Am. Chem. Soc.*, 1999, 121, 11300-11310.

Shah, R.R., et al., "Principles for Measurement of Chemical Exposure Based on Recognition-Driven Anchoring Transitions in Liquid Crystals", *Science*, 2001, 293, 1296.

Wagner, P., et al., "Covalent Immobilization of Native Biomolecules onto Au(111) via N-Hydroxysuccinimide Ester Functionalized Self-Assembled Monolayers for Scanning Probe Microscopy", *Biophysical. Journal*, 1996, vol. 70, 2052-2066.

Wang, J., et al. "Ultrathin Porous Carbon Films as Amperometric Transducers for Biocatalytic Sensors", *Anal. Chem.* 1994, 66, 1988-1992.

Webb, et al., "Appraisal of ethylene production as a test for defoliants", *Chemical Abstracts*, 83:189238, 1975.

Yamahara et al., Chemical Abstracts, 133:357243, 2000.

ACOUSTIC SENSORS AND METHODS

CROSS-REFERENCE TO RELATED APPLICATIONS

This application claims priority to U.S. Provisional Patent Application Ser. No. 60/533,169, filed on Dec. 30, 2003; U.S. application Ser. No. 10/714,053, filed Nov. 14, 2003; U.S. application Ser. No. 10/987,075, filed Nov. 12, 2004; U.S. application Ser. No. 10/713,174, filed Nov. 14, 2003 and U.S. Ser. No. 10/987,522, filed Nov. 12, 2004 which are incorporated herein by reference.

GOVERNMENT RIGHTS

The U.S. Government may have certain rights to this invention under the terms of Contract Number DAAD13-03-C-0047 granted by the Department of Defense.

BACKGROUND

Acoustic wave sensors are so named because their detection mechanism is a mechanical, or acoustic, wave. As the acoustic wave propagates through or on the surface of the material, any changes to the characteristics of the propagation path affect the velocity and/or amplitude of the wave. Changes in velocity can be monitored by measuring the frequency or phase characteristics of the sensor and can then be correlated to the corresponding physical quantity being measured.

Virtually all acoustic wave devices and sensors use a piezoelectric material to generate the acoustic wave. Piezoelectricity refers to the production of electrical charges by the imposition of mechanical stress. The phenomenon is reciprocal. Applying an appropriate electrical field to a piezoelectric material creates a mechanical stress. Piezoelectric acoustic wave sensors apply an oscillating electric field to create a mechanical wave, which propagates through the substrate and is then converted back to an electric field for measurement. Depending on the type of acoustic wave sensor, different metal electrode configurations are used to establish an electric field driving the piezoelectric material. For example, when the acoustic wave is a transverse bulk wave, such as in a thickness shear mode (TSM) sensor, the electrodes are planar and they sandwich the piezoelectric material. In surface launched acoustic wave sensors the electrodes are typically interdigitated (IDT) electrode pairs, fabricated by photolithography directly onto the piezoelectric substrate.

Acoustic wave devices are described by the mode of wave propagation through or on a piezoelectric substrate. A wave propagating through the substrate is called a bulk wave. The most commonly used bulk acoustic wave device is the thickness shear mode (TSM) resonator.

When the acoustic wave propagates on the surface of the substrate, it is known as a surface wave. The surface acoustic wave sensor (SAW) and the shear-horizontal surface acoustic wave (SH-SAW) sensor are the most widely used surface wave devices. One of the important features of a SH-SAW sensor is that it allows for sensing in liquids. This is because, since the shear horizontal wave is confined to the surface of the sensor, it does not dissipate energy into liquids contacting that surface, allowing liquid operation without damping.

Of all the known acoustic sensors for liquid sensing, the Love wave sensor, a special class of the SH-SAW, has the highest sensitivity. To make a Love wave sensor, a waveguide coating is placed on a SH-SAW device such that the energy of the shear horizontal waves is confined and focused in that coating. To form a complete conventional sensor, a biorecognition coating (e.g., one including capture agents) is then placed on the waveguide coating. An immobilization chemistry layer is interposed between the biorecognition and waveguide coatings, to act as a tie layer between the two. Binding of a bio-analyte to the biorecognition coating will change the propagation characteristics of the surface acoustic wave and measuring these changes can be used to quantitatively detect the existence of the analyte.

Waveguide materials are important in the propagation of acoustic energy, particularly with respect to the construction of delay-line devices. Just as with optical waveguides, acoustic energy is propagated in the direction of the guide. Waveguides are layers with dimensions of the order of the acoustic wavelength, and as mentioned above, device structures in which thin film waveguides are used to guide acoustic waves are often called Love wave devices. In Love wave devices, the acoustic energy is genuinely confined to the surface of the device in a pure shear horizontal mode, leading to greater analytical sensitivity. Conventional waveguides include a wide range of materials including both inorganic and organic materials.

Although inorganic materials have been successfully used as waveguides in Love wave devices, organic polymeric materials are generally more advantageous because the rheology of such materials can be tailored for low acoustic losses, high stability of the waveguide under a liquid, and provide superior electrical insulation to the interdigitated electrodes (IDTs) of the device when used in a liquid. Furthermore, a wide variety of coating methods can be used to apply a polymeric waveguide in a device construction. Organic polymeric materials are also easy to (photo)image, so patterned coatings can be readily obtained.

Similarly, organic immobilization chemistries (which form a bridge between the waveguide and the biorecognition coating) are desirable because the rheology of such materials can be tailored for low acoustic losses, high stability of the immobilization chemistry layer under a liquid, especially when the thickness of this layer becomes appreciable when compared to the acoustic wavelength. Organic materials can also provide a superior adhesion bridge between the waveguide and the biorecognition coating. Furthermore, a wide variety of coating methods can be used to apply a polymeric immobilization layer in a device construction.

There is a continuing need for organic materials that can be used as the waveguide and/or immobilization chemistry in acoustic sensors.

SUMMARY

The present invention provides acoustic sensors, preferably surface acoustic wave sensors, and more preferably shear horizontal surface acoustic wave sensors. Typically, such sensors include, for example, functionalized soluble polymers, functionalized monomers (or mixtures of monomers, oligomers, and polymers formed from such monomers), or multifunctional compounds that can function as either waveguide materials, immobilization materials for secondary capture agents (e.g., antibodies), or both. For example, certain materials of the present invention (e.g., functionalized soluble polymers) can function as waveguide materials (with different immobilization materials), immobilization materials (with different waveguide materials), or they can function as both. Additionally, certain materials of the present invention (e.g., functionalized soluble polymers) can perform the function of the waveguide and capture material. That is, certain materials (preferably, functionalized soluble polymers) of the present invention function as the waveguide material and capture material (typically, for non-specific capture) all in one.

Such functionalized soluble polymers are preferred and include two or more pendant groups independently selected from the group consisting of the following functional groups (I), (II), (II), and (IV):

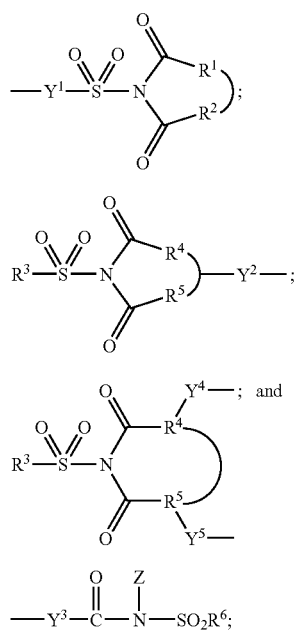

wherein $R^1$, $R^2$, $R^3$, $R^4$, $R^5$, $R^6$, $Y^1$, $Y^2$, $Y^3$, $Y^4$, $Y^5$, and Z are defined herein.

Suitable functionalized monomers (which can be in combination with oligomers and/or polymers formed from such monomers) include functional groups (I), (II), and (IV). These monomers can be suitable for use in the waveguide layer, the immobilization layer, or both (with or without secondary capture agents (e.g., antibodies)).

Suitable multifunctional compounds include functional groups (I), (II), and (IV). These compounds can be suitable for use in the waveguide layer, the immobilization layer, or both (with or without secondary capture agents (e.g., antibodies)).

Another class of compounds suitable for use in the acoustic sensors of the present invention (typically, in the immobilization layer) includes compounds with one or two functional groups represented by Formulas I, II, or IV, wherein each Y group ($Y^1$, $Y^2$, $Y^3$) is bonded to a substrate reactive-functional group.

Other materials for use in acoustic sensors of the present invention (typically, in the waveguide layer) includes: a polymer derived from one or more different monomers, wherein at least one is an (meth)acrylate monomer, wherein the polymer does not include functional groups represented by Formulas I, II, III, and IV; a polymer derived from N-vinylcarbazole and optionally other ethylenically unsaturated monomers; a polyepoxide (preferably, a polymer of an aromatic or cycloaliphatic diepoxide); and a vinylidene fluoride ($VF_2$)-containing fluoropolymer.

Various combinations (including mixtures) of such materials can be used in an acoustic sensor.

Other materials suitable for use in acoustic sensors of the present invention (typically, in the waveguide layer), typically in combination with one of the materials described above, include a polymer derived from one or more (meth)acrylate monomers, a styrene-containing polymer, a polymer derived from N-vinylcarbazole and optionally other ethylenically unsaturated monomers, a polyimide, a $VF_2$-containing fluoropolymer, or combinations thereof.

In one embodiment, the present invention provides an acoustic sensor comprising a surface that includes:

(a) a soluble polymer having two or more pendant groups independently selected from the group consisting of functional groups having the following formulas:

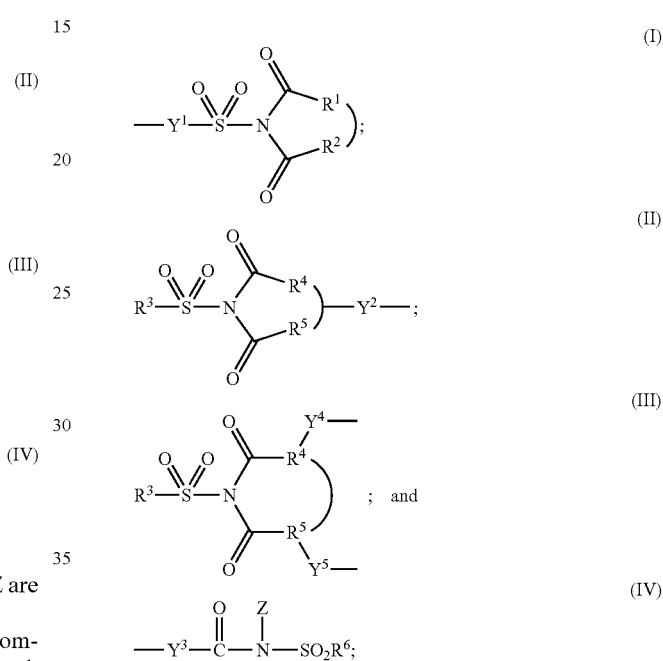

wherein:
$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

$R^3$ is an alkyl, aryl, aralkyl, or —$NR^aR^b$ wherein $R^a$ and $R^b$ are each an alkyl group or taken together with the nitrogen atom to which they are attached form a four to eight membered heterocyclic group;

$R^4$ and $R^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

$R^6$ is an alkyl, fluoroalkyl, chloroalkyl, aryl, —$NR^cR^d$ wherein $R^c$ and $R^d$ are each an alkyl group or taken together with the nitrogen atom to which they are attached form a four to eight membered cyclic group, or $R^6$ taken together with $R^e$ and the groups to which they are attached form the four to eight membered heterocyclic or heterobicyclic group that can be fused to the optional aromatic group, optional saturated or unsaturated cyclic group, or optional saturated or unsaturated bicyclic group;

Z is an alkyl, aryl, or —(CO)R$^e$ wherein R$^e$ together with R$^6$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

Y$^1$, Y$^2$, and Y$^3$ are each independently a single bond or a divalent group selected from the group consisting of an alkylene, heteroalkylene, arylene, carbonyl, carbonyloxy, carbonylimino, oxy, thio, —NR$^f$— where R$^f$ is hydrogen or alkyl, and combinations thereof; and Y$^4$ and Y$^5$ are each a bond; or (b) monomers of the formula:

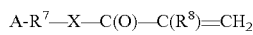
A-R$^7$—X—C(O)—C(R$^8$)=CH$_2$ wherein:
A is selected from the group consisting of functional groups having the formulas (I), (II), and (IV);
X is —N(R$^9$)— or —O—;
R$^7$ is a divalent group selected from the group consisting of alkylene, heteroalkylene, arylene, heteroarylene, and combinations thereof, wherein the alkylene and heteroalkylene optionally include one or more carbonyls;
R$^8$ is hydrogen or methyl; and
R$^9$ is hydrogen or a C$_{1-6}$ alkyl group; or (c) a multifunctional compound of the formula:

(A'-)$_y$-Q wherein:
each A' is independently selected from the group consisting of functional groups having the formulas (I), (II), and (IV);
Q is a single bond or an y-valent atom or group; and
y is an integer of 2 to 10;
with the proviso that Q, Y$^1$, Y$^2$, and Y$^3$ are free of disulfide groups; or (d) a compound having one or two functional groups represented by Formulas III, or IV, wherein each Y group (Y$^1$, Y$^2$, Y$^3$) is bonded to a substrate reactive-functional group independently selected from the group consisting of a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, ethylenically unsaturated group, and combinations thereof; or (e) a polymer derived from one or more different monomers, wherein at least one monomer is a (meth)acrylate monomer, and wherein the polymer does not include functional groups having formulas I, II, III, or IV; or (f) a polymer derived from N-vinylcarbazole and optionally other ethylenically unsaturated monomers; or (g) a VF$_2$-containing fluoropolymer;

(h) a polyepoxide; or
combinations thereof.

In another embodiment, the present invention provides an acoustic sensor that includes a soluble polymer having two or more pendant groups independently selected from the group consisting of functional groups having the following formulas:

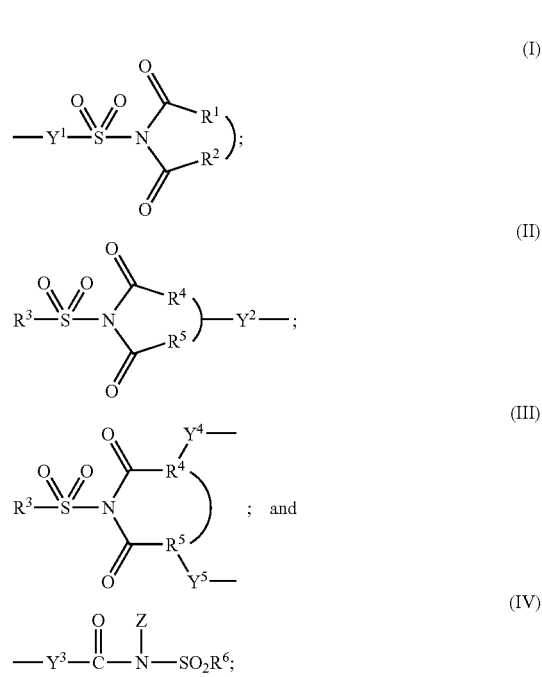

wherein:
R$^1$ and R$^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

R$^3$ is an alkyl, aryl, aralkyl, or —NR$^a$R$^b$ wherein R$^a$ and R$^b$ are each an alkyl group or taken together with the nitrogen atom to which they are attached form a four to eight membered heterocyclic group;

R$^4$ and R$^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

R$^6$ is an alkyl, fluoroalkyl, chloroalkyl, aryl, —NR$^c$R$^d$ wherein R$^c$ and R$^d$ are each an alkyl group or taken together with the nitrogen atom to which they are attached form a four to eight membered cyclic group, or R$^6$ taken together with R$^e$ and the groups to which they are attached form the four to eight membered heterocyclic or heterobicyclic group that can be fused to the optional aromatic group, optional saturated or unsaturated cyclic group, or optional saturated or unsaturated bicyclic group;

Z is an alkyl, aryl, or —(CO)R$^e$ wherein R$^e$ together with R$^6$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

Y$^1$, Y$^2$, and Y$^3$ are each independently a single bond or a divalent group selected from the group consisting of an alkylene, heteroalkylene, arylene, carbonyl, carbonyloxy, carbonylimino, oxy, thio, —NR$^f$— where R$^f$ is hydrogen or alkyl, and combinations thereof; and Y$^4$ and Y$^5$ are each a bond.

In another embodiment, the present invention provides a method of coating an acoustic sensor. The method includes applying a soluble polymer (as described herein) to a surface of the acoustic sensor using a non-contact deposition technique.

Definitions

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "alkyl" refers to a monovalent radical of an alkane and includes groups that are linear, branched, cyclic, or combinations thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

As used herein, the term "alkylene" refers to a divalent radical of an alkane. The alkylene can be straight-chained, branched, cyclic, or combinations thereof. The alkylene typically has 1 to 200 carbon atoms. In some embodiments, the alkylene contains 1 to 100, 1 to 80, 1 to 50, 1 to 30, 1 to 20, 1 to 10, 1 to 6, or 1 to 4 carbon atoms. The radical centers of the alkylene can be on the same carbon atom (i.e., an alkylidene) or on different carbon atoms.

As used herein, the term "aralkyl" refers to a monovalent radical of the compound R—Ar where Ar is an aromatic carbocyclic group and R is an alkyl group.

As used herein, the term "aralkylene" refers to a divalent radical of formula —R—Ar— where Ar is an arylene group and R is an alkylene group.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "arylene" refers to a divalent radical of a carbocyclic aromatic compound having one to five rings that are connected, fused, or combinations thereof. In some embodiments, the arylene group has up to 5 rings, up to 4 rings, up to 3 rings, up to 2 rings, or one aromatic ring. For example, the arylene group can be phenylene.

The above aryl and arylenes can optionally contain substitutents such as lower alkyl, halo, and alkoxy.

As used herein, the term "carbonyl" refers to a divalent group of formula CO)—.

As used herein, the term "carbonylimino" refers to a divalent group of formula —(CO)NR$^a$— where R$^a$ is hydrogen, alkyl, or aryl.

As used herein, the term "carbonyloxy" refers to a divalent group of formula —(CO)O—.

As used herein, the term "chloroalkyl" refers to an alkyl having at least one hydrogen atom replaced with a chlorine atom.

As used herein, the term "disulfide" refers to a divalent group of formula —S—S—.

As used herein, the term "ethylenically unsaturated" refers to a monovalent group having a carbon-carbon double bond of formula —CY=CH$_2$ where Y is hydrogen, alkyl, or aryl.

As used herein, the term "fluoroalkyl" refers to an alkyl having at least one hydrogen atom replaced with a fluorine atom. Some fluoroalkyl groups are perfluoroalkyl groups.

As used herein, the term "heteroalkylene" refers to a divalent alkylene having one or more carbon atoms replaced with a sulfur, oxygen, or NR$^d$ where R$^d$ is hydrogen or alkyl. The heteroalkylene can be linear, branched, cyclic, or combinations thereof and can include up to 400 carbon atoms and up to 30 heteroatoms. In some embodiments, the heteroalkylene includes up to 300 carbon atoms, up to 200 carbon atoms, up to 100 carbon atoms, up to 50 carbon atoms, up to 30 carbon atoms, up to 20 carbon atoms, or up to 10 carbon atoms.

As used herein, the term "heteroarylene" refers to a divalent arylene having one or more carbon atoms replaced with a sulfur, oxygen, or NR$^f$ where R$^f$ is hydrogen or alkyl.

As used herein, the term "oxy" refers to a divalent group of formula —O—.

As used herein, the term "perfluoroalkyl" refers to an alkyl group in which all of the hydrogen atoms are replaced with fluorine atoms.

As used herein, the term "thio" refers to a group of formula —.

As used herein, the term "room temperature" refers to a temperature of about 20° C. to about 25° C. or about 22° C. to about 25° C.

As used herein, a curve connecting two groups in a formula indicates that the two groups together form part of a cyclic structure.

For any of the compounds presented herein, each one of the following variables (e.g., $R^1$, $R^2$, $Y^1$, $Y^2$, Z, A, and so on) in any of its embodiments can be combined with any one or more of the other variables in any of their embodiments as would be understood by one of skill in the art. Each of the resulting combinations of variables is an embodiment of the present invention.

When a group (or substituent or variable) is present more than once in a compound or polymer described herein, each group (or substituent or variable) is independently selected, whether explicitly stated or not. For example, for the soluble polymers of the present invention each pendant group is independently selected. Furthermore, when each pendant group contains one or more L groups, as defined below, then each L group is also independently selected.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention employs an acoustic sensor, and more specifically, an acoustic mechanical biosensor, that detects a change in at least one physical property and produces a signal in response to the detectable change. Preferably, the acoustic mechanical biosensor employed herein is a surface acoustic wave (SAW) biosensor. In these devices an acoustic wave is generated from an interdigital transducer (IDT) on a piezoelectric substrate either as a surface acoustic wave or as a bulk acoustic wave. A second IDT may convert the acoustic wave back to an electric signal for measurement. This is referred to as a delay line. Alternatively the device may operate as a resonator. The space between the two IDTs can be modified with a coating that may include reactive molecules for chemical or biosensing applications.

Figure 1:
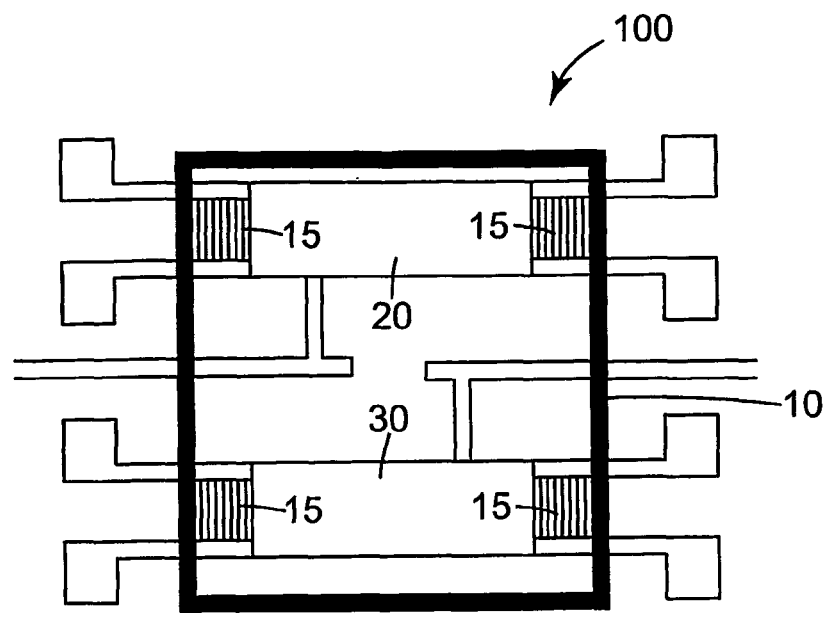
FIG. 1 is a representation of an acoustic sensor of the present invention.

With reference to FIG. 1, in some embodiments the acoustic mechanical biosensor surface 100 between the IDTs 15 preferably comprises two delay lines. A first channel, i.e. the "active" channel 20 is provided for receipt of the test sample. The second channel, i.e. the "reference" channel 30 is provided as the baseline or control. Accordingly, the change in physical property is the difference between the active channel and the reference channel. When necessary, an acoustic waveguide 10 (only the boundaries of which are depicted in FIG. 1) typically covers the area between the IDTs as well as the IDTs themselves. The data may be transformed with mathematical algorithms in order to improve the sensitivity.

Piezoelectric-based SAW biosensors typically operate on the basis of their ability to detect minute changes in mass or viscosity. As described in U.S. Pat. No. 5,814,525, the class of piezoelectric-based acoustic mechanical biosensors can be further subdivided into surface acoustic wave (SAW), acoustic plate mode (APM), or quartz crystal microbalance (QCM) devices depending on their mode of detection of mass changes.

In some embodiments, the acoustic mechanical biosensor includes a secondary capture agent or reactant (e.g., antibody) that attaches the biomolecule of interest to the surface of the piezoelectric acoustic mechanical biosensor. In other embodiments, the acoustic mechanical biosensor detects a physical change in a liquid (e.g. aqueous solution) such as a change in viscosity. The propagation velocity of the surface wave is a sensitive probe capable of detecting changes such as mass, elasticity, viscoelasticity, conductivity and dielectric constant. Thus, changes in any of these properties results in a detectable change in the surface acoustic wave. That is, when a substance comes in contacts with, absorbs, or is otherwise caused to adhere to the surface coating of a SAW device, a corresponding response is produced.

APM can also be operated with the device in contact with a liquid. Similarly, an alternating voltage applied to the two opposite electrodes on a QCM (typically AT-cut quartz) device induces a thickness shear wave mode whose resonance frequency changes in proportion to mass changes in a coating material.

The direction of the acoustic wave propagation (e.g., in the plane parallel to the waveguide or perpendicular to the plane of the waveguide) is determined by the crystal-cut of the piezoelectric material from which the acoustic mechanical biosensor is constructed. SAW biosensors that have the majority of the acoustic wave propagating in and out of the plane (i.e., Rayleigh wave, most Lamb-waves) are typically not employed in liquid sensing applications since there is too much acoustic damping from the liquid contact with the surface.

For liquid sample mediums, a shear horizontal surface acoustic wave biosensor (SH-SAW) is preferably constructed from a piezoelectric material with a crystal-cut and orientation that allows the wave propagation to be rotated to a shear horizontal mode, i.e., in plane of the biosensor waveguide), resulting in reduced acoustic damping loss to the liquid in contact with the biosensor surface. Shear horizontal acoustic waves include, e.g., acoustic plate modes (APM), surface skimming bulk waves (SSBW), Love-waves, leaky acoustic waves (LSAW), and Bleustein-Gulyaev (BG) waves.

In particular, Love wave sensors consist of a substrate supporting a SH wave mode such as SSBW of ST quartz or the leaky wave of 36°YXLiTaO$_3$. These modes are converted into a Love-wave mode by application of thin acoustic guiding layer or waveguide. These waves are frequency dependent and can be generated provided that the shear wave velocity of the waveguide layer is lower than that of the piezoelectric substrate. SiO$_2$ has been used as an acoustic waveguide layer on quartz. Other thermoplastic and crosslinked polymeric waveguide materials such as polymethylmethacrylate, phenol-formaldehyde resin (e.g., trade designation NOVALAC), polyimide and polystyrene, have also been employed.

Alternatively QCM devices can also be used with liquid sample mediums, although with these devices the acoustic wave will be severely damped by the liquid medium, leading to a generally less sensitive device.

Biosensors employing acoustic mechanical means and components of such biosensors are known. See, for example, U.S. Pat. Nos. 5,076,094; 5,117,146; 5,235,235; 5,151,110; 5,763,283; 5,814,525; 5,836,203; 6,232,139. SH-SAW devices can be obtained from various manufacturers such as Sandia National Laboratories, Albuquerque, N. Mex. Certain SH-SAW biosensors are also described in "Low-level detection of a *Bacillus anthracis* stimulant using Love-wave biosensors of 36°YXLiTaO$_3$," Biosensors and Bioelectronics, 19, 849-859 (2004). SAW biosensors, as well as methods of detecting biological agents, are also described in U.S. Patent Application Ser. No. 60/533,169, filed Dec. 30, 2003 and PCT Publication No. WO 2005/075973.

In some embodiments, the surface of the biosensor includes a secondary capture agent or reactant (e.g., antibody) overlying the waveguide layer. In this embodiment, the biosensor typically detects a change in viscosity and/or mass bound by the secondary capture agent or reactant. For this embodiment, the biosensor preferably includes an immobilization layer (overlying the waveguide layer) and optional tie layer(s).

An immobilization layer can be provided for the purpose of binding the secondary capture agent or reactant (e.g., antibody) to the surface.

Another class of compound suitable for use in the acoustic sensors of the present invention (typically, in the immobilization layer) include compounds with one or two functional groups represented by Formulas I, II, or IV, wherein each Y group ($Y^1$, $Y^2$, $Y^3$) is bonded to a substrate reactive-functional group independently selected from the group consisting of a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, ethylenically unsaturated group, and combinations thereof. An exemplary immobilization layer includes N-(11-trichlorosilylundecenoyl)saccharin. Such compounds are disclosed in Applicants' Assignee's U.S. Pat. Nos. 7,361,767, 7,169,933, 7,423,155 and 7,179,923.

Other examples of a material suitable for the immobilization layer (referred to herein as "immobilization chemistries") include, for example, a soluble polymer having two or more pendant groups having the formulas (I), (II), (III), or (IV); a multifunctional compound of the formula $(A'\text{-})_y\text{-}Q$ wherein each $A'$ is independently selected from the group consisting of functional groups having the (I), (II), and (IV), Q is a single bond or an y-valent atom or group, and y is an integer of 2 to 10; with the proviso that $Q, Y^1, Y^2$, and $Y^3$ are free of disulfide groups; or a monomer (optionally in combination with oligomers or polymers formed from such monomers) of the formula $A\text{-}R^7\text{---}X\text{---}C(O)\text{---}C(R^8)\text{=}CH_2$ wherein A is selected from the group consisting of functional groups having the following formulas (I), (II), and (IV), X is $\text{---}N(R^9)\text{---}$ or $\text{---}O\text{---}$, $R^7$ is a divalent group selected from the group consisting of alkylene, heteroalkylene, arylene, heteroarylene, and combinations thereof, wherein the alkylene and heteroalkylene optionally include one or more carbonyls, $R^8$ is hydrogen or methyl, and $R^9$ is hydrogen or a $C_{1-6}$ alkyl group.

Preferably, the immobilization layer includes the soluble polymer having two or more pendant groups independently selected from the group consisting of functional groups (I), (II), (III), and (IV).

Alternatively, these functional groups can function themselves as the capture material. In such embodiments, a secondary capture agent (e.g., antibody) is not used and the functionalized polymers, monomers, or multifunctional compounds described herein perform the function of capturing the biomolecules of interest, although typically not as specifically as when secondary capture agents are used.

Thus, in certain embodiments of the present invention, the biosensor is substantially free of secondary capture agents (i.e., reactants such as antibodies). For example, if the immobilization layer is formed from a soluble polymer having two or more pendant groups having the formulas (I), (II), (III), or (IV) described herein, then these functional groups can function as the capture material.

In some embodiments of the present invention, the functionalized immobilization chemistry (particularly the soluble polymers described herein) can also function as the waveguide. In such embodiments, the acoustic mechanical biosensor can include only the waveguide layer (which functions as the capture material), or secondary capture agents can be attached to this material (in which case, the waveguide would be an immobilizing waveguide).

In some embodiments of the present invention, the functionalized immobilization layer (particularly the soluble polymers described herein) can also function as the waveguide. In such embodiments, the acoustic mechanical biosensor can include only the waveguide layer (which functions as the capture material), or secondary capture agents can be attached to this material (in which case, the waveguide would be an immobilizing waveguide).

In another embodiment, the waveguide material and the immobilization layer are applied in as separate layers, with the immobilization layer overlying the waveguide material. In order to improve the adhesion between the waveguide and the immobilization layer, one can incorporate latent reactive groups in the waveguide material, the immobilization layer, or both. After coating and drying, these latent reactive groups can be triggered to enhance adhesion at the interface between the two layers. An example of such a latent reactive group is 4-acryloyloxy benzophenone. This group can be activated by exposure to high intensity UV light (such as from a Fusion D-bulb or medium pressure mercury lamp) resulting in hydrogen abstraction and covalent bond formation be the reactive group and the surrounding polymer.

Alternatively, one can also use adhesion promoters. Adhesion promoters can be subdivided into compatibilizers and coupling agents. Compatibilizers increase the compatibility of two immiscible polymers, whereas coupling agents increase the adhesion between two polymer layers. Furthermore, compatibilizers and coupling agents can be reactive or non-reactive. Compatibilizers work on the principle of reducing the interfacial energy between two polymers, thus increasing adhesion by improving solubility across the polymer-polymer interface. Compatibilizers generally fall into three categories: non-reactive block copolymers which increase adhesion by providing a solubility bridge across the interface between polymers, reactive functional copolymers which increase adhesion by forming in-situ a block copolymer across the interface, and non-reactive polar copolymers which increase adhesion by providing polar interactions across the polymer-polymer interface. Coupling agents are typically multifunctional small molecules capable of forming covalent bonds across a polymer-polymer interface with the functional groups available in each polymer layer. The most common coupling agents are based on silanes. Compatibilizers are typically blended into one of the polymer layers. In some cases it may also be possible to coat a compatibilizer on the polymeric adherend. Coupling agents can also be blended into a polymer but they can also be coated on the adherend surface in an appropriate solvent carrier. Alternatively, the coupling agents may also be copolymerized with one or both of the materials of the waveguide and immobilization layers.

Other suitable adhesion promoters include diamond-like glass as described in International Publication No. WO 01/66820 A1, and the self-assembling monolayers described in U.S. Pat. No. 6,632,872. Other adhesion promoters can also be used such as tie layers that include, for example, gold.

Diamond-like glass is particularly useful with N-(11-trichlorosilylundecenoyl)saccharin, or other such chemistries that are used in immobilization layers, for example. The diamond-like glass is an amorphous material that includes carbon, silicon, and one or more elements selected from hydrogen, oxygen, fluorine, sulfur, titanium, or copper. Some diamond-like glass materials are formed from a tetramethylene silane precursor using a plasma process. A hydrophobic material can be produced that is further treated in an oxygen plasma to control the silanol concentration on the surface.

Diamond-like glass can be in the form of a thin film or in the form of a coating on another layer or material in the substrate. In some applications, the diamond-like glass can be in the form of a thin film having at least 30 weight percent carbon, at least 25 weight percent silicon, and up to 45 weight percent oxygen. Such films can be flexible and transparent. In some multilayer substrates, the diamond like glass is deposited on a layer of diamond-like carbon. The diamond-like carbon can, in some embodiments, function as a second tie layer or primer layer between a polymeric layer and a layer of diamond-like glass in a multilayer substrate. Diamond-like carbon films can be prepared, for example, from acetylene in a plasma reactor. Other methods of preparing such films are described U.S. Pat. Nos. 5,888,594 and 5,948,166, as well as in the article M. David et al., AIChE Journal, 37 (3), 367-376 (March 1991).

Thus, in some embodiments, the sensors of the present invention include a waveguide layer and an immobilization overlayer for secondary capture agents (e.g., antibodies), wherein either the waveguide layer or the overlying immobilization layer include soluble polymers, monomers (which can be in combination with oligomers and/or polymers formed from such monomers), or multifunctional compounds. For example, such materials can function as waveguide materials (with different immobilization materials), immobilization materials (with different waveguide materials), or they can function as both. Additionally, such materials can also function as the waveguide material, immobilizing material, and capture material (typically, for nonspecific capture) all in one. Such materials are described in more detail below. Preferred such materials are the soluble polymers described in more detail below.

The materials described herein are advantageous because they can provide low acoustic losses through the material, superior electrical insulating properties, robustness and stability in water, workability from a processing point of view, robust adhesion between the waveguide and immobilization chemistry layers, and can present a surface chemistry capable of chemically bonding a biorecognition coating, which remains biologically active after it is bonded.

Other waveguide materials for use in acoustic sensors of the present invention include a polyepoxide (preferably, a polymer of an aromatic or cycloaliphatic diepoxide), a polymer derived from one or more (meth)acrylate monomers (e.g., an alkyl(meth)acrylate homopolymer, a fluoroalkyl (meth)acrylate copolymer), a styrene-containing polymer, a polymer derived from N-vinylcarbazole and optionally other ethylenically unsaturated monomers, a polyimide, a $VF_2$-containing fluoropolymer, or combinations thereof. Such materials are described in more detail below.

Functionalized Soluble Polymers and Monomers

Soluble functionalized polymers suitable for use in acoustic sensors (either within the waveguide layer or an immobilization overlayer, or as an immobilizing waveguide material) are those that have two or more pendant groups independently selected from those having the following formulas:

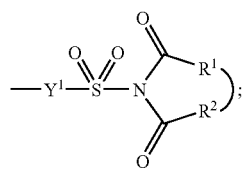
(I)

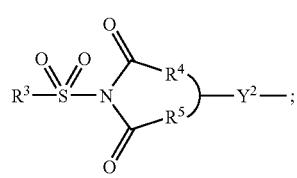
(II)

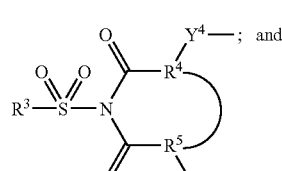
(III)

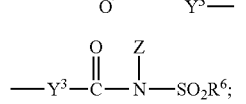
(IV)

wherein $R^1$, $R^2$, $R^3$, $R^4$, $R^5$, $R^6$, $Y^1$, $Y^2$, $Y^3$, $Y^4$, $Y^5$, and Z are defined herein below.

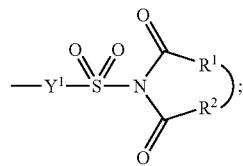
(I)

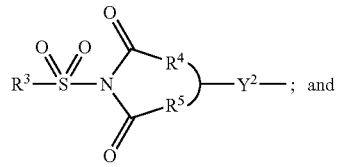
(II)

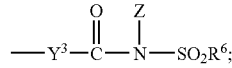
(IV)

wherein, $R^1$, $R^2$, $R^3$, $R^4$, $R^5$, $R^6$, $Y^1$, $Y^2$, $Y^3$, and Z are defined herein below.

Comonomers can be selected for several reasons, including dilution of the above identified monomers of the formula $A-R^7-X-C(O)-C(R^8)=CH_2$, thermal and mechanical stability, adhesion, etc. Examples of comonomers include lower alkyl acrylates and methacrylates, polyethylene glycol monoalkyl ether acrylates and methacrylates, vinyl ethers, styrenes, (meth)acrylamides, allyl ethers, strained internal olefins, and the like.

The second approach to preparing soluble polymers of the present invention involves addition of a functionally reactive amine capture group to a pre-existing polymer, the latter made by addition or condensation polymerization. For example, $ClC(O)C_8H_{16}C(O)$-Saccharin can be reacted with poly(methylmethacrylate-co-hydroxyethylmethacrylate) and polyvinylalcohol.

Herein, in Formula I, $R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group.

Herein, in Formulas II and III, $R^3$ is an alkyl, aryl, aralkyl, or $-NR^aR^b$ wherein $R^a$ and $R^b$ are each an alkyl group or taken together with the nitrogen atom to which they are attached form a four to eight membered heterocyclic group.

In certain embodiments of Formulas II and III, $R^3$ is an alkyl, aryl, or aralkyl. Suitable alkyl groups typically contain no greater than 30 carbon atoms, no greater than 20 carbon atoms, no greater than 10 carbon atoms, no greater than 6 carbon atoms, or no greater than 4 carbon atoms. In some compounds, the alkyl group is methyl, ethyl, or propyl. Suitable aryl groups typically contain 6 to 18 carbon atoms, 6 to 12 carbon atoms, or 6 carbon atoms. In some compounds, the aryl group is phenyl. An example of an aryl group is 4-methylphenyl. Suitable aralkyl groups typically contain an aryl group having 6 to 30 carbon atoms and an alkyl group having no greater than 30 carbon atoms.

In other embodiments of Formulas II and III, $R^3$ is a group $-NR^aR^b$ where $R^a$ and $R^b$ are alkyl groups having no greater than 10 carbon atoms, no greater than 6 carbon atoms, or no greater than 4 carbon atoms. Alternatively, the $R^a$ and $R^b$ groups can combine together with the nitrogen atom to which they are attached to form a 4 to 8 membered ring structure. For example, $R^a$ and $R^b$ can combine to form a five or six membered heterocyclic group having a nitrogen heteroatom.

Herein, in Formulas I and III, $R^4$ and $R^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group.

Herein, in Formula IV, $R^6$ is an alkyl, fluoroalkyl, chloroalkyl, aryl, $-NR^cR^d$ wherein $R^c$ and $R^d$ are each an alkyl group or taken together with the nitrogen atom to which they are attached form a four to eight membered cyclic group, or $R^6$ taken together with $R^e$ and the groups to which they are attached form the four to eight membered heterocyclic or heterobicyclic group that can be fused to the optional aromatic group, optional saturated or unsaturated cyclic group, or optional saturated or unsaturated bicyclic group.

In some embodiments of Formula IV, $R^6$ can be a $C_{1-30}$ alkyl, a $C_{1-10}$ alkyl, or a $C_{1-6}$ alkyl. In other embodiments of Formula IV, $R^6$ can be a $C_{1-30}$ fluoroalkyl, a $C_{1-10}$ fluoroalkyl, or a $C_{1-4}$ perfluoroalkyl group. In still other embodiments of Formula IV, $R^6$ can be a $C_{6-12}$ aryl. For example $R^6$ can be a phenyl group.

Herein, in Formula IV, Z is an alkyl, aryl, or $-(CO)R^e$. In some embodiments of Formula IV, Z can be alkyl or aryl. For example, Z can be a $C_{1-6}$ alkyl. In other examples, Z can be a $C_{6-12}$ aryl. In other embodiments of Formula IV, Z can be a $-(CO)R^e$ group, wherein $R^e$ together with $R^6$ and groups to which they are attached form a four to eight-membered heterocyclic or heterobicyclic group having a nitrogen heteroatom and a sulfur heteroatom, wherein the heterocyclic or heterobicyclic group can be fused to an optional aromatic group, optional saturated or unsaturated cyclic group, or optional saturated or unsaturated bicyclic group.

Herein, $Y^1$, $Y^2$, and $Y^3$ are each independently a single bond or a divalent group selected from the group consisting of an alkylene, heteroalkylene, arylene, heteroarylene, carbonyl, carbonyloxy, carbonylimino, oxy, thio, $-NR^f-$ where $R^f$ is hydrogen or alkyl, and combinations thereof. In certain embodiments, $Y^1$, $Y^2$, and $Y^3$ are each independently selected from the group consisting of groups having the following formulas $-Y^{1a}-Ar^1-$ and $-Ar^1-Y^{1a}-$, wherein: $Ar^1$ is an arylene; and $Y^{1a}$ is selected from the group consisting of a single bond, alkylene, heteroalkylene, carbonyl, carbonyloxy, carbonylimino, oxy, thio, $-NR^f-$ where $R^f$ is hydrogen or alkyl, and combinations thereof.

In certain embodiments, $Y^1$, $Y^2$, and $Y^3$ are each independently selected from the group consisting of groups having the following formulas: $-Y^{1a}-Ar^1-$ and $-Ar^1-Y^{1a}-$. In such formulas, $Ar^1$ is an arylene (preferably, a phenylene), and $Y^{1a}$ is selected from the group consisting of a single bond, alkylene, heteroalkylene, carbonyl, carbonyloxy, carbonylimino, oxy, thio, $-NR^f-$ where $R^f$ is hydrogen or alkyl, and combinations thereof.

In certain embodiments, $Y^1$, $Y^2$, and $Y^3$ each independently includes a first alkylene group linked to an arylene group with a group selected from the group consisting of a carbonyl, carbonyloxy, carbonylimino, oxy, thio, $-NR^f-$ where $R^f$ is hydrogen or alkyl, and combinations thereof. In certain of these embodiments, the first alkylene group is further linked to a second alkylene or a first heteroalkylene group with a group selected from the group consisting of a carbonyl, carbonyloxy, carbonylimino, oxy, thio, $-NR^f-$ where $R^f$ is hydrogen or alkyl, and combinations thereof. In certain of these embodiments, additional alkylene or heteroalkylene groups can be linked to the second alkylene or to the first heteroalkylene group with a group selected from the group consisting of a carbonyl, carbonyloxy, carbonylimino, oxy, thio, $-NR^f-$ where $R^f$ is hydrogen or alkyl, and combinations thereof.

In certain embodiments, $Y^1$, $Y^2$, and $Y^3$ each independently includes a first heteroalkylene group linked to an arylene with a group selected from the group consisting of a carbonyl, carbonyloxy, carbonylimino, oxy, thio, $-NR^f-$ where $R^f$ is hydrogen or alkyl, and combinations thereof. In certain of these embodiments, the first heteroalkylene group is further linked to a second heteroalkylene or to a first alkylene group with a group selected from the group consisting of a carbonyl, carbonyloxy, carbonylimino, oxy, thio, $-NR^f-$ where $R^f$ is hydrogen or alkyl, and combinations thereof. In certain of these embodiments, additional alkylene or heteroalkylene groups linked to the second heteroalkylene or to the first alkylene group with groups selected from the group consisting of carbonyl, carbonyloxy, carbonylimino group, oxy, thio, $-NR^f-$ where $R^f$ is hydrogen or alkyl, and combinations thereof.

In certain embodiments, $Y^1$, $Y^2$, and $Y^3$ each independently includes a first alkylene group connected to a second alkylene group or to a first heteroalkylene group with a group selected from the group consisting of a carbonyl, carbonylimino, carbonyloxy, oxy, thio, $-NR^f-$ where $R^f$ is hydrogen or alkyl, and combinations thereof. In certain of these embodiments, additional alkylene or heteroalkylene groups connected to the second alkylene group or the first heteroalkylene group with a group selected from the group consisting of a carbonyl, carbonylimino, carbonyloxy, oxy, thio, $-NR^f-$ where $R^f$ is hydrogen or alkyl, and combinations thereof. In certain embodiments, $Y^1$, $Y^2$, and $Y^3$ are each independently a heteroalkylene group. In certain embodiments, $Y^1$, $Y^2$, and $Y^3$ each independently includes a first heteroalkylene group connected to a second heteroalkylene group or to a first alkylene group with a group selected from the group consisting of a carbonyl, carbonylimino, carbonyloxy, oxy, thio, $-NR^f-$ where $R^f$ is hydrogen or alkyl, and combinations thereof. In certain of these embodiments, additional alkylene or heteroalkylene groups connected to the second heteroalkylene group or the first alkylene group.

In certain embodiments, $Y^1$, $Y^2$, and $Y^3$ are each independently a heteroalkylene having 1-30 carbon atoms and up to 30 heteroatoms selected from the group consisting of N, O, S, and combinations thereof, wherein the heteroalkylene group is linear, branched, cyclic, or combinations thereof.

In certain embodiments, $Y^1$, $Y^2$, and $Y^3$ are each independently an alkylene having 1-30 carbon atoms, wherein the alkylene group is linear, branched, cyclic, or combinations thereof. In certain of these embodiments, the alkylene group can be linear or branched with up to 20 carbon atoms. In certain embodiments, the alkylene is of the formula $(CH_2)_n$, where n is an integer of 1 to 20.

In certain embodiments, $Y^1$, $Y^2$ and $Y^3$ each independently includes an arylene group (preferably, including up to 18 carbon atoms, up to 12 carbon atoms, or up to 6 carbon atoms), in addition to one or more alkylene groups and one or more heteroalkylene groups.

Herein, $Y^4$ and $Y^5$ are each a bond.

Exemplary Formula I structures include, but are not limited to, the following:

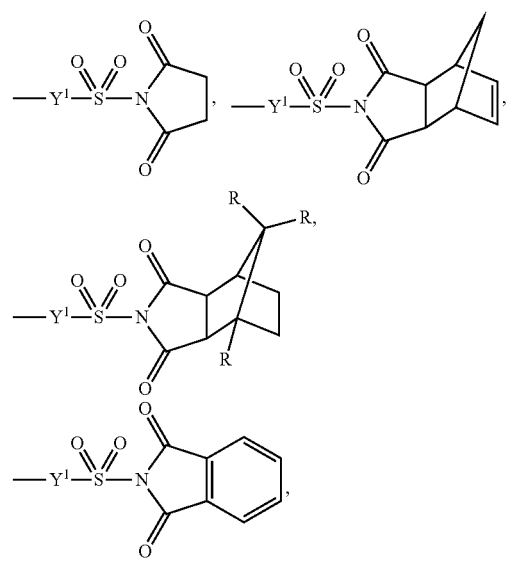

-continued

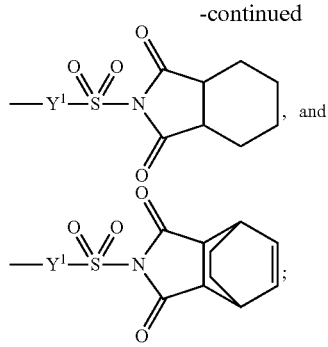
, and;

wherein R is an alkyl and $Y^1$ is the same as previously defined for Formula I. In certain of these exemplary embodiments, $Y^1$ can be —$Y^{1a}$—$Ar^1$— or —$Ar^1$—$Y^{1a}$—, wherein $Ar^1$ is an arylene (preferably, a phenylene), and $Y^{1a}$ is selected from the group consisting of a single bond, alkylene, heteroalkylene, carbonyl, carbonyloxy, carbonylimino, oxy, thio, —$NR^f$— where $R^f$ is hydrogen or alkyl, and combinations thereof. The functional groups of Formula I can be unsubstituted or substituted with a halo, alkyl, alkoxy, or combinations thereof.

Exemplary Formula I structures also include, but are not limited to, the following:

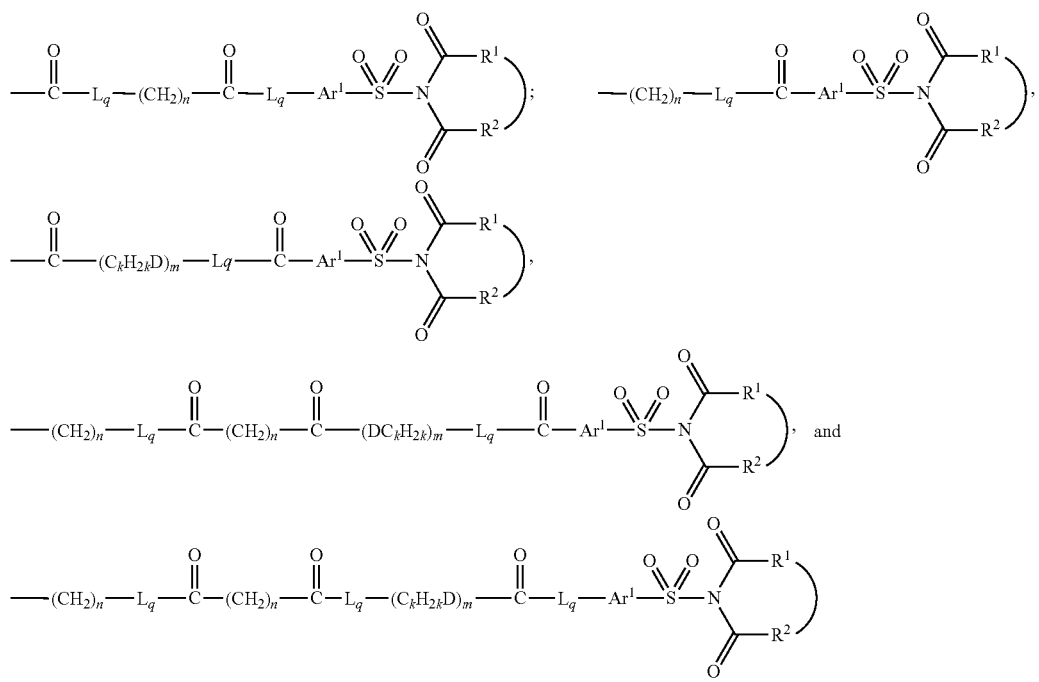

wherein: $R^1$ and $R^2$ are the same as previously defined for Formula I; each n is independently an integer of 1 to 100; m is an integer of 1 to 200; k is an integer of 2 to 4; D is oxygen, sulfur, or NH; $Ar^1$ is an arylene group; each L is independently oxygen or $NR^f$ where $R^f$ is hydrogen or alkyl; and q is in integer of 0 or 1. In such embodiments, preferably, n is no greater than 80, no greater than 60, no greater than 40, no greater than 20, or no greater than 10; preferably, m is no greater than 150, no greater than 100, no greater than 80, no greater than 60, no greater than 40, no greater than 20, or no greater than 10; preferably, k is equal to 2; preferably, D is oxygen; and preferably, $Ar^1$ is phenylene.

Exemplary Formula II structures include, but are not limited to, the following:

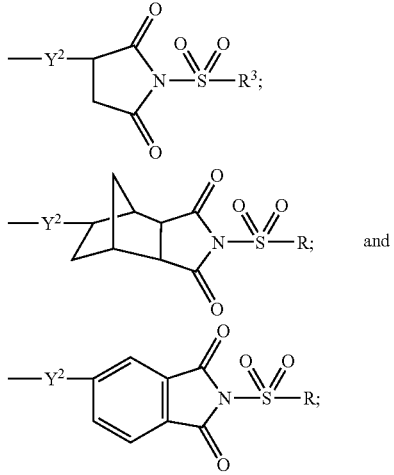
and

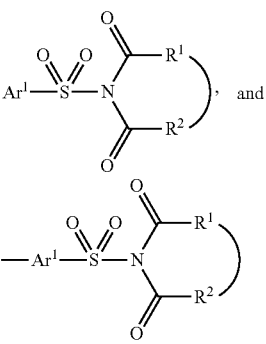

wherein $R^3$ and $Y^2$ are the same as previously defined for Formula II. The functional groups of Formula II can be unsubstituted or substituted with a halo, alkyl, alkoxy, or combinations thereof.

Exemplary Formula II structures also include, but are not limited to, the following:

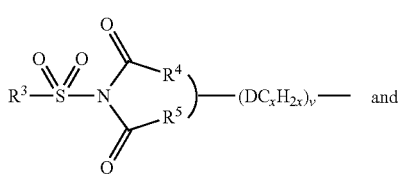
and

-continued

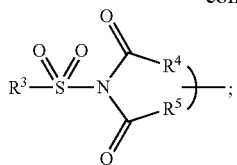

wherein: $R^3$, $R^4$, and $R^5$ are the same as previously defined for Formula II; v is an integer of 1 to 200; x is an integer of 1 to 4; and D is oxygen, sulfur, or NH. In such embodiments, preferably, v is no greater than 150, no greater than 100, no greater than 80, no greater than 60, no greater than 40, no greater than 20, no greater than 10, no greater than 5, no greater than 4, no greater than 3, no greater than 2, or equal to 1, and more preferably, v is 1 or 2; preferably, x is no greater than 3, no greater than 2, or equal to 1, and more preferably, x is 1 or 2; and preferably, D is oxygen or sulfur.

Exemplary Formula III structures include the following formulas:

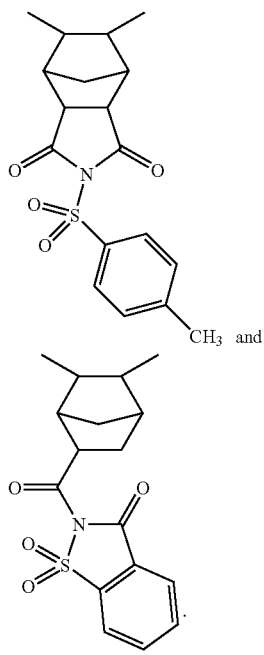

An exemplary Formula IV structure includes a heterocyclic group fused to an aromatic group as shown in the following formula:

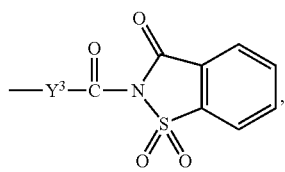

wherein $Y^3$ is the same as previously defined for Formula IV.

In certain embodiments, the soluble polymer of the present invention includes two or more pendant groups independently selected from the following formulas:

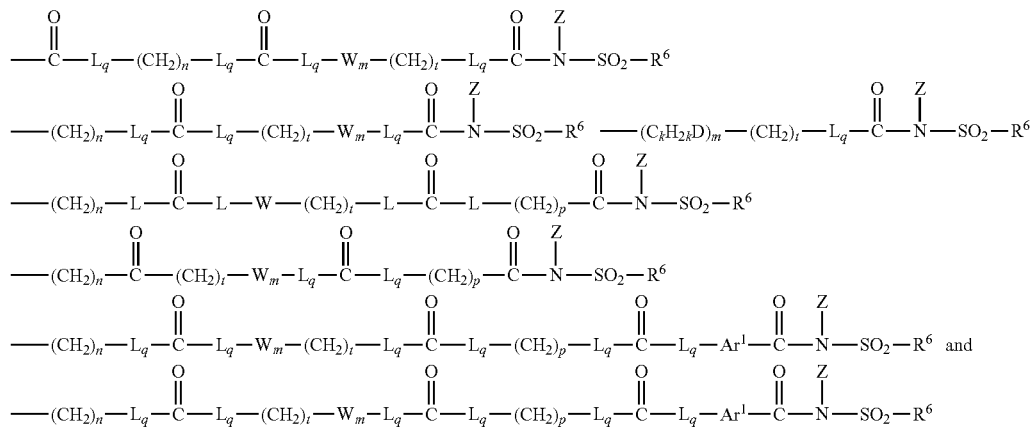

wherein: $R^6$ is the same as previously defined for Formula IV; W is $C_kH_{2k}D$ or $DC_kH_{2k}$; D is oxygen, sulfur, or NH (preferably, oxygen); n is an integer of 1 to 100 (preferably no greater than 80, no greater than 60, no greater than 40, no greater than 20, no greater than 10); m is an integer of 1 to 200 (preferably no greater than 150, no greater than 100, no greater than 80, no greater than 60, no greater than 40, no greater than 20, no greater than 10); p is an integer of 1 to 10 (preferably no greater than 8, no greater than 6, no greater than 4, or no greater than 2); q is an integer of 0 or 1; t is an integer of 0 to 12 (preferably no greater than 10, no greater than 8, no greater than 6, no greater than 4, no greater than 2, or equal to 0); k is an integer of 2 to 4 (preferably no greater than 3, no greater than 2, or equal to 2); and each L is independently oxygen or $NR^f$ where $R^f$ is hydrogen or alkyl; with the proviso that at least one L is present in each $-L_q-C(O)-L_q-$ moiety and there are no heteroatom-heteroatom bonds.

In certain embodiments, the soluble polymer of the present invention includes two or more pendant groups independently selected from the following formulas:

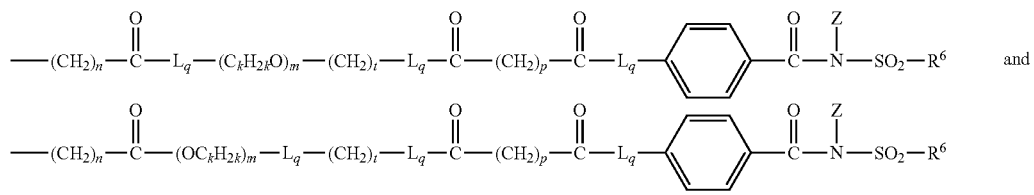

wherein: $R^6$ is the same as previously defined herein for Formula IV; n is an integer of 1 to 100 (preferably no greater than 80, no greater than 60, no greater than 40, no greater than 20, no greater than 10); m is an integer of 1 to 200 (preferably no greater than 150, no greater than 100, no greater than 80, no greater than 60, no greater than 40, no greater than 20, no greater than 10); p is an integer of 1 to 10 (preferably no greater than 8, no greater than 6, no greater than 4, or no greater than 2); t is an integer of 0 to 12 (preferably no greater than 10, no greater than 8, no greater than 6, no greater than 4, no greater than 2, or equal to 0); k is an integer of 2 to 4 (preferably no greater than 3, no greater than 2, or equal to 2); each L is independently oxygen or $NR^f$ where $R^f$ is hydrogen or alkyl; and q is 0 or 1.

Preferred monomeric compounds for the preparation of soluble polymers of the present invention are of the following formulas:

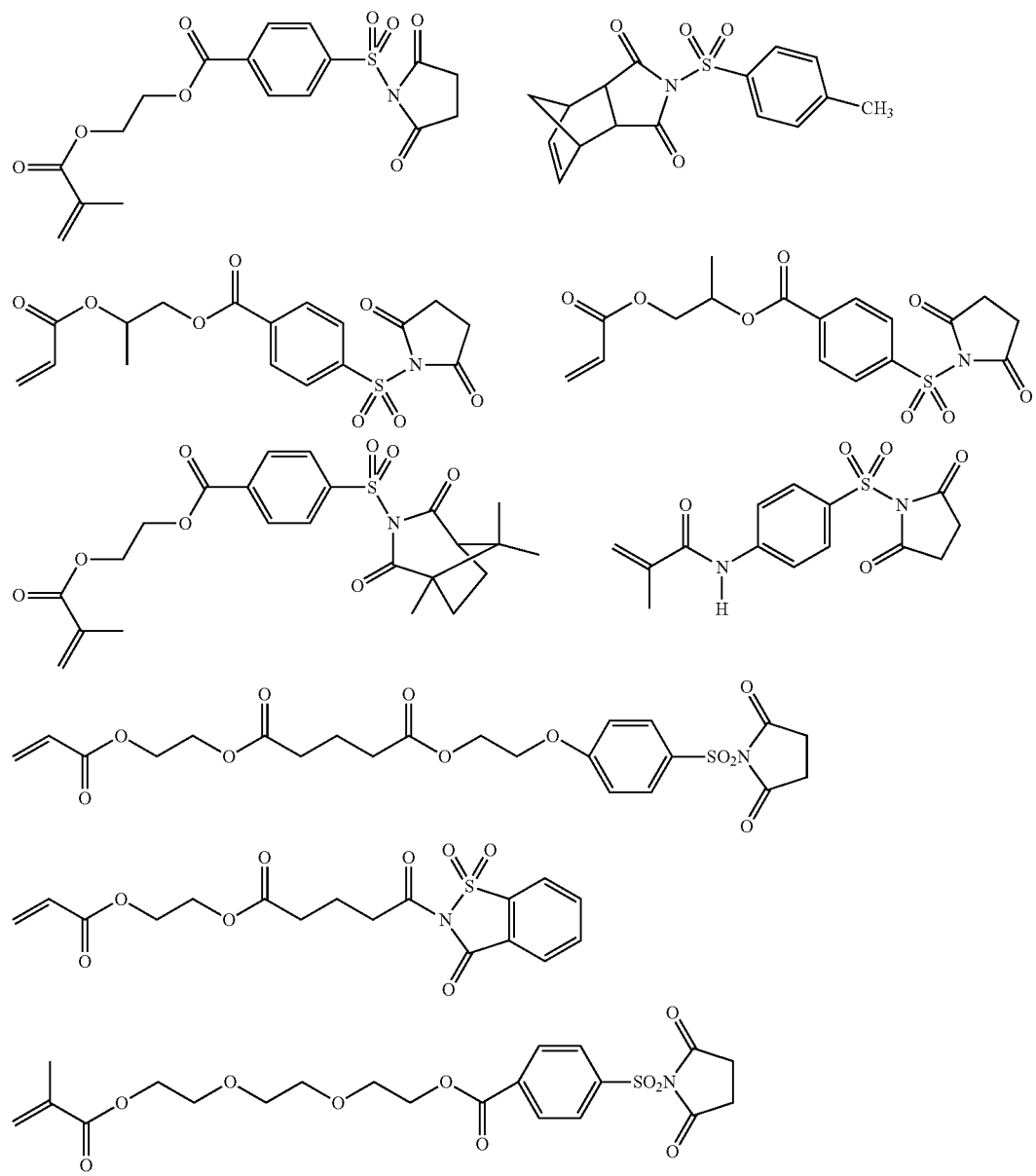

-continued

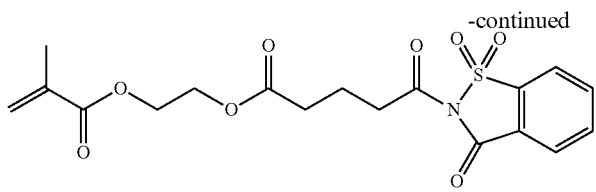

Preferred soluble polymers of the present invention are derived from two to four different (meth)acrylate monomers, wherein at least one monomer includes an acylsulfonamide group. Preferably, at least one monomer is of the formula $A-R^7-X-C(O)-C(R^8)=CH_2$ as described above.

Even more preferred soluble polymers are of the following formula:

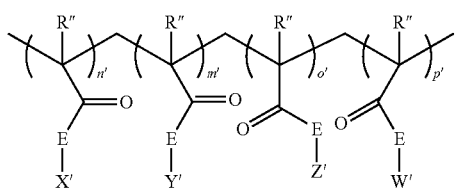

wherein:
each R" is independently H or $CH_3$;
each E is —O— or —$NR^f$—, where $R^f$ is hydrogen or alkyl;
m', n', o', p' represent the number of times each moiety is present in the polymer;
X', Y', Z', and W' are independently selected from the group consisting of alkyl (e.g., methyl or cycloalkyls such as isobornyl), aryl, hydroxy ester, alkoxyalkyl, alkoxyaryl, ether, fluoroalkyl, trialkoxysilylalkyl, and N-containing groups (e.g., dimethylaminoethyl group, saccharin group); and
at least one of X', Y', Z', or W' includes an acylsulfonamide group, and preferably the following N-containing group (wherein the bond to the carbonyl represents the attachment site of the group):

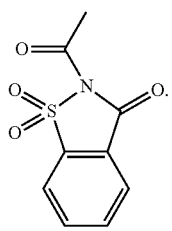

This representation of a preferred polymer includes at least two distinct moieties (i.e., formed from two different monomers). That is, the above formula represents a copolymer, terpolymer, or tetrapolymer. Preferably, it is a terpolymer. Such polymers are preferably random polymers, although they can be block or segmented polymers. These repeating moieties are present in sufficient numbers to form a polymer having a molecular weight of at least 1000, and preferably to over 1 million.

Preferably, at least one of X', Y', Z', or W' is the following group:

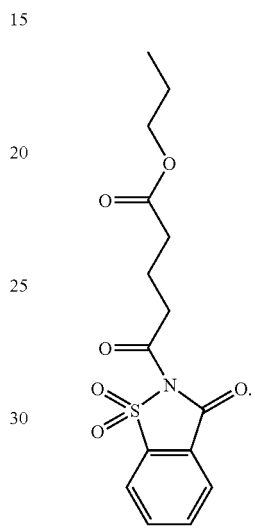

Such polymers can be constructed from at least two (preferably, three or four, and more preferably, three) distinct (meth)acrylate monomers combining X', Y', Z', and W' functionality. Suitable (meth)acrylates, include, for example, alkyl(meth)acrylates, aryl(meth)acrylates, hydroxy alkyl (meth)acrylates, N-containing (meth)acrylates, ether-containing (meth)acrylates, and fluoroalkyl(meth)acrylates.

Examples of alkyl(meth)acrylates include methyl-, ethyl-, butyl-, isobutyl-, n-hexyl-, 2-ethylhexyl-, isodecyl-, lauryl-, stearyl-, behenyl-, and isotridecyl-(meth)acrylate. Examples of cyclic (e.g., cycloalkyl and aryl) (meth)acrylates include benzyl-, isobornyl-, cyclohexyl-, and 3,3,5-trimethylcyclohexyl-(meth)acrylate. Examples of hydroxy alkyl(meth) acrylates include 2-hydroxyethyl and hydroxypropyl methacrylate. Examples of N-containing methacrylates include N,N-dimethylaminoethyl-, N,N-dimethylaminopropyl-, 2-trimethylammonium ethyl methacrylate chloride, and saccharins. Examples of ether-containing methacrylates include ethyl triglycol-, tetrahydrofurfuryl-, polyethyleneglycol, monomethylethyl-, and butyl diglycol-methacrylate. An example of a fluoroalkyl methacrylate includes N-methyl perfluorobutanesulfonamidoethyl methacrylate.

More preferred soluble polymers of the present invention are of the following formulas (wherein the variables m', n', o', p' represent repeat units in these random polymers of molecular weights of at least 1000, and preferably to over 1 million):

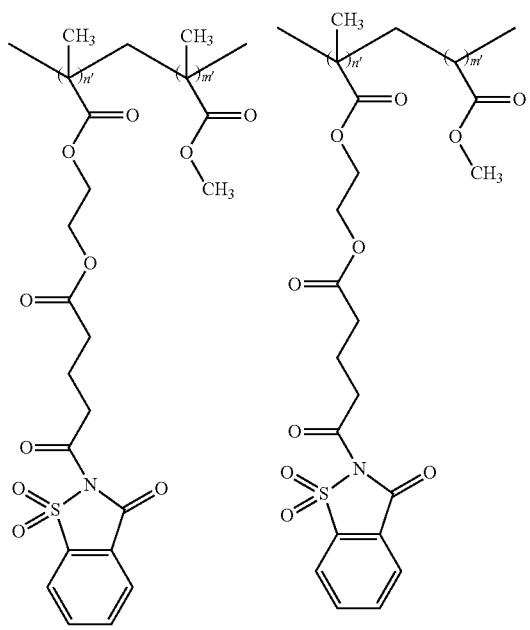
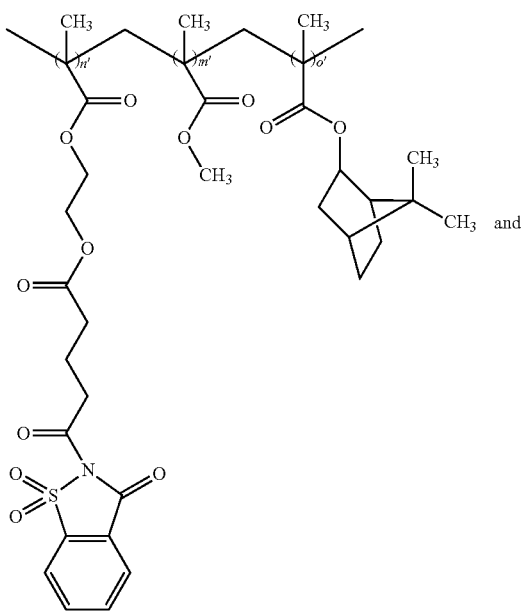
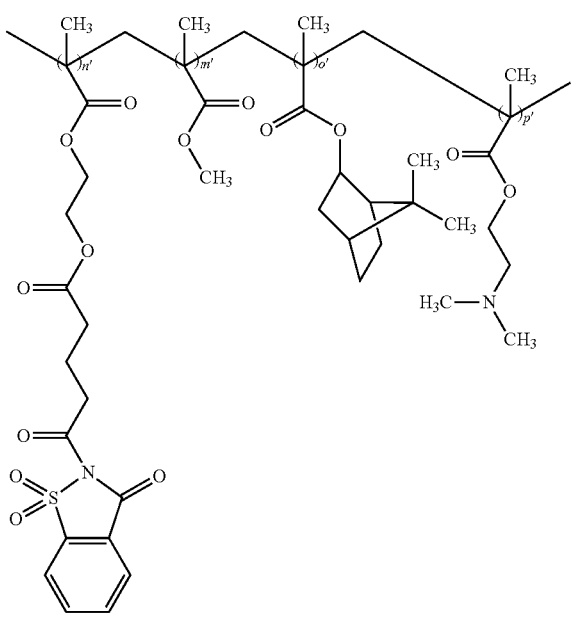
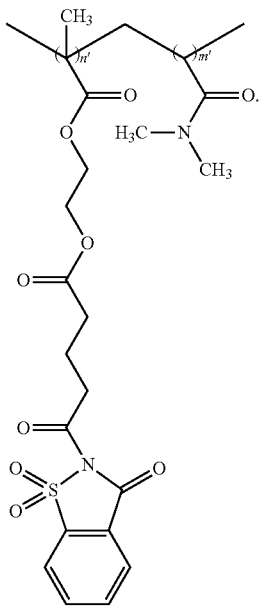

Particularly preferred soluble polymers of the present invention are of the following formula:

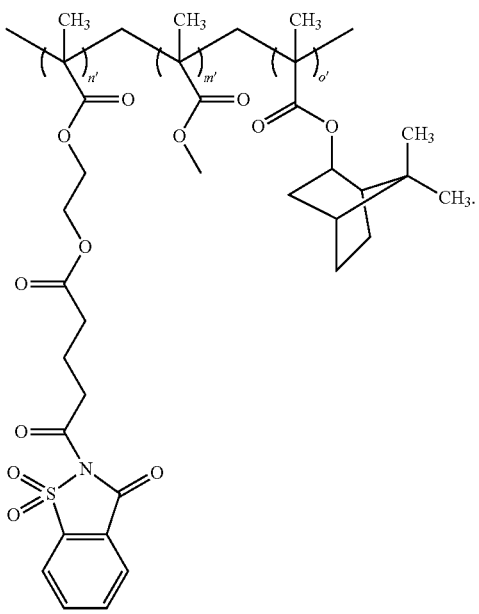

Polymerizable ethylenically unsaturated monomers bearing the amine-reactive group, suitable for preparing soluble polymers of the present invention, can be made by covalently combining functionally substituted amine-capture groups (A/R/G) (which represent the pendant groups of formulas I-IV described herein) with ethylenically unsaturated monomers bearing complementary functionality. For example, suitable functionalized monomers can be prepared as follows:

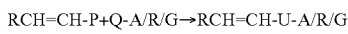

wherein "P" and "Q" are complementary and react covalently together, forming the "U" group which connects the A/R/G to the polymer when these monomers are (co)polymerized.

For instance, hydroxyethyl methacrylate can be reacted with glutaric anhydride to give glutaric acid mono(methacryloxyethyl)ester, which, as its acyl chloride, can be coupled with saccharin Na salt or N-4-hydroxyethoxybenzenesulfonylsuccinimide. This synthetic strategy allows evaluation of a wide variety of groups to optimize specific systems for attachment of the amine-reactive groups and subsequent capture of the amine. Readily available components such as polyethylene glycols and alkanediols which are expected to alter the responsiveness of the attached amine-reactive group. Such ethylenically unsaturated monomers are (co)polymerizable under standard free radical polymerization conditions, preferably in solution polymerizations. In these, a solution of the desired functionalized monomer, optionally one or more comonomers, and a thermal initiator is purged of oxygen and heated and agitated (typically for about 20 hours). Comonomers may be selected for their effects on solubility, glass transition, melting point, hydro- and oleo-phobicity/-philicity, adhesion to the substrate, and the like. Examples of comonomers include lower alkyl acrylates and methacrylates, polyethylene glycol monoalkyl ether acrylates and methacrylates, vinyl ethers, styrenes, acrylamides, methacrylamides, allyl ethers, strained internal olefins, and the like.

Alternatively, soluble polymers of the present invention can be made from functionally substituted preformed polymers. That is, a soluble polymer of the present invention can be made by covalently combining functionally substituted amine-capture groups with soluble polymers bearing complementary functionality (one with a P group and one with a complementary Q group as discussed above), or by generating the amine-capture group from soluble polymers bearing acylating or sulfonylating groups. For example, a copolymer of hydroxyethyl methacrylate and methyl methacrylate can be treated with the acid chloride derived from first reacting excess glutaryl chloride with saccharin Na salt or N-4-hydroxyethoxybenzenesulfonylsuccinimide and then removing the excess glutaryl chloride. An alternative strategy is exemplified by reacting saccharin Na salt with a copolymer of beta-acryloxyacryloyl chloride and an alkyl acrylate or by reacting N-4-hydroxyethoxybenzene-sulfonylsuccinimide with poly(5-norbornene-2-carbonylchloride).

Multifunctional Compounds

The present invention provides compounds are of the formula:

$$(A'\text{-})_y\text{-}Q$$

wherein each A' is independently selected from the group consisting of functional groups having the following formulas:

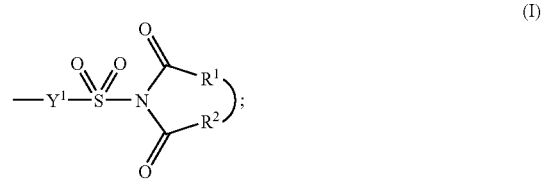 (I)

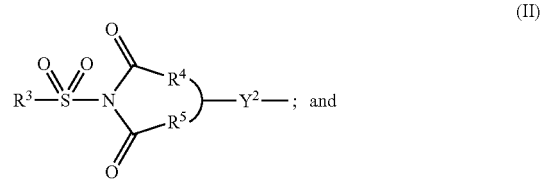 (II)

 (IV)

wherein $R^1$, $R^2$, $R^3$, $R^4$, $R^5$, $R^6$, $Y^1$, $Y^2$, $Y^3$, Z, y, and Q are defined herein.

Herein, in the compounds of the formula $(A'\text{-})_y\text{-}Q$, Q is a single bond or a y-valent atom or group. In certain embodiments, Q is an atom selected from C, N, S, O, or P. In certain embodiments, Q is a y-valent group containing up to 20 carbon atoms and up to 6 heteroatoms and/or functional groups (such as carbonyl groups). In certain embodiments, Q includes a ring system. Exemplary Q groups include carbonyl, alkylenes, alkanetriyl (i.e., a trivalent radical of an alkane), heteroalkylenes, arylenes, heteroarylenes, alkyleneoxy-alkylenes (e.g., —CHCH$_2$OCH$_2$CH—), alkylene-carbonyl-alkylenes, and combinations thereof (e.g., groups including both alkylene and arylene groups with or without heteroatoms and/or functional groups). Exemplary Q ring structures include the following:

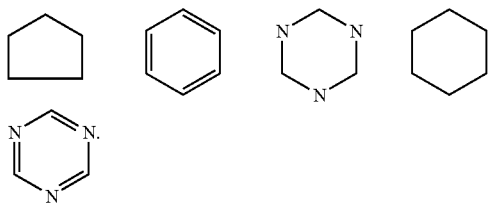

Herein, y is an integer of 2 to 10. In certain embodiments, y is an integer of 2 to 6. In some embodiments, y is an integer of 2 to 4. In some embodiments, y is an integer of 2 to 3. In some embodiments, y is 2 and the A' groups are terminal.

The A' groups may be the same or different. For synthetic convenience, however, they are often the same.

Herein, in Formula I, $R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group.

Herein, in Formula II, $R^3$ is an alkyl, aryl, aralkyl, or —$NR^aR^b$ wherein $R^a$ and $R^b$ are each an alkyl group or taken together with the nitrogen atom to which they are attached form a four to eight membered heterocyclic group.

In certain embodiments of Formula II, $R^3$ is an alkyl, aryl, or aralkyl group. Suitable alkyl groups typically contain no greater than 30 carbon atoms, no greater than 20 carbon atoms, no greater than 10 carbon atoms, no greater than 6 carbon atoms, or no greater than 4 carbon atoms. In some compounds, the alkyl group is methyl, ethyl, or propyl. Suitable aryl groups typically contain 6 to 18 carbon atoms, 6 to 12 carbon atoms, or 6 carbon atoms. In some compounds, the aryl group is phenyl. An example of an aryl group is 4-methylphenyl. Suitable aralkyl groups typically contain an aryl group having 6 to 30 carbon atoms and an alkyl group having no greater than 30 carbon atoms.

In other embodiments of Formula II, $R^3$ is a group —$NR^aR^b$ where $R^a$ and $R^b$ are alkyl groups having no greater than 10 carbon atoms, no greater than 6 carbon atoms, or no greater than 4 carbon atoms. Alternatively, the $R^a$ and $R^b$ groups can combine together with the nitrogen atom to which they are attached to form a 4 to 8 membered ring structure. For example, $R^a$ and $R^b$ can combine to form a five or six membered heterocyclic group having a nitrogen heteroatom.

Herein, in Formula II, $R^4$ and $R^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group.

Herein, in Formula III, $R^6$ is an alkyl, fluoroalkyl, chloroalkyl, aryl, —$NR^cR^d$ wherein $R^c$ and $R^d$ are each an alkyl group or taken together with the nitrogen atom to which they are attached form a four to eight membered cyclic group, or $R^6$ taken together with $R^e$ and the groups to which they are attached form the four to eight membered heterocyclic or heterobicyclic group that can be fused to the optional aromatic group, optional saturated or unsaturated cyclic group, or optional saturated or unsaturated bicyclic group.

In some embodiments of Formula III, $R^6$ can be a $C_{1-30}$ alkyl, a $C_{1-10}$ alkyl, or a $C_{1-6}$ alkyl. In other embodiments of Formula III, $R^6$ can be a $C_{1-30}$ fluoroalkyl, a $C_{1-10}$ fluoroalkyl, or a $C_{1-4}$ perfluoroalkyl group. In still other embodiments of Formula III, $R^6$ can be a $C_{6-12}$ aryl. For example $R^6$ can be a phenyl group.

Herein, Z is an alkyl, aryl, or —(CO)$R^e$. In some embodiments of Formula III, Z can be alkyl or aryl. For example, Z can be a $C_{1-6}$ alkyl. In other examples, Z can be a $C_{6-12}$ aryl. In other embodiments of Formula I, Z can be a —(CO)$R^e$ group, wherein $R^e$ together with $R^6$ and groups to which they are attached form a four to eight membered heterocyclic or heterobicyclic group having a nitrogen heteroatom and a sulfur heteroatom, wherein the heterocyclic or heterobicyclic group can be fused to an optional aromatic group, optional saturated or unsaturated cyclic group, or optional saturated or unsaturated bicyclic group.

Herein, $Y^1$, $Y^2$, and $Y^3$ are each independently a single bond or a divalent group selected from the group consisting of an alkylene, heteroalkylene, arylene, heteroarylene, carbonyl, carbonyloxy, carbonylimino, oxy, thio, —$NR^f$— where $R^f$ is hydrogen or alkyl, and combinations thereof. In certain embodiments, $Y^1$, $Y^2$, and $Y^3$ are each independently selected from the group consisting of groups having the following formulas —$Y^{1a}$—$Ar^1$— and —$Ar^1$—$Y^{1a}$—, wherein: $Ar^1$ is an arylene; and $Y^{1a}$ is selected from the group consisting of a single bond, alkylene, heteroalkylene, carbonyl, carbonyloxy, carbonylimino, oxy, thio, —$NR^f$— where $R^f$ is hydrogen or alkyl, and combinations thereof.

In certain embodiments, $Y^1$, $Y^2$, and $Y^3$ are each independently selected from the group consisting of groups having the following formulas: —$Y^{1a}$—$Ar^1$— and —$Ar^1$—$Y^{1a}$—. In such formulas, $Ar^1$ is an arylene (preferably, a phenylene), and $Y^{1a}$ is selected from the group consisting of a single bond, alkylene, heteroalkylene, carbonyl, carbonyloxy, carbonylimino, oxy, thio, —$NR^f$— where $R^f$ is hydrogen or alkyl, and combinations thereof.

In certain embodiments, $Y^1$, $Y^2$, and $Y^3$ each independently includes a first alkylene group linked to an arylene group with a group selected from the group consisting of a carbonyl, carbonyloxy, carbonylimino, oxy, thio, —$NR^f$— where $R^f$ is hydrogen or alkyl, and combinations thereof. In certain of these embodiments, the first alkylene group is further linked to a second alkylene or a first heteroalkylene group with a group selected from the group consisting of a carbonyl, carbonyloxy, carbonylimino, oxy, thio, —$NR^f$— where $R^f$ is hydrogen or alkyl, and combinations thereof. In certain of these embodiments, additional alkylene or heteroalkylene groups can be linked to the second alkylene or to the first heteroalkylene group with a group selected from the group consisting of a carbonyl, carbonyloxy, carbonylimino, oxy, thio, —$NR^f$— where $R^f$ is hydrogen or alkyl, and combinations thereof.

In certain embodiments, $Y^1$, $Y^2$, and $Y^3$ each independently includes a first heteroalkylene group linked to an arylene with a group selected from the group consisting of a carbonyl, carbonyloxy, carbonylimino, oxy, thio, —$NR^f$— where $R^f$ is hydrogen or alkyl, and combinations thereof. In certain of these embodiments, the first heteroalkylene group is further linked to a second heteroalkylene or to a first alkylene group with a group selected from the group consisting of a carbonyl, carbonyloxy, carbonylimino oxy, thio, —$NR^f$— where $R^f$ is hydrogen or alkyl, and combinations thereof. In certain of these embodiments, additional alkylene or heteroalkylene groups linked to the second heteroalkylene or to the first alkylene group with groups selected from the group consisting of carbonyl, carbonyloxy, carbonylimino group, oxy, thio, —$NR^f$— where $R^f$ is hydrogen or alkyl, and combinations thereof.

In certain embodiments, $Y^1$, $Y^2$, and $Y^3$ each independently includes a first alkylene group connected to a second alkylene group or to a first heteroalkylene group with a group selected from the group consisting of a carbonyl, carbonylimino, carbonyloxy, oxy, thio, —$NR^f$— where $R^f$ is hydrogen or alkyl, and combinations thereof. In certain of these embodiments, additional alkylene or heteroalkylene groups connected to the second alkylene group or the first heteroalkylene group with a group selected from the group consisting of a carbonyl, carbonylimino, carbonyloxy, oxy, thio, —NR$^f$— where R$^f$ is hydrogen or alkyl, and combinations thereof.

In certain embodiments, Y$^1$, Y$^2$, and Y$^3$ each independently includes a first heteroalkylene group connected to a second heteroalkylene group or to a first alkylene group with a group selected from the group consisting of a carbonyl, carbonylimino, carbonyloxy, oxy, thio, —NR$^f$— where R$^f$ is hydrogen or alkyl, and combinations thereof. In certain of these embodiments, additional alkylene or heteroalkylene groups connected to the second heteroalkylene group or the first alkylene group.

In certain embodiments, Y$^1$, Y$^2$, and Y$^3$ are each independently a heteroalkylene having, for example, 1-30 carbon atoms and up to 30 heteroatoms selected from the group consisting of N, O, S, and combinations thereof, wherein the heteroalkylene group is linear, branched, cyclic, or combinations thereof.

In certain embodiments, Y$^1$, Y$^2$, and Y$^3$ are each independently an alkylene having 1-30 carbon atoms, wherein the alkylene group is linear, branched, cyclic, or combinations thereof. In certain of these embodiments, the alkylene can be straight chain or branched with 1-20 carbon atoms. In certain of these embodiments, the alkylene is of the formula $(CH_2)_n$, where n is an integer of 1 to 20.

In certain embodiments, Y$^1$, Y$^2$, and Y$^3$ each independently includes an arylene group (preferably, including up to 18 carbon atoms, up to 12 carbon atoms, or up to 6 carbon atoms), in addition to one or more alkylene groups and one or more heteroalkylene groups.

Exemplary Formula I structures include, but are not limited to, the following:

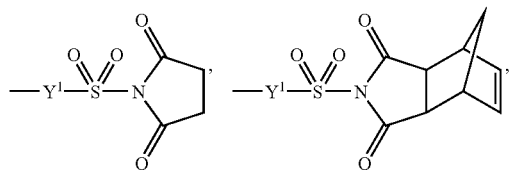

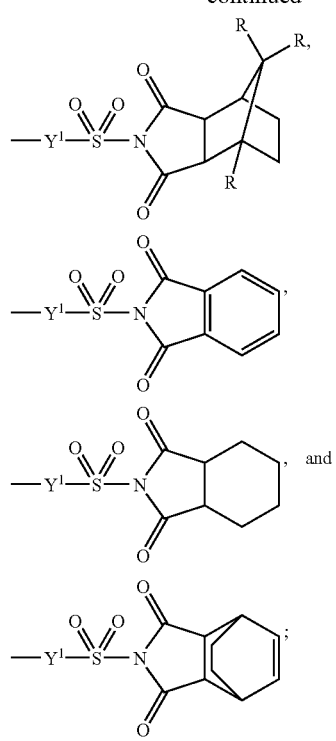

wherein: R is an alkyl; and Y$^1$ is the same as previously defined for Formula I. In certain of these exemplary embodiments, Y$^1$ can be —Y$^{1a}$—Ar$^1$— or —Ar$^1$—Y$^{1a}$—, wherein Ar$^1$ is an arylene (preferably, a phenylene), and Y$^{1a}$ is selected from the group consisting of a single bond, alkylene, heteroalkylene, carbonyl, carbonyloxy, carbonylimino, oxy, thio, —NR$^f$— where R$^f$ is hydrogen or alkyl, and combinations thereof. The functional groups of Formula I can be unsubstituted or substituted with a halo, alkyl, alkoxy, or combinations thereof.

Exemplary Formula I structures also include, but are not limited to, the following:

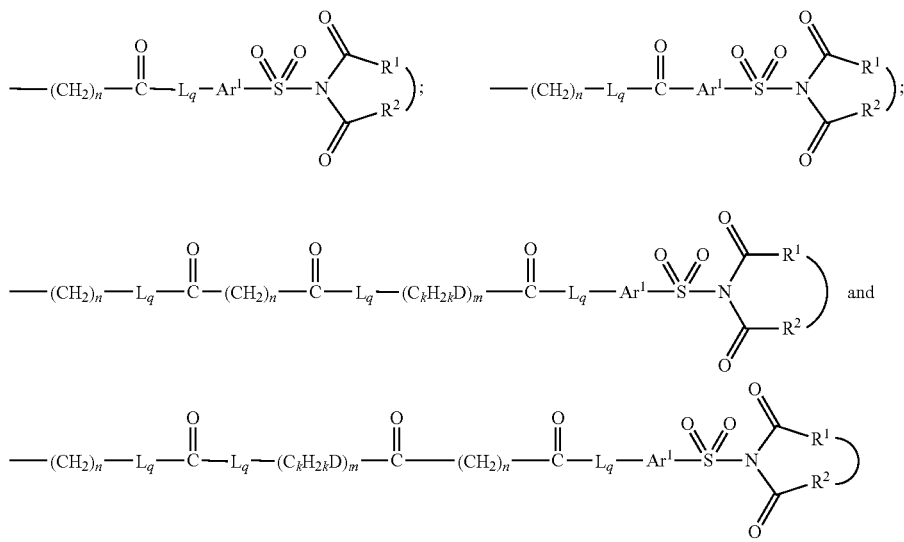

wherein: $R^1$ and $R^2$ are is the same as previously defined for Formula I; each n is independently an integer of 1 to 100; m is an integer of 1 to 200; k is an integer of 2 to 4; D is oxygen, sulfur, or NH; $Ar^1$ is an arylene group; each L is independently oxygen or $NR^f$ where $R^f$ is hydrogen or alkyl; and q is an integer of 0 or 1. In such embodiments, preferably, n is no greater than 80, no greater than 60, no greater than 40, no greater than 20, or no greater than 10; preferably, m is no greater than 150, no greater than 100, no greater than 80, no greater than 60, no greater than 40, no greater than 20, or no greater than 10; preferably, k is equal to 2; preferably, D is oxygen; and preferably, $Ar^1$ is phenylene.

Exemplary Formula II structures include, but are not limited to, the following:

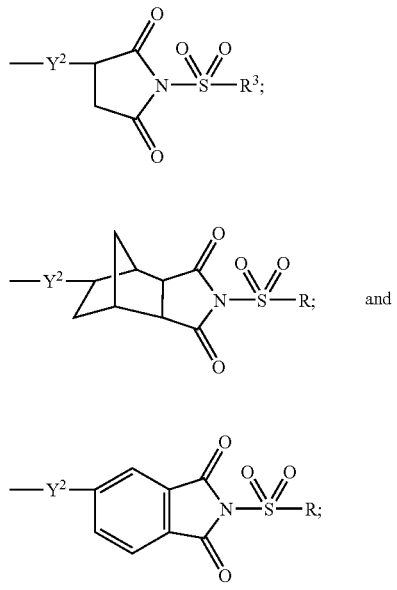

wherein $R^3$ and $Y^2$ are the same as previously defined for Formula II. The functional groups of Formula II can be unsubstituted or substituted with a halo, alkyl, alkoxy, or combinations thereof.

Exemplary Formula II structures also include, but are not limited to, the following:

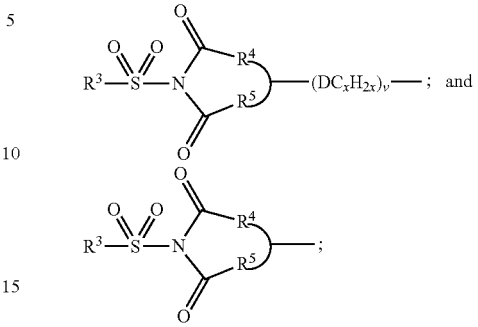

wherein: $R^3$, $R^4$, and $R^5$ are the same as previously defined for Formula II; v is an integer of 1 to 200; x is an integer of 1 to 4; and D is oxygen, sulfur, or NH. In such embodiments, preferably, v is no greater than 150, no greater than 100, no greater than 80, no greater than 60, no greater than 40, no greater than 20, no greater than 10, no greater than 5, no greater than 4, no greater than 3, no greater than 2, or equal to 1, and more preferably, v is 1 or 2; preferably, x is no greater than 3, no greater than 2, or equal to 1, and more preferably, x is 1 or 2; and preferably, D is oxygen or sulfur.

An exemplary Formula III structure includes a heterocyclic group fused to an aromatic group as shown in the following formula:

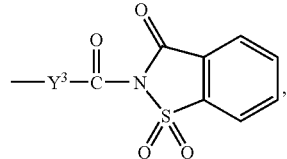

wherein $Y^3$ is the same as previously defined for Formula III.

In certain embodiments, the multifunctional compounds of the present invention include two or more pendant groups independently selected from the following formulas:

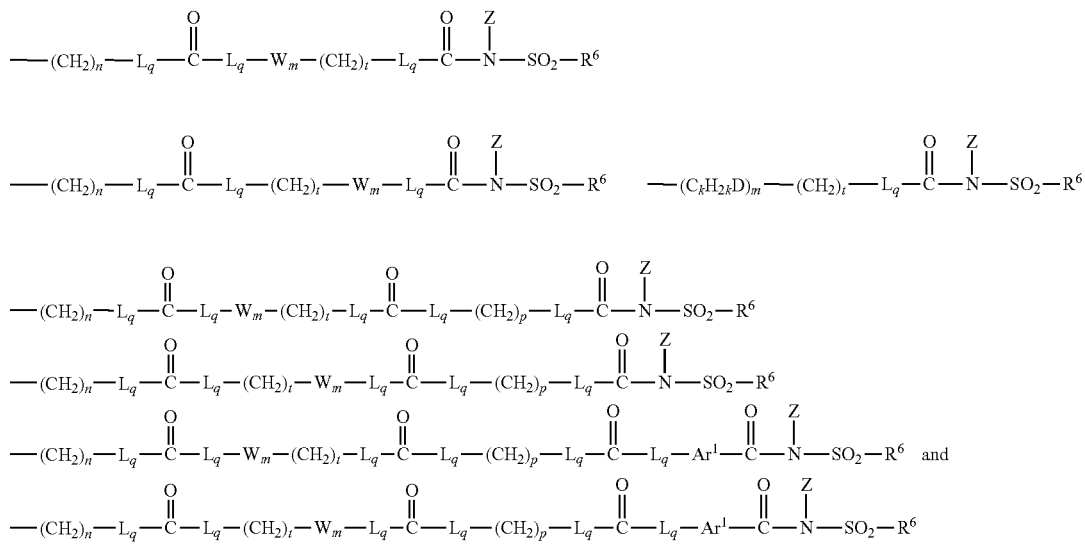

wherein: W is $C_kH_{2k}D$ or $DC_kH_{2k}$; D is oxygen, sulfur, or NH (preferably, oxygen); n is an integer of 1 to 100 (preferably no greater than 80, no greater than 60, no greater than 40, no greater than 20, no greater than 10); m is an integer of 1 to 200 (preferably no greater than 150, no greater than 100, no greater than 80, no greater than 60, no greater than 40, no greater than 20, no greater than 10); p is an integer of 1 to 10 (preferably no greater than 8, no greater than 6, no greater than 4, or no greater than 2); q is an integer of 0 or 1; t is an integer of 0 to 12 (preferably no greater than 10, no greater than 8, no greater than 6, no greater than 4, no greater than 2, or equal to 0); k is an integer of 2 to 4 (preferably no greater than 3, no greater than 2, or equal to 2); and each L is independently oxygen or $NR^f$ where $R^f$ is hydrogen or alkyl; with the proviso that at least one L is present in each $-L_q-C(O)-L_q-$ moiety and there are no heteroatom-heteroatom bonds.

In certain embodiments, the multifunctional compounds of the present invention include two or more pendant groups independently selected from the following formulas:

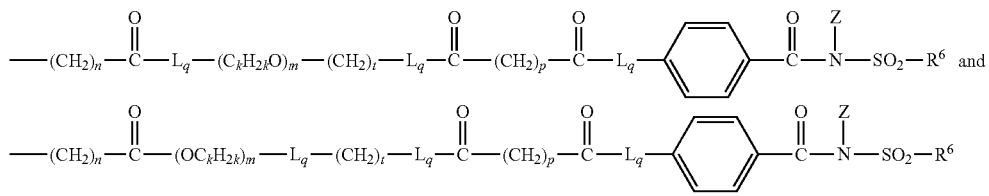

wherein: n is an integer of 1 to 100 (preferably no greater than 80, no greater than 60, no greater than 40, no greater than 20, no greater than 10); m is an integer of 1 to 200 (preferably no greater than 150, no greater than 100, no greater than 80, no greater than 60, no greater than 40, no greater than 20, no greater than 10); p is an integer of 1 to 10 (preferably no greater than 8, no greater than 6, no greater than 4, or no greater than 2); t is an integer of 0 to 12 (preferably no greater than 10, no greater than 8, no greater than 6, no greater than 4, no greater than 2, or equal to 0); k is an integer of 2 to 4 (preferably no greater than 3, no greater than 2, or equal to 2); each L is independently oxygen or $NR^f$ where $R^f$ is hydrogen or alkyl; and q is an integer of 0 or 1.

Preferred multifunctional compounds are difunctional or trifunctional compounds of the following formulas:

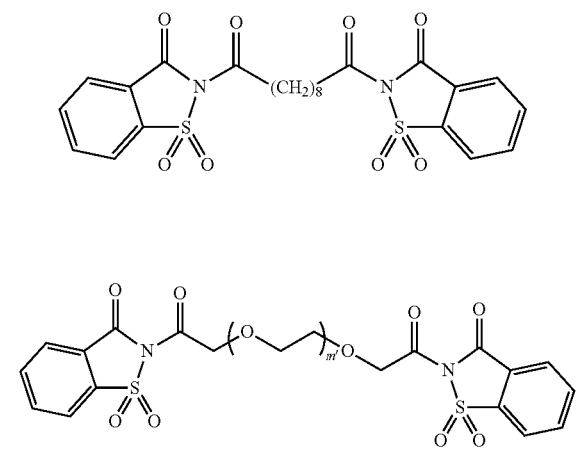

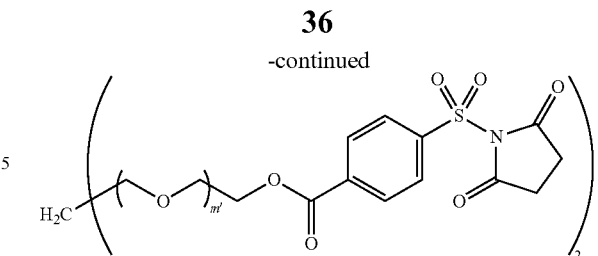

wherein m' is an integer of 1 to 200 (preferably no greater than 150, no greater than 100, no greater than 80, no greater than 60, no greater than 40, no greater than 20, no greater than 10).

The functionally substituted amine capture agents of Applicants' U.S. Pat. Nos. 7,361,767, 7,169,933, 7,423,155 and 7,179,923, can be used to make the multifunctional compounds of the present invention. This can be done by attaching such compounds to a core Q group bearing y complementary functional groups to give the multifunctional amine capture agents of the present invention. For example, ClC(O)$C_6H_4SO_2N(C(O)CH_2)_2$ can be reacted with a diol such as polyethylene glycol, or a triol such as trimethylolpropane ethoxylate. Also, a silane such as $(EtO)_3SiC_{10}H_{22}C(O)$-saccharin can be pre-reacted with tetraethoxysilane to form a sol-gel condensate including multiple amine capture acyl saccharin groups. Alternatively, the amine capture group can be formed at the terminus of a multifunctional Q group by the reactions illustrated in the Applicants' U.S. Pat. Nos. 7,361,767, 7,169,933, 7,423,155 and 7,179,923. For example, a Q group-containing multifunctional acid chloride can be reacted with sodium saccharin, or a Q group-containing multisulfonamide can be reacted with succinoyl chloride.

Functionalized Compounds with Substrate Reactive Groups

Another class of compound suitable for use in the acoustic sensors of the present invention (typically, in the immobilization layer) include compounds with one or two functional groups represented by Formulas I, II, or IV, wherein each Y group ($Y^1$, $Y^2$, $Y^3$) is bonded to a substrate reactive-functional group independently selected from the group consisting of a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, ethylenically unsaturated group, and combinations thereof. An exemplary immobilization layer includes N-(11-trichlorosilylundecenoyl)saccharin. Such compounds are disclosed in Applicants' Assignee's U.S. Pat. Nos. 7,361,767, 7,169,933, 7,423,155 and 7,179,923.

(Meth)Acrylate Polymers

Polymers derived from one or more (and preferably, two or more) (meth)acrylates (i.e., acrylates or methacrylates) with each other or other ethylenically unsaturated monomers are particularly suitable for waveguides in acoustic sensors. Preferably, polymers derived from one or more different monomers, wherein at least one is a (meth)acrylate monomer, are particularly desirable waveguides in acoustic sensors. Such polymers may or may not be functionalized with groups other than those functional groups of Formulas I, II, m, or IV. Thus, in such polymers, other functionalities may be possible (e.g., perfluorobutanesulfonimido). Suitable (meth)acrylates, include, for example, alkyl(meth)acrylates, aryl (meth)acrylates, hydroxy alkyl(meth)acrylates (which are often considered within the scope of alkyl(meth)acrylates, as discussed below), N-containing (meth)acrylates, ether-containing (meth)acrylates, and fluoroalkyl(meth)acrylates. Preferably, the (meth)acrylates are alkyl(meth)acrylates.

Suitable alkyl(meth)acrylates include those having the structure:

$CH_2$=C(R')—CO—O$R^2$ wherein $R^1$ is hydrogen or methyl, and $R^2$ is an alkyl group preferably containing one to sixteen carbon atoms. The $R^2$ group can be substituted with one or more, and typically one to three, moieties such as hydroxy, halo, phenyl, and alkoxy, for example. Suitable alkyl(meth)acrylates therefore encompass hydroxy alkyl (meth)acrylates. The alkyl(meth)acrylate typically is an ester of acrylic or methacrylic acid. Preferably, $R^1$ is hydrogen or methyl and $R^2$ is an alkyl group having two to twelve carbon atoms. Most preferably, $R^1$ is hydrogen or methyl and $R^2$ is an alkyl group having two to four carbon atoms.

Examples of suitable (meth)acrylates include, but are not limited to, methyl(meth)acrylate, ethyl(meth)acrylate, propyl (meth)acrylate, isopropyl(meth)acrylate, butyl(meth)acrylate, isobutyl(meth)acrylate, pentyl(meth)acrylate, isoamyl (meth)acrylate, hexyl(meth)acrylate, 2-ethylhexyl(meth) acrylate, cyclohexyl(meth)acrylate, decyl(meth)acrylate, isodecyl(meth)acrylate, benzyl(meth)acrylate, lauryl(meth) acrylate, isobornyl(meth)acrylate, octyl(meth)acrylate, nonyl(meth)acrylate, hydroxyethyl acrylate (HEA), hydroxyethyl methacrylate (HEMA), hydroxypropyl(meth)acrylate (HPMA), and N,N-dimethylaminoethyl methacrylate.

Difunctional (meth)acrylate monomers may be used in these polymers as well. Examples include ethylene glycol di(meth)acrylate, 1,6-hexanediol di(meth)acrylate, allyl methacrylate, and the like.

Fluorinated (meth)acrylate monomers may be used in these polymers as well. Examples include N-methyl perfluorobutanesulfonamidoethyl methacrylate and perfluoroalkyl (meth)acrylate esters with fluorocarbon alkyl chains F($CF_2CF_2$)$_n$ where n=4-20.

Other ethylenically unsaturated comonomers can be used in making such (meth)acrylate polymers. Such comonomers can be selected for several reasons, including dilution of the above-identified monomers, thermal and mechanical stability, adhesion, acoustic properties, etc.

Suitable ethylenically unsaturated comonomers include any of the (meth)acrylates described above as well as olefins (e.g., ethylene, propylenes, butylenes, etc.), diolefins (e.g., butadiene), styrene, alpha-methylstyrene, halostyrene, isoprene, diallylphthalate, divinylbenzene, vinyl toluene, vinyl ether, allyl ether, vinyl naphthalene, acrylonitrile, acrylamide, methacrylamide, methacrylonitrile, vinyl acetate, vinyl propionate, vinyl butyrate, vinyl stearate, N-isobutoxymethyl acrylamide, N-butoxymethyl acrylamide, and the like.

Preferred classes of polymers derived from two or more (meth)acrylates (i.e., acrylates or methacrylates) with each other or other ethylenically unsaturated monomers include nonfunctional (meth)acrylate homopolymers, nonfunctional (meth)acrylate copolymers, terpolymers or tetrapolymers, and fluorinated (meth)acrylate copolymers.

In one embodiment of (meth)acrylate-containing polymers, the present invention provides a polymer produced from the reaction product of 5 parts to 95 parts of a hydrophobic alkyl(meth)acrylate or (meth)acrylamide; 95 parts to 5 parts of a lower (i.e., C1-C3) alkyl(meth) acrylate; and optionally a crosslinking monomer or monomer that includes a functional group selected from hydroxyl, isocyanato, carboxyl, sulfonic acid, phosphonic acid, or amide. Preferred hydrophobic (meth)acrylates include alkyl(meth)acrylates having 4 or more carbons, wherein the alkyl can be linear, branched, cyclic, and aromatic, such as 2-ethylhexyl, octyl, isooctyl, decyl, isodecyl, isobornyl, naphtyl, phenyl, adamantyl, butyl, octadecyl, behenyl. A preferred hydrophobic acrylamide includes N-octyl acrylamide. Preferred lower (meth) acrylates include methyl(meth)acrylate and ethyl(meth)acrylate.

Preferred examples of nonfunctional (meth)acrylate homopolymers include polymethyl methacrylate (PMMA), polyisobornyl methacrylate (PIBMA), polymers of hydroxy ethyl methacrylate (HEMA). Such materials are suitable for use in the waveguide layer of the acoustic sensors described herein. PMMA is known for use as a waveguide in an acoustic sensor (see, for example, G. L. Harding et al., Smart Mater. Struct., 6, 716-720 (1997)).

Preferred examples of nonfunctional (meth)acrylate copolymers include a 50/50 copolymer of isobornyl(meth) acrylate and methyl(meth)acrylate (e.g., poly(IBMA/MMA)) including compositional ratios of 75/25 to 25/75, for example, and terpolymers of isobornyl(meth)acrylate, methyl(meth)acrylate, and hydroxy ethyl(meth)acrylate (e.g., poly(IBMA/MMA/HEMA)) including compositional ratios of 45/50/5 and 40/50/10, for example. Such materials are suitable for use in the waveguide layer of the acoustic sensors described herein. These nonfunctional (meth)acrylate copolymers are particularly desirable as waveguides in combination with the functionalized materials, especially the functionalized soluble polymers, described herein in the immobilization overlayers.

Preferred examples of fluorinated (meth)acrylate copolymers include poly(styrene/MeFBSEMA/A174), which is a 47.5/47.5 copolymer of polystyrene and N-methyl perfluorobutanesulfonamidoethyl methacrylate containing 5% of silane-A174 ([3-(methacryloyloxy)propyl]trimethoxysilane from GSF Chemicals, Tullytown, Pa.); and poly(MMA/MeFBSEMA/A174), which is a 47.5/47.5 copolymer of polymethyl methacrylate and N-methyl perfluorobutanesulfonamidoethyl methacrylate, containing 5% of Silane-A174 ([3-(methacryloyloxy)propyl]trimethoxysilane from GSF Chemicals, Tullytown, Pa.). Such materials are suitable for use in the waveguide layer of the acoustic sensors described herein.

VF$_2$-containing Fluoropolymers

Fluoropolymer materials suitable for use in the waveguide layer of the acoustic sensors described herein include polymers (including copolymers, terpolymers, etc.) with interpolymerized units derived from vinylidene fluoride (sometimes referred to as "VF$_2$" or "VDF"). Preferably fluoropolymer materials of this preferred class include at least 3 percent by weight (wt-%) of interpolymerized units derived from VF$_2$. Such polymers may be homopolymers of VF$_2$, copolymers, terpolymers, etc. of VF$_2$ and other ethylenically unsaturated monomers. A particularly preferred such polymer includes interpolymerized units derived from vinylidene fluoride and hexafluoropropylene.

Useful fluorine-containing monomers for preparing VF$_2$-containing polymers include hexafluoropropylene ("HFP"), tetrafluoroethylene ("TFE"), chlorotrifluoroethylene ("CTFE"), 2-chloropentafluoro-propene, perfluoroalkyl vinyl ethers (e.g., $CF_3OCF=CF_2$ or $CF_3CF_2OCF=CF_2$), 1-hydropentafluoropropene, 2-hydropentafluoropropene, dichlorodifluoroethylene, trifluoroethylene, 1,1-dichlorofluoroethylene, vinyl fluoride, and perfluoro-1,3-dioxoles, such as those described in U.S. Pat. No. 4,558,142 (Holland et al.). Certain fluorine-containing di-olefins also are useful, such as perfluorodiallylether and perfluoro-1,3-butadiene.

Fluorine-containing monomers also may be copolymerized with fluorine-free (preferably terminally unsaturated) olefinic comonomers, e.g., ethylene or propylene. Preferably at least 50% by weight of all monomers in a polymerizable mixture are fluorine-containing. Useful olefinically unsaturated monomers include alkylene monomers such as ethylene and propylene.

Examples of suitable VF$_2$-containing fluoropolymers are selected from the group consisting of tetrafluoroethylene/hexafluoropropylene/vinylidene fluoride terpolymer, polyvinylidene fluoride, vinylidene fluoride/hexafluoropropylene copolymer, vinylidene fluoride/tetrafluoroethylene copolymer, and mixtures thereof.

VF$_2$-containing polymers can be made by well-known conventional means, for example by free-radical polymerization of VF$_2$ with or without other ethylenically unsaturated monomers. The preparation of colloidal aqueous dispersions of such polymers and copolymers is described, for example, in U.S. Pat. No. 4,335,238 (Moore et al.). Other methods of preparing VF$_2$-containing fluoropolymer using emulsion polymerization techniques are described in U.S. Pat. No. 4,338,237 (Sulzbach et al.) or U.S. Pat. No. 5,285,002 (Grootaert).

Suitable VF$_2$-containing polymers are also commercially available. These include, for example, those commercially available under the trade designations THV (terpolymers of $CF_2=CF_2/CH_2=CF_2/CF_3CF=CF_2$ (TFE/VDF/HFP) available from Dyneon LLC of Oakdale, Minn.), KYNAR (VDF homopolymers and VDF copolymers available from Atofina), and FLUOREL (e.g., a copolymer of $CF_2=CH_2/CF_3CF=CF_2$ (VDF/HFP) available from Dyneon LLC). A preferred material is THV 220 fluoropolymer (Dyneon, Oakdale Minn.), which is a terpolymer of tetrafluoroethylene, hexafluoropropylene, and vinylidene fluoride made to 8% solids in methyl ethyl ketone.

Polyepoxides

Polyepoxides for use in the waveguide layer of the acoustic sensor described herein include a broad class of materials derived from a reactive resin containing an oxiranyl(epoxide) group. Polyepoxides are particularly desirable waveguides especially with the functionalized materials, particularly the functionalized soluble polymers, described herein in the immobilization overlayers.

Preferred polyepoxides suitable for use in the waveguide layer of the acoustic sensors described herein include polymers derived from an aromatic or cycloaliphatic diepoxide, more preferably, a diglycidyl ether of a bisphenol (e.g., having a molecular weight of about 350 to about 5000, preferably 350 to 600), and even more preferably a polymer of bisphenol A diepoxide.

A typical coating composition for preparing a polyepoxide waveguide includes one or more oxirane-functional resins, optionally includes non-reactive fillers (e.g., inorganic powders such as clay and talc), and also, includes a curative that is reactive with the oxirane group. Curatives that react with oxirane groups are well-known to those of skill in the art and include di- and poly-amines, di- and poly-thiols, di- and poly-phenols, di- and poly-anhydrides, di- and poly-carboxylic acids, imidazoles, imidizole metal complexes, as well as certain metal salts that initiate cationic polymerization.

Polyepoxide coatings useful as waveguides can be broadly classified by the methods by which the coating can be made storage stable. In one-part polyepoxide coatings, the curative is chosen such that it is insoluble under storage conditions but becomes soluble under cure conditions. One such curative is dicyandiamide. Alternatively, one may choose a curative whose curing reaction is initiated by light. One such material is diphenyliodonium hexafluorophosphate. Another method by which one achieves storage stability is to formulate a two-part epoxy coating. In this case, the oxirane functional resins are stored in separate containers from the curing agents. When cure is desired, the two-components are mixed in the appropriate proportions in order to initiate cure.

Another class of polyepoxides for use as waveguides, is represented by epoxy resists commonly used in the electronics industry. A common example of such a material is the SU8 resists available commercially from several sources (e.g., Microchem Corporation, Newton Mass.). The advantage of using this type of polyepoxide as a waveguide lies in its ability to be photo-patternable, allowing coating of the waveguide exactly where needed on the acoustic sensor. In addition such polyepoxides exhibit excellent adhesion to a variety of semiconductor and metal oxide surfaces.

A preferred polyepoxide is prepared from a 1 to 1, two part, room temperature curing epoxy including: a first part (Part A): bisphenol A diepoxide (Dow Chemical DER 317 Epoxy Resin) in a diluent (O-Cresyl Glycidyl Ether) in a 90/10 ratio; and a second part (Part B): an amine curative (Resolution Performance Products Epi-Cure 3251).

Styrene-containing Polymers

Styrene-containing polymers suitable for use in the waveguide layer of the acoustic sensors described herein include homopolymers, copolymers, etc., derived from styrene or a derivative thereof (e.g., alpha-methylstyrene, halostyrenes). Polystyrenes are known for use as waveguides in acoustic sensors (see, for example, D. W. Branch et al., Biosensors and Bioelectronics, 19, 849-859 (2004)).

The primary appeal of styrene-containing polymers, particularly polystyrenes, as waveguide materials comes from the low dielectric constants and power factors that these polymers possess, placing them in a class with polyolefins and fluorocarbons. Polystyrenes have excellent electrical insulating properties that are stable at a variety of frequencies and in the presence of moisture. As such, these characteristics make polystyrenes excellent materials for an acoustic waveguide since one of the primary functions of a good waveguide is to electrically isolate the electrode structures from a liquid environment. As a matter of fact, polystyrenes are widely used in many commercial applications where electrical insulation at high frequencies is necessary. A variety of polystyrenes with different molecular weights are available from many commercial sources (e.g., Scientific Polymer Products, Ontario, N.Y.).

A preferred example is the polystyrene available from Scientific Polymer Products (Ontario, N.Y.) (Mw=280 KDa). Other styrene-containing polymers include poly(styrene/MeFBSEMA/A174), which is a 47.5/47.5 copolymer of polystyrene and N-methyl perfluorobutanesulfonamidoethyl methacrylate, containing 5% of Silane-A174 ([3-(methacryloyloxy)propyl]trimethoxysilane from GSF Chemicals, Tullytown, Pa.).

Poly(N-vinylcarbazole)s

Another suitable material for use in the waveguide layer of the acoustic sensors described herein includes a polymer derived from N-vinylcarbazole and optionally other ethylenically unsaturated monomers, particularly poly(N-vinylcarbazole) (PVK).

Poly(N-vinylcarbazole) is best known for its photoconductive properties. It is used as an engineering plastic but it is most commonly employed as a hole transport layer in organic light emitting devices. As such it is often used doped with various dopants including iodine, TCNQ, TNF, etc. As an engineering plastic it has good mechanical and thermal properties that make it a candidate in aerospace applications. It is processable, very strong, and can have high glass-transition temperatures (e.g., greater than 200° C.). Because of its dielectric and mechanical properties, as well as its wide application in the optoelectronic industry where several processes for precision coating and patterning of this material have already been identified and employed, this polymer is a useful candidate for waveguide use in an acoustic sensor.

Another advantage of this polymer for use in an acoustic waveguide lies in the ability to easily copolymerize it with a variety of other ethylenically unsaturated monomers, in order to precisely tailor mechanical, acoustic, as well as adhesive properties of the waveguide. PVK is commercially available in a wide range of molecular weights from various sources. Preferred examples are those commercially available from Polymer Source (Montreal, Calif.) in two different molecular weights (58.6 KDa and 118 KDa).

Polyimides

Another suitable material for use in the waveguide layer of the acoustic sensors described herein includes a polyimide (PI). Polyimides are known for use as waveguides in acoustic sensors (see, for example, D. W. Branch et al., Biosensors and Bioelectronics, 19, 849-859 (2004)).

Polyimides are formed by reacting a dianhydride with a diamine. Diamines are aromatic and can range from methylene dianiline to diaminodiphenylether. The anhydrides can range from nadic anhydride to benzophenone tetracarboxylic acid dianhydride to 4,4'-hexafluoropropylidene-bis-9phthalic acid). A distinguishing feature in polyimide polymerization is the elimination of water in each polymerization step. Typically polymerization proceeds by the initial formation of a polyamic acid that is then imidized by curing at high temperatures, to form polyimide. Polyimide cure temperatures are usually above 220° C.

Polyimides particularly useful in the waveguide layer of the acoustic sensor are a class of polyimides that are typically used as resists in electronic applications. The feature that is appealing from this class of polyimides in waveguide use is the ability for some of these photoresists to be patternable by photolithographic techniques. This allows a convenient means to precisely place the waveguide layer exactly were needed on the acoustic sensor. Furthermore, these polymers also exhibit good adhesion to a variety of semiconductor and metal oxide surfaces. Examples of these types of polyimides are commercially available from HD MicroSystems (for example, HD Microsystems PI2600 series, particularly the polyimide that is commercially available under the trade designation PYRALIN PI2610).

Deposition Methods

As used with acoustic sensors, materials described herein may be deposited by any suitable technique or method. Typically, it may be preferred that such materials be delivered to a substrate in a carrier liquid, with the carrier liquid (e.g., ethyl acetate, propyl acetate, 2-butoxy ethyl acetate, toluene, N-methyl-2-pyrrolidone, 2-ethoxy ethyl acetate, butyl acetate, methyl ethyl ketone, ethanol, isopropyl alcohol, water, and mixtures thereof) and the materials forming, e.g., a solution or a dispersion. When so delivered, examples of some suitable deposition techniques for depositing the materials on a surface may include, but are not limited to, flood coating, spin coating, printing, non-contact depositing (e.g., ink jetting, spray jetting, etc.), chemical vapor deposition coating, pattern coating, knife coating, etc. It may be preferred, in some embodiments, that the deposition technique has the capability of pattern coating a surface, i.e., depositing the materials on only selected portions of a surface, such as the coating process described in U.S. Pat. No. 7,175,876.

A preferred process is a non-contact deposition process, particularly an aerosol jet deposition process (e.g., spray-jet or ink-jet) that is capable of depositing solutions or dispersions onto virtually any surface with feature sizes as small as 25 microns. The process is non-contact and conformal, allowing patterning over existing structures, across curved surfaces, and into channels or vias. During the deposition process, the liquid composition is atomized into droplets on the order of 1 micron in diameter; the droplets are then entrained in a gas stream. The entrained droplets are directed into the deposition head and an annular flow of inert gas compresses the stream to a diameter as small as 25 microns. An aerosol jet of droplets exits the deposition head at high velocity and is deposited on the target surface (substrate).

In some embodiments, the materials of the present invention may function as both waveguide material and immobilization material for secondary capture agents on an underlying substrate. In other embodiments, the materials of the present invention may function as waveguide material, immobilization material, and capture material. In both of these variations, the materials of the present invention will preferably be deposited on an underlying substrate that is, itself, effectively insoluble in the carrier liquid such that the carrier liquid does not adversely affect the underlying substrate.

If, however, the surface on which the materials of the present invention are to be deposited exhibits some solubility in the carrier liquid used to deliver the materials of the present invention, it may be preferred that the materials of the present invention be deposited using a non-contact deposition technique such as, e.g., ink jetting, spray jetting etc. For example, if the underlying substrate is a waveguide formed of, e.g., polyimide, etc., on a sensor substrate and a soluble polymer of the present invention is to be deposited using, e.g., butyl acetate, as the carrier liquid, then it may be preferred to use a non-contact deposition method to limit deformation of the waveguide layer and to preferably retain the functional characteristics of the materials of the present invention exposed on the resulting coated surface.

Figure 5:
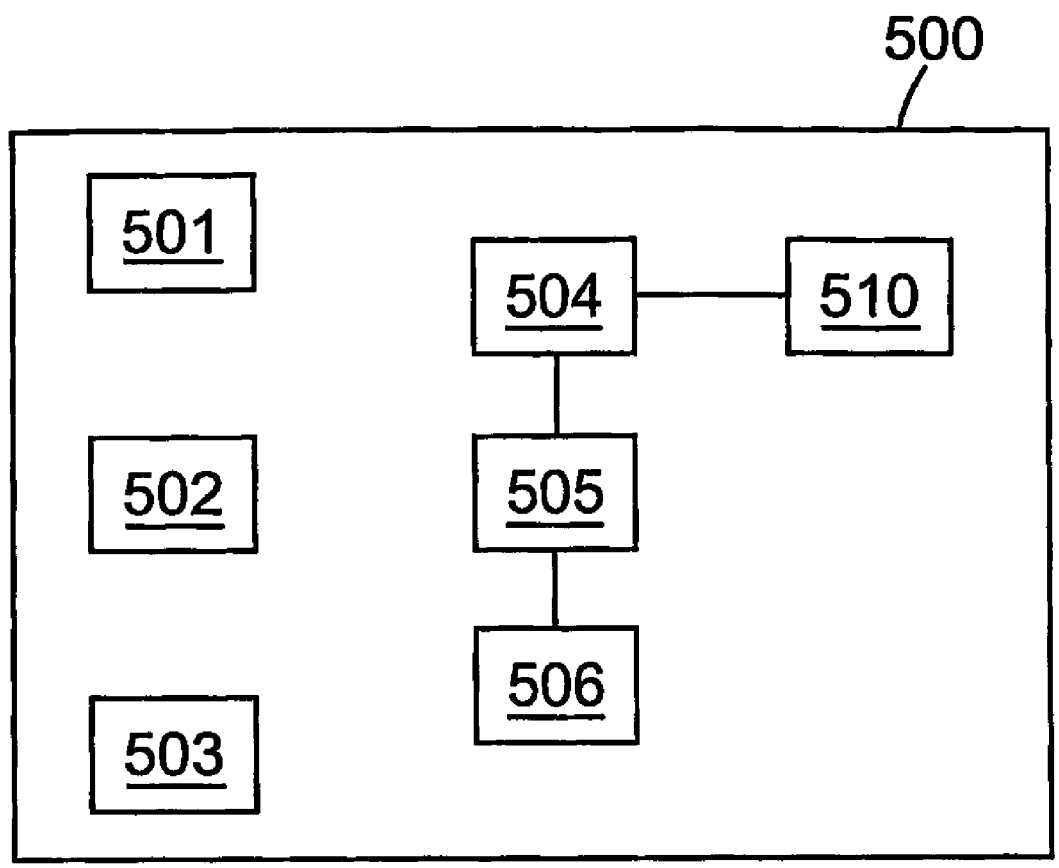
FIG. 5 is a schematic diagram of an acoustic sensor detection system.

There are several variables that may be controlled in an aerosol jet deposition process (e.g., a spray-jet coating process), including deposition rate, substrate speed (relative to the deposition head), sheath gas flow rate, sheath gas, raster spacing, raster pattern, number of passes, percent solids in the solution/dispersion, nozzle diameter, the carrier liquid, the composition of the underlying surface on which the materials of the present invention are being deposited, etc. Specific conditions under which the materials of the present invention can be deposited to yield a suitable coating may be determined empirically.

Detection Systems and Cartridges

As discussed herein, the materials and methods of the present invention may be used on sensors to provide waveguides, immobilization layers, capture materials, or combinations thereof. The following discussion presents some potential examples of systems and detection cartridges in which the sensors using the materials of the present invention may be used.

Additional discussion related to various detection systems and components (such as detection cartridges including biosensors) may be found in, e.g., U.S. Patent Application No. 60/533,169, filed Dec. 30, 2003; PCT Publication No. WO 2005/075973 entitled "Acousto-Mechanical Detection Systems and Methods Of Use," and PCT Publication No. WO 2005/064349 entitled "Detection Cartridges, Modules, Systems and Methods".

FIG. 2 is a schematic diagram of one detection apparatus including a biosensor. The depicted apparatus may include inputs such as a reagent 222, test specimen 224, and wash buffer 226. These various components may be introduced into, e.g., a staging chamber 228 where they may intermix and/or react with each other to form sample material that can be further processed. For example, it may be desirable that the reagent 222 and test specimen 224 be introduced into the staging chamber 228 to allow the reagent 222 to act on the test specimen 224 such that any target biological analyte within the test specimen 224 can be effectively modified. Alternatively, one or more these components may be present in the preparation chamber 228 before one or more of the other components are introduced therein.

It may be preferred that the reagent 222 be selective to the target biological analyte, i.e., that other biological analytes in the test specimen 224 are not modified by the reagent 222. Alternatively, the reagent 222 may be non-selective, i.e., it may act on a number of biological analytes in the test specimen 224, regardless of whether the biological analytes are the target biological analyte or not.

After delivery, the test specimen 224 and reagent 222 may be moved from the staging chamber 228 to the detection chamber 230 where the target biological analyte can contact the detection surface 232 of a sensor that may preferably be manufactured using the materials of the present invention. The detection surface 232 may preferably be of the type that includes capture agents located thereon such that the target biological analyte in the sample material is selectively attached to the detection surface 232.

After the target biological analytes in the sample material have been resident in the detection chamber 230 for a sufficient period of time or have moved therethrough, a wash buffer 226 may be introduced into the detection chamber 230 to remove unattached biological analytes and other materials from the detection chamber 230. These materials may preferably move into a waste chamber 236 connected to the detection chamber 230.

Detection of any target biological analytes selectively attached to the detection surface preferably occurs using the sensor 234 as operated by an optional control module 235. The control module 235 may preferably operate the sensor 234 such that the appropriate acousto-mechanical energy is generated and also monitor the sensor 234 such that a determination of the presence or absence of the target biological analyte on the detection surface 232 can be made.

Examples of techniques for driving and monitoring acousto-mechanical sensors such as those that may be used in connection with the present invention may be found in, e.g., U.S. Pat. No. 5,076,094 (Frye et al.); U.S. Pat. No. 5,117,146 (Martin et al.); U.S. Pat. No. 5,235,235 (Martin et al.); U.S. Pat. No. 5,151,110 (Bein et al.); U.S. Pat. No. 5,763,283 (Cernosek et al.); U.S. Pat. No. 5,814,525 (Renschler et al.); U.S. Pat. No. 5,836,203 ((Martin et al.); and U.S. Pat. No. 6,232,139 (Casalnuovo et al.), etc. Further examples may be described in, e.g., Branch et al., "Low-level detection of a *Bacillus anthracis* simulant using Love-wave biosensors on 36°YX $LiTaO_3$," Biosensors and Bioelectronics, 19, 849-859 (2004); as well as in U.S. Patent Application No. 60/533,177, filed on Dec. 30, 2003, and PCT Publication No. WO 2005/06622, entitled "Estimating Propagation Velocity Through A Surface Acoustic Wave Sensor".

An alternative exemplary detection apparatus is depicted in FIG. 3 with inputs that may optionally include a reagent 322, test specimen 324, wash buffer 326, and magnetic particles 327. These various components may be introduced into, e.g., a staging chamber 328 where they may intermix and/or react with each other. Alternatively, one or more these components may be present in the staging chamber 328 before one or more of the other components are introduced therein.

For example, it may be desirable that the reagent 322 and the test specimen 324 be introduced into the staging chamber 328 to allow the reagent 322 to act on and/or attach to the target biological analyte within the test specimen 324. Following that, the magnetic particles 327 may be introduced into the staging chamber 328. The magnetic particles 327 may preferably selectively attach to the target biological analyte material within the staging chamber 328, although they do not necessarily need to do so.

After attachment of the target biological analyte in the test specimen 324 to the magnetic particles 327, the test specimen 324 (and associated magnetic particles) may be moved from the staging chamber 328 to the detection chamber 330 where the target biological analyte in the sample material can contact the detection surface 332 of a sensor that may preferably be manufactured using the materials of the present invention.

If the target biological analyte is associated with magnetic particles, it may be desirable to include a magnetic device 333 capable of generating a magnetic field at the detection surface 332 such that the target biological analyte associated with magnetic particles can be magnetically drawn towards the detection surface for detection using sensor 334 operated by controller 335. The use of magnetic particles in connection with the target biological analyte may enhance detection by, e.g., moving the target biological analyte to the detection surface 332 more rapidly than might be expected in the absence of, e.g., magnetic attractive forces.

If the detection surface 332 includes selective capture agents located thereon such that the target biological analyte is selectively attached to the detection surface 332 in the absence of magnetic fields, then the magnetic particles that are not carrying (or being carried by) any target biological analyte can be removed from the detection surface 332 by, e.g., removing the magnetic field and washing the detection surface 332.

Although two exemplary detection apparatus that may be used in connection with the present invention are discussed above in connection with FIGS. 2 & 3, those apparatus may be contained in an integrated unit that may be described as a detection cartridge. Detection cartridges may, however, not include a controller 235/335 as described above, with control functions preferably being performed by an instrument to which the detection cartridge is operably connected as described below in connection with the system of FIG. 5.

Detection cartridges of the invention may preferably include an integrated sensor and fluid control features that assist in selective delivery of a sample material to the sensor. The exemplary detection cartridge 410 depicted schematically in FIG. 4 includes, among other things, a staging chamber 420, detection chamber 430, waste chamber 440, sensor 450, volumetric flow control feature 470, and modules 480. In general, the detection cartridge 410 of FIG. 4 may be described as having an interior volume that includes the staging chamber 420, detection chamber 430 and waste chamber 440, with the different chambers defining a downstream flow direction from the staging chamber 420 through the detection chamber 430 and into the waste chamber 440. Not every detection cartridge used in connection with the present invention may necessarily include the combination of components contained in detection cartridge 410 of FIG. 4.

The detection chamber 430 of the detection cartridge 410 preferably defines an interior volume between the detection surface of the sensor 450 and an opposing surface 460 located opposite from the detection surface of the sensor 450. The detection chamber 430 may preferably provide sidewalls or other structures that define the remainder of the interior volume of the detection chamber 430 (i.e., that portion of the detection chamber 430 that is not defined by the detection surface of the sensor 450 and the opposing surface 460).

Figure 4:
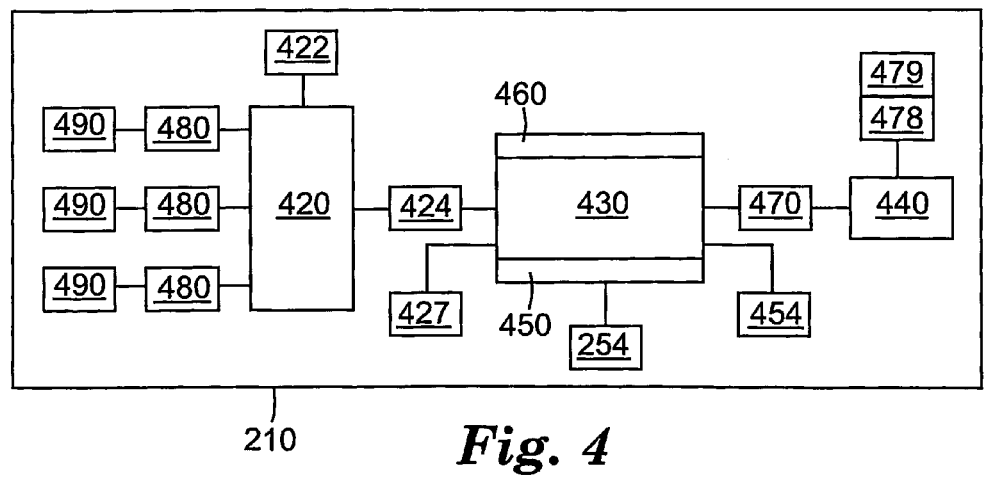
FIG. 4 is a schematic diagram of one exemplary detection cartridge.

Also depicted in FIG. 4 is a connector 454 that may preferably be operably connected to the sensor 450 to supply, e.g., power to the sensor 450. The connector 454 may also function to connect the sensor 450 to a controller or other system that may supply control signals to the sensor 450 or that may receive signals from the sensor 450. If necessary, the connector 454 (or additional connectors) may be operably connected to other components such as valves, fluid monitors, temperature control elements (to provide heating and/or cooling), temperature sensors, and other devices that may be included as a part of the detection cartridge 410.

In addition to the detection chamber 430, the detection cartridge 410 depicted in FIG. 4 also includes an optional waste chamber 440 into which material flows after leaving the detection chamber 430. The waste chamber 440 may be in fluid communication with the detection chamber 430 through a volumetric flow control feature 470 that can be used to control the rate at which sample material from the detection chamber 430 flows into the waste chamber 440. The volumetric flow control feature 470 may preferably assist in drawing fluid through the detection chamber 430 and move it into the waste chamber 440. In various exemplary embodiments as described herein, the volumetric flow control feature 470 may include one or more of the following components: one or more capillary channels, a porous membrane, absorbent material, a vacuum source, etc. These different components may, in various embodiments, limit or increase the flow rate depending on how and where they are deployed within the cartridge 410. For example, a capillary structure may be provided between the detection chamber 430 and the waste chamber 440 to limit flow from the detection chamber 430 into the waste chamber 440 if, e.g., the waste chamber 440 includes absorbent material that might cause excessively high flow rates in the absence of a capillary structure.

Another feature depicted in FIG. 4 is a vent 478 that may preferably be provided to place the interior volume of the detection cartridge 410 in fluid communication with the ambient atmosphere (i.e., the atmosphere in which the detection cartridge 410 is located) when the vent 478 is an open condition. The vent 478 may also preferably have a closed condition in which fluid flow through the vent 478 is substantially eliminated. Closure of the vent 478 may, in some embodiments, effectively halt or stop fluid flow through the interior volume of the detection cartridge 410. Although depicted as leading into the waste chamber 440, one or more vents may be provided and they may be directly connected to any suitable location within the detection cartridge 410, e.g., staging chamber 420, detection chamber 430, etc. The vent 478 may take any suitable form, e.g., one or more voids, tubes, fittings, etc.

The vent 478 may include a closure element 479 in the form of a seal, cap, valve, stopper, or other structure(s) to open, close or adjust the size of the vent opening. In some embodiments, the closure element 479 may be used to either open or close the vent. In other embodiments, the closure element 479 may be adjustable such that the size of the vent opening may be adjusted to at least one size between fully closed and fully open to adjust fluid flow rate through the detection cartridge 410. For example, increasing the size of the vent opening may increase fluid flow rate while restricting the size of the vent opening may cause a controllable reduction the fluid flow rate through the interior volume of the detection cartridge 410, e.g., through the staging chamber 420, detection chamber 430, etc. If the vent 478 includes multiple orifices, one or more of the orifices can be opened or closed by the closure element(s) 479, etc.

Although the volumetric flow rate of fluid moving through the detection chamber 430 may be controlled by the volumetric flow control feature 470, it may be preferred to provide for control over the flow front progression through the detection chamber 430. Flow front progression control may assist in ensuring that all portions of a detection surface of the sensor 450 exposed within the detection chamber 430 are covered or wetted out by the fluid of the sample material such that bubbles or voids are not formed. It may be preferred for example that the flow front progress through the detection chamber 430 in the form of a generally straight line that is oriented perpendicular to the direction of flow through the detection chamber 430.

In the exemplary embodiment depicted in FIG. 4, the flow front control features may preferably be provided in or on the opposing surface 460. This may be particularly true if the sensor 450 relies on physical properties that may be affected by the shape and/or composition of the detection surface, e.g., if the detection surface is part of a sensor that relies on acoustic energy transmission through a waveguide that forms the detection surface or that lies underneath the detection surface. Discontinuities in physical structures or different materials arranged over the detection surface may, e.g., cause the acoustic energy to propagate over the detection surface in a manner that is not conducive to accurate detection of a target analyte within the detection chamber 430.

The flow front control features provided on the opposing surface 460 may preferably be passive, i.e., they do not require any external input or energy to operate while the fluid is moving through the detection chamber 430. The flow front control features may also preferably operate over a wide range of sample volumes that may pass through the detection chamber 430 (e.g., small sample volumes in the range of 10 microliters or less up to larger sample volumes of 5 milliliters or more).

It may be preferred that the opposing surface 460 and the detection surface of the sensor 450 be spaced apart from each other such that the opposing surface 460 (and any features located thereon) does not contact the detection surface of the sensor 450. With respect to acoustic sensors, even close proximity of the opposing surface 460 to the detection surface of the sensor may adversely affect the properties of the sensor operation. It may be preferred, for example, that spacing between the detection surface of the sensor 450 and the lowermost feature of the opposing surface 460 be 20 micrometers or more, or even more preferably 50 micrometers or more. For effective flow front control, it may be preferred that the distance between the lowermost feature of the opposing surface 460 and the detection surface of the sensor 450 be 10 millimeters or less, more preferably 1 millimeter or less, and more preferably 250 micrometers or less.

In one class of flow front control features, the opposing surface 460 may include physical structure such as channels, posts, etc. that may be used to control the flow of fluid through the detection chamber 430. Regardless of the particular physical structure, it is preferably of a large enough scale such that flow front progression through the detection chamber is meaningfully affected. Examples of suitable physical structures may include, e.g., multiple discrete structures in the form of posts, embedded or attached beads, etc., dispersed over the opposing surface and protruding from the land area that separates the discrete structures. If the physical structure includes channels formed in the opposing surface, the channels may preferably be straight channels arranged parallel to each other and be oriented perpendicular to the desired fluid flow direction. The channels may be irregularly sized, irregularly shaped, irregularly spaced, straight, curved, oriented at other than a ninety degree angle to fluid flow, etc. Adjacent channels may be immediately adjacent each other or they may be separated by land areas on the opposing surface. The channels may have any cross-sectional shape, e.g., triangular, arcuate, rectangular, trapezoidal, hemispherical, etc. and combinations thereof.

In some embodiments, flow front progression control may be accomplished through the use of hydrophilic and/or hydrophobic materials located on the opposing surface 460 (in the absence of or in combination with physical structures). For example, the opposing surface 460 may include regions of hydrophobic materials and regions of hydrophilic materials occupying portions of the opposing surface 460. The regions may preferably be provided as successive bands oriented generally perpendicular to the direction of flow through the detection chamber (although other hydrophilic/hydrophobic patterns may be used). The hydrophilic and/or hydrophobic materials used in the regions may be coated or otherwise provided on the opposing surface 460.

The optional staging chamber 420 depicted in FIG. 4 may be used to stage, mix or otherwise hold sample material before its introduction to the detection chamber 430. The staging chamber 420 may take any suitable form. In some instances, it may be preferred that the volume of the staging chamber 420 be located above (relative to gravitational forces) the detection chamber 430 during use of the cartridge 410 such that static head can be developed within the sample material in the staging chamber 420 that can assist its passive delivery to the detection chamber 430 from the staging chamber 420.

An optional port 422 may be provided in the staging chamber 420 (or in another location that leads to the interior of the cartridge 410) such that material may be introduced into the interior volume of the cartridge 410 by, e.g., by syringe, pipette, etc. If provided, the port 422 may be sealed by, e.g., a septum, a valve, and/or other structure before and/or after materials are inserted into the cartridge 410. In some embodiments, the port 422 may preferably include, e.g., an external structure designed to mate with a test sample delivery device, e.g., a Luer lock fitting, threaded fitting, etc. Although only one port 422 is depicted, it should be understood that two or more separate ports may be provided.

In some embodiments, the staging chamber 420 may be isolated from direct fluid communication with the detection chamber 430 by a flow control structure/mechanism 424 (e.g., a valve, etc.). If a flow control structure/mechanism 424 is provided to isolate the detection chamber 430 from the staging chamber 420, then the staging chamber 420 may potentially be more effectively used to store materials before releasing them into the detection chamber 430. In the absence of a flow control structure/mechanism 424, some control over the flow of materials into the detection chamber 430 may potentially be obtained by other techniques, e.g., holding the cartridge 410 in an orientation in which the force of gravity, centripetal forces, etc. may help to retain materials in the staging chamber 420 until their delivery to the detection chamber 430 is desired.

Another optional feature depicted in FIG. 4 is the inclusion of a fluid monitor 427. The fluid monitor 427 may preferably provide for active, real-time monitoring of fluid presence, flow velocity, flow rate, etc. The fluid monitor 427 may take any suitable form, e.g., electrodes exposed to the fluid and monitored using e.g., alternating currents to determine flow characteristics and/or the presence of fluid on the monitors electrodes. Another alternative may involve a capacitance based fluid monitor that need not necessarily be in contact with the fluid being monitored.

Although depicted as monitoring the detection chamber 430, it should be understood that the fluid monitor may be located at any suitable location within the interior volume of the detection cartridge 410. For example, the fluid monitor could be located in the staging chamber 420, the waste chamber 440, etc. In addition, multiple fluid monitors may be employed at different locations within the cartridge 410.

Potential advantages of the fluid monitor 427 may include, e.g., the ability to automatically activate the introduction of sample materials, reagents, wash buffers, etc. in response to conditions sensed by the fluid monitor 427 that are employed in a feedback loop to, e.g., operate actuators 490 associated with modules 480, etc. Alternatively, the conditions sensed by the fluid monitor 427 can provide signals or feedback to a human operator for evaluation and/or action. For some applications, e.g., diagnostic healthcare applications, the fluid monitor 427 may be used to ensure that the detection cartridge is operating properly, i.e., receiving fluid within acceptable parameters.

Also depicted in FIG. 4 are optional modules 480 that may preferably be used to introduce or deliver materials into the cartridge 410 in addition to or in place of ports 422. It may be preferred, as depicted, that the modules 480 deliver materials into the staging chamber 420, although in some instances, they could potentially deliver materials directly into the detection chamber 430. The modules 480 may be used to deliver a wide variety of materials, although it may be preferred that the delivered materials include at least one liquid component to assist in movement of the materials from the module 480 and into the cartridge 410. Among the materials that could be introduced using modules 480 are, e.g., test specimens, reagents, buffers, wash materials, etc. Control over the introduction of materials from the modules 480 into the cartridge 410 may be obtained in a number of manners, e.g., the modules 480 may be isolated from the cartridge 410 by a seal, valve, etc. that can be opened to permit materials in the modules 480 to enter the cartridge 410.

It may be preferred that the modules 480 be independent of each other such that the materials contained within each module 480 can be introduced into the detection cartridge at selected times, at selected rates, in selected orders, etc. In some instances an actuator 490 may be associated with each module 480 to move the materials within the module 480 into the cartridge 410. The actuators 490 may be selected based on the design of the module 480. The actuators 490 may be manually operated or they may be automated using, e.g., hydraulics, pneumatics, solenoids, stepper motors, etc. Although depicted as a component of the detection cartridge 410, the actuators 490 may be provided as a part of the larger systems in which the cartridge is used as discussed herein.

System Design

Figure 2:
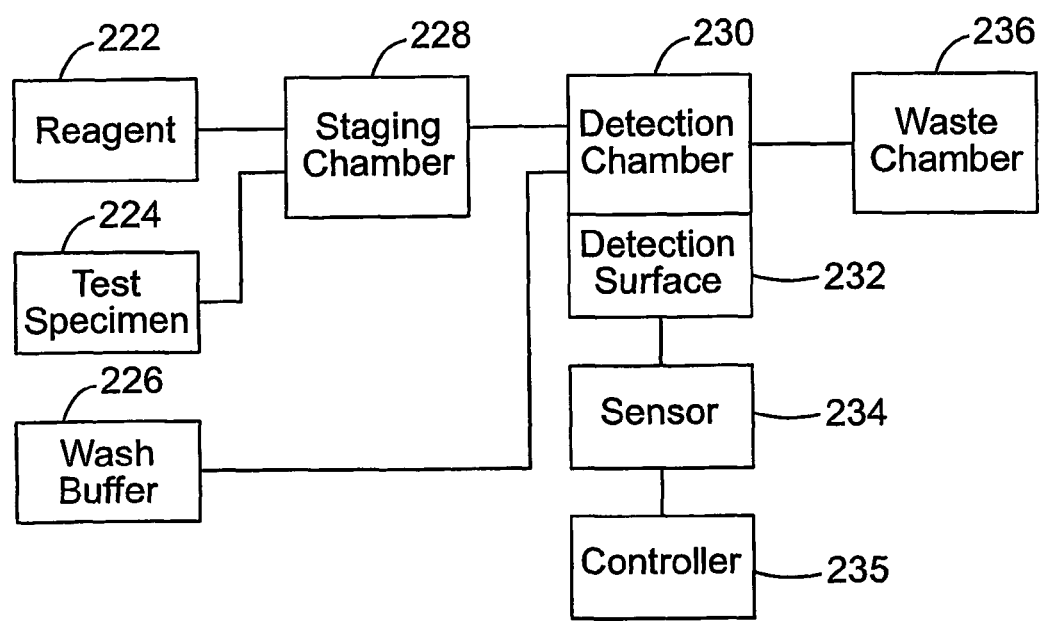
FIG. 2 is a schematic diagram of one exemplary detection apparatus including a biosensor.
Figure 3:
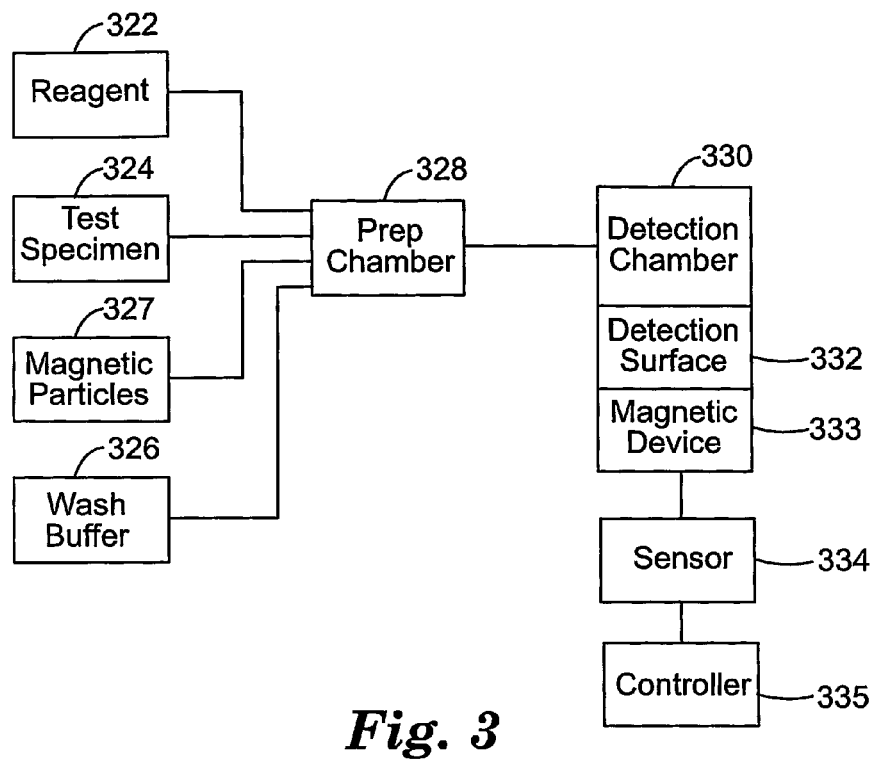
FIG. 3 is a schematic diagram of an alternative detection apparatus.

It may be desirable that the detection apparatus of FIGS. 2 & 3 be implemented in a detection cartridge as described in connection with FIG. 4. Regardless of their specific implementation however, the detection apparatus/cartridges may preferably be capable of docking with or being connected to an instrument that may, e.g., provide a variety of functions such as providing power to the sensors or other devices in the detection cartridge, accepting data generated by the sensor, providing the ability to take user input to control fluid flow and/or sensor operation, etc.

One such system 500 is schematically depicted in FIG. 5, and may preferably include a power source 501 and user interface 502 (e.g., pushbuttons, keyboard, touchscreen, microphone, etc.). The system 500 may also include an identification module 503 adapted to identify a particular detection system/cartridge 510 using, e.g., barcodes, radio-frequency identification devices, mechanical structures, etc.

The system 500 may also preferably include a sensor analyzer 504 that obtains data from a sensor in the detection cartridge and a processor 505 to interpret the output of the sensor. In other words, sensor analyzer 504 may receive output from a sensor detection cartridge 510 and provide input to processor 505 so that the output of the sensor can be interpreted.

Processor 505 receives input from sensor analyzer 504, which may include, e.g., measurements associated with wave propagation through or over an acousto-mechanical sensor. Processor 505 may then determine whether a target biological analyte is present in sample material. Although the invention is not limited in this respect, the sensor in detection cartridge 510 may be electrically coupled to sensor analyzer 504 via insertion of the detection cartridge 510 into a slot or other docking structure in or on system 500. Processor 505 may be housed in the same unit as sensor analyzer 504 or may be part of a separate unit or separate computer.

Processor 505 may also be coupled to memory 506, which can store one or more different data analysis techniques. Alternatively, any desired data analysis techniques may be designed as, e.g., hardware, within processor 505. In any case, processor 505 executes the data analysis technique to determine whether a detectable amount of a target biological analyte is present on the detection surface of a sensor in detection cartridge 510.

By way of example, processor 505 may be a general-purpose microprocessor that executes software stored in memory 506. In that case, processor 505 may be housed in a specifically designed computer, a general purpose personal computer, workstation, handheld computer, laptop computer, or the like. Alternatively, processor 505 may be an application specific integrated circuit (ASIC) or other specifically designed processor. In any case, processor 505 preferably executes any desired data analysis technique or techniques to determine whether a target biological analyte is present within a test sample.

Memory 506 is one example of a computer readable medium that stores processor executable software instructions that can be applied by processor 505. By way of example, memory 506 may be random access memory (RAM), read-only memory (ROM), non-volatile random access memory (NVRAM), electrically erasable programmable read-only memory (EEPROM), flash memory, or the like. Any data analysis techniques may form part of a larger software program used for analysis of the output of a sensor (e.g., LABVIEW software from National Instruments Corporation, Austin, Tex.).

Further descriptions of systems and data analysis techniques that may be used in connection with the present invention may be described in, e.g., U.S. Patent Application No. 60/533,177, filed on Dec. 30, 2003, and PCT Publication No. WO2005/06622, entitled "Estimating Propagation Velocity Through A Surface Acoustic Wave Sensor". Other data analysis techniques to determine the presence (or absence) of target biological analytes using sensors of the invention may also be used, e.g., time domain gating used as a post-experiment noise reduction filter to simplify phase shift calculations, etc. Still other potentially useful data analysis techniques may be described in the documents identified herein relating to the use of acoustic sensors. Although systems and methods related to the use of surface acoustic wave sensors are described therein, it should be understood that the use of these systems and methods may be used with other acousto-mechanical sensors as well.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

| Table of Abbreviations | |
|---|---|
| Abbreviation or Trade Designation | Description |
| VAZO 67 | 2,2'-Azobis(2-methlbutyronitrile), commercially available from DuPont Chemical Company, Wilmington, DE |
| EtOAc | Ethyl acetate |
| ACN | Acetonitrile |
| IPA | Isopropyl alcohol |
| DMF | Dimethylformamide |
| PEG 3400 | Poly(ethylene glycol) Mn (number average molecular weight) of approximately 3400 |
| PEG 1000 | Poly(ethylene glycol) Mn approximately 1000 |
| PEG 600 diacid | Poly(ethylene glycol) bis(carboxymethyl) ether) $HO_2CCH_2(OC_2H_4)_nOCH_2COOH$ Mn approximately 600 commercially available from Fluka Holding AG, Buchs, Switzerland |
| NMP | N-methylpyrrolidinone |
| TEA | Triethylamine |
| TPEG 990 | A glycerin-started trifunctional polyethylene glycol Mn approximately 990 commercially available from Dow Chemical Company, Midland, MI |
| THF | Tetrahydrofuran |
| Na saccharin | Sodium salt of saccharin, dehydrated |

Preparative Example M1

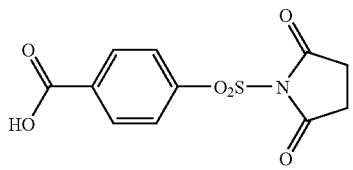

In a glass reaction vessel, a mixture of DMF (154 milliliters), 4-carboxybenzenesulfonamide (30.0 grams), succinic anhydride (16.41 grams), and triethylamine (33.19 grams) was stirred and heated to 50° C. under a nitrogen atmosphere for four hours. The mixture was allowed to cool to room temperature, acetic anhydride (18.27 milliliters) was added and the mixture was stirred at room temperature for an additional three hours. The mixture was poured into 400 milliliters of stirred 1N aqueous HCl. This mixture was filtered, washed with deionized water and dried in a vacuum oven to afford the desired product. Yield: 36.94 grams.

Preparative Example M2

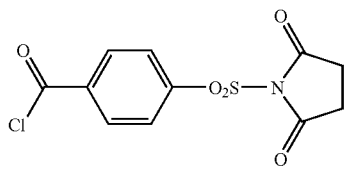

In a glass reaction vessel containing a stirred mixture of the carboxy-containing product of Preparative Example M1 (20.0 grams) and dry acetonitrile (85 grams) was added thionyl chloride (10.0 grams) and DMF (1 drop). The resulting mixture was stirred and heated under reflux for one hour, cooled to room temperature and further cooled in an ice bath, which resulted in the formation of a solid precipitate. The solid was collected by filtration, washed sequentially with cold acetonitrile and cold toluene, and dried overnight in a vacuum oven at 50° C. to give the desired product. Yield: 17.7 grams.

Preparative Example M3

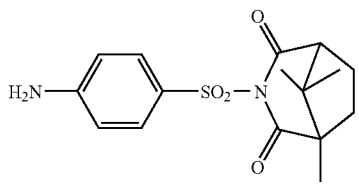

In a glass reaction vessel fitted with a reflux condenser, a thermometer, a pressure-equalizing addition funnel, and a nitrogen inlet was placed a 60 weight percent dispersion of NaH in mineral oil (22.52 grams). The dispersion washed three times with heptane by stirring the mixture for several minutes, allowing the mixture to stand, and using a pipette to decant the supernatant heptane. NMP (32 grams) was added to the flask and the mixture was stirred. To this stirred mixture was added a solution of camphoric anhydride (11.7 grams), sulfanilamide (10 grams), and NMP (50 grams) slowly via the addition funnel. The resulting mixture was stirred at room temperature for 24 hours, combined with 0.1N aqueous HCl and extracted with ethyl acetate. The extract was dried over $MgSO_4$ and the volatile components were removed using a rotary evaporator. In a glass reaction vessel this intermediate material was combined with methanesulfonyl chloride (6.98 grams), triethylamine (13.51 grams), and DMF (82.4 grams) and the resulting mixture was stirred for 1 hour at 60° C. The mixture was poured into aqueous 1N HCl and the resultant solid was isolated by filtration and recrystallized from methanol to give the desired product. Yield: 3 grams.

Preparative Example M4

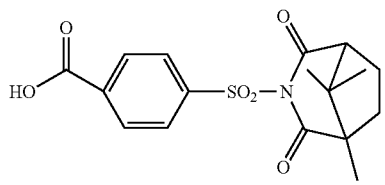

A glass reaction vessel fitted with a reflux condenser and magnetic stir bar was charged with trimethyl orthoformate (34.28 grams), 4-carboxybenzenesulfonamide (50.00 grams), toluenesulfonic acid (2.5 grams) and methanol (197 mL). The mixture was heated to 70° C. for 16 hours. The cooled mixture was concentrated on a rotary evaporator. Diethyl ether (200 mL) was added to the concentrate and stirred. The resulting solid was filtered to afford 51.3 grams of the desired 4-methoxycarbonylbenzenesulfonamide. In a glass reaction vessel fitted with a reflux condenser, a thermometer, a pressure-equalizing addition funnel, and a nitrogen inlet was placed a 60 weight percent dispersion of NaH in mineral oil (16.22 grams). The dispersion washed three times with heptane by stirring the mixture for several minutes, allowing the mixture to stand, and using a pipette to decant the supernatant heptane. NMP (50 grams) was added to the flask and the mixture was stirred. To this stirred mixture was added a solution of camphoric anhydride (14 grams), 4-methoxycarbonyl benzenesulfonamide (15 grams), and NMP (61 grams) slowly via the addition funnel. The resulting mixture was stirred at room temperature for approximately 1 hour, poured into a beaker of deionized water that was vigorously stirred. The basic mixture was acidified with 1.0N HCl and subsequently extracted with EtOAc. The volatile components were removed using a rotary evaporator to afford a solid intermediate. This intermediate was combined with THF (111 grams), acetic anhydride (8.54 grams), and triethylamine (23.3 grams) and stirred for 1 hour at 60° C. The mixture was poured into aqueous 1N HCl and the resultant solid isolated by filtration. The solid was combined with methanol and this mixture was heated to boiling, cooled to room temperature, filtered, and washed sequentially with methanol and diethyl ether. The solid was dried overnight in a vacuum oven at room temperature and 67 Pa (0.5 mm Hg) to give the desired product.

Preparative Example M5

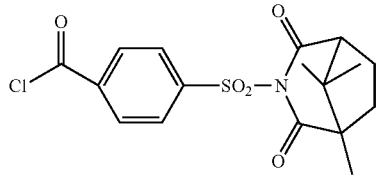

In a glass reaction vessel fitted with a reflux condenser, a thermometer, and a nitrogen inlet was placed the carboxylic acid product of Preparative Example M4 and ACN (20 grams). The flask was placed in an ice bath and a 20 weight percent solution of phosgene in toluene (15.57 grams) that was obtained from Fluka Holding AG, Buchs, Switzerland was added slowly via syringe. The mixture was allowed to warm to room temperature and heated at reflux. Periodically, the atmosphere above the reaction mixture was tested for the presence of phosgene using phosgene indicator paper. When no phosgene could be detected in this way, the flask was fitted with a distillation head and a small amount of the volatile materials were distilled away. The mixture was filtered and the solid was dried under a stream of nitrogen gas to give the desired product.

Preparative Example M6

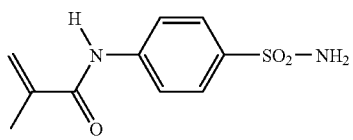

In a glass reaction vessel, to a solution of sulfanilamide (10.75 grams) in THF (85.4 milliliters) was added pyridine (5.93 grams) and the flask was chilled in an ice bath. Methacrylic anhydride (10.59 grams) was added and the mixture was stirred overnight while warming to room temperature. The reaction mixture was filtered and dried in a vacuum oven at room temperature overnight at 133.3 Pa (1 mm Hg) to give the desired product. Yield: 8.4 grams.

Preparative Example M7

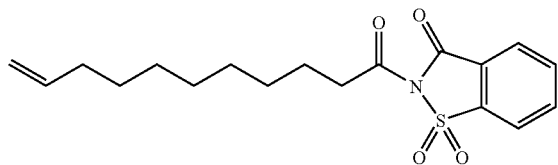

A mixture of 2,3-dihydro-3-oxobenzisosulfonazole (5.0 grams (g)), triethylamine (3.3 g) and acetonitrile (30 g) in a round bottom flask was magnetically stirred under a nitrogen atmosphere and was cooled in an ice bath. A solution of 10-undecenoyl chloride (6.1 g) in THF (12 g) was slowly added to the flask using a pressure-equalizing addition funnel. The mixture was allowed to warm to room temperature and was then filtered. The filtrate was concentrated to dryness using a rotary evaporator and the residue was triturated with diethyl ether. The resultant solid was ether. The resultant solid was filtered, washed with diethyl ether, and dried in air at room temperature to afford 8.7 g of product.

Preparative Example M8

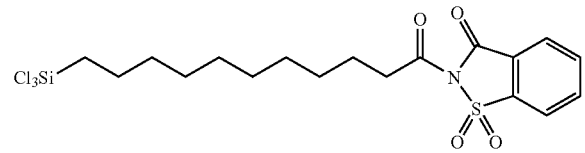

A mixture of the ethylenically unsaturated containing product of Example 9 (4.0 g), trichlorosilane (3.1 g), and methylene chloride (25 g) was combined in a 125 mL screw cap bottle. Platinum(0)-1,3-divinyl-1,1,3,3-tetramethyldisilane complex in xylenes was diluted with methylene chloride to a concentration of approximately 1.5 weight percent, and 3 drops of this solution were added to the bottle. The bottle was then sealed and was heated to 60° C. in a water bath. After 18 hours, the mixture was allowed to cool to room temperature and additional platinum complex solution (1 drop) was added. The bottle was again sealed and was heated at 60° C. for an additional 24 hours. The mixture was then cooled to room temperature and the volatile components were removed using a rotary evaporator.

Preparative Example N11

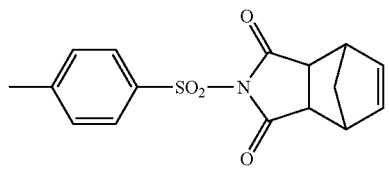

In a glass reaction vessel fitted with a pressure-equalizing addition funnel and a nitrogen inlet was placed a 60 weight percent dispersion of NaH in mineral oil (9.45 grams) and hexane (20 milliliters). The mixture was stirred for approximately 15 minutes and DMF (100 milliliters) was added. A mixture of p-toluenesulfonamide (15.7 grams) and 5-norbornene-2,3-dicarboxylic anhydride (16.2 grams) in DMF (100 milliliters) was slowly added to the flask via the addition funnel. The resulting mixture was allowed to stir overnight at room temperature. A solution of 5-norbornene-2,3-dicarboxylic anhydride (1.6 grams) in DMF (10 milliliters) was added drop wise to the flask and the mixture was stirred for approximately 6 hours. Acetic anhydride (28.14 grams) was added to the flask and the mixture was stirred overnight. Aqueous NaHCO₃ solution was added, followed by aqueous HCl. The mixture was filtered and the filtered solid was dried overnight using a vacuum oven and recrystallized from methanol to give the desired product. Yield: 14.8 grams.

Preparative Example MP2

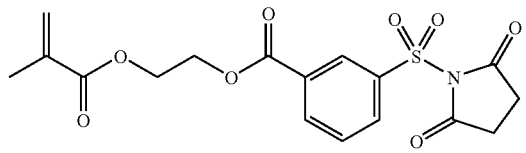

In a glass reaction vessel a mixture of NMP (9.11 milliliters), 2-hydroxyethyl methacrylate (0.78 grams) and a sample of the carbonyl chloride product of Preparative Example M2 (1.50 grams) were combined and stirred overnight at room temperature. The mixture was poured into 0.1N HCl and the resultant solid was collected by filtration, washed with deionized water, and dried in a vacuum oven at room temperature overnight at 133.3 Pa (1 mm Hg) to give the desired product. Yield: 1.53 grams.

Preparative Example MP3

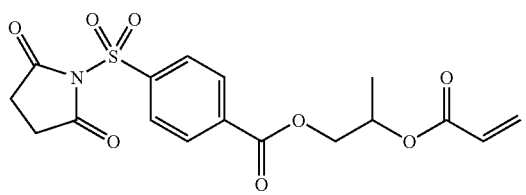

In a glass reaction vessel under a nitrogen atmosphere and chilled with an ice bath was placed a solution of a sample of the carbonyl chloride product of Preparative Example M2 (4.58 grams) in ACN (6.6 grams). To this stirred solution was added a solution of 2-hydroxypropyl acrylate (2.07 grams), triethylamine (1.69 grams) in ACN (20.0 grams). The mixture was stirred for overnight and allowed to warm to room temperature. The mixture was poured into 0.1N aqueous HCl and the resultant solid was collected by filtration, washed with deionized water, and dried in a vacuum oven at room temperature overnight at 133.3 Pa (1 mm Hg) to give the desired product.

Preparative Example MP4

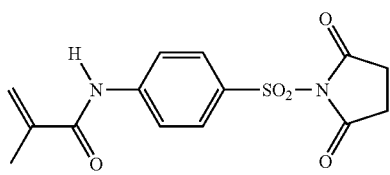

In a glass reaction vessel fitted with a reflux condenser was placed a solution of a sample of the product of Preparative Example M6 (6.00 grams) succinic anhydride (2.75 grams), triethyl amine (3.34 grams) in ACN (40 milliliters) with a trace of phenothiazine. This mixture was refluxed for 6 hours, cooled to room temperature, succinic anhydride (3.25 grams) and triethyl amine (6.11 grams) were added and the mixture was refluxed for 1 hour. The mixture was poured into 0.1N aqueous HCl and the resultant solid was collected by filtration, washed with deionized water, and dried in a vacuum oven at room temperature overnight at 133.3 Pa (1 mm Hg) to give the desired product. Yield: 5.9 grams.

Preparative Example MP5

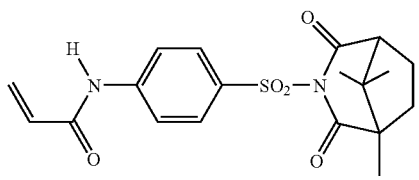

In a glass reaction vessel under a nitrogen atmosphere and chilled with an ice bath was added a solution of the product of Preparative Example M3 (1.20 grams) and pyridine (0.34 grams) in dry THF (4.3 grams) slowly to a solution of acryloyl chloride (0.39 grams) in dry THF (2.0 grams). The mixture was stirred overnight and allowed to warm to room temperature. The solvent was partially removed using a rotary evaporator. The mixture was poured into 0.01N aqueous HCl and the resultant solid was collected by filtration, washed with deionized water, and dried in a vacuum oven at room temperature overnight at 133.3 Pa (1 mm Hg) to give the desired product. Yield: 0.80 grams.

Preparative Example MP6

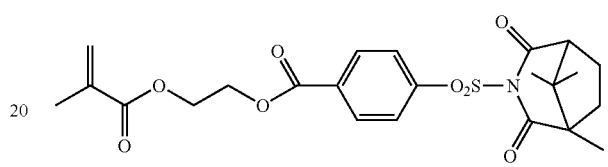

In a glass reaction vessel a solution of 2-hydroxyethyl methacrylate (0.68 grams) and a sample of the carbonyl chloride product of Preparative Example M5 (1.68 grams) in NMP (9.45 milliliters) was stirred overnight at room temperature. The mixture was poured into aqueous 0.1N HCl and extracted with ethyl acetate. The organic phase washed successively with deionized water and saturated aqueous NaCl and dried over MgSO$_4$. The solution was concentrated using a rotary evaporator and dried overnight in a vacuum oven at room temperature and 67 Pa (0.5 mm Hg) to give the desired product. Yield: 1.8 grams.

Preparative Example MP7

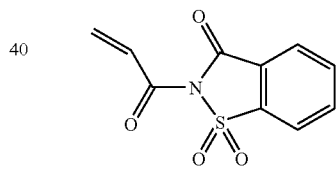

In a glass reaction vessel was placed a slurry of Na saccharin (dried by azeotroping with toluene) (20.5 grams) in acetone (150 milliliters). To this stirred slurry was added acryloyl chloride (9.2 grams) and the resulting mixture was stirred for 24 hours. The mixture was filtered and the solvent was removed to give 18.3 grams of insoluble and 9.5 grams of soluble white solids which were identical by IR spectroscopy. The soluble and insoluble solids were recombined in 400 milliliters of water, filtered and dried to give the desired product with about 80% purity by NMR. Yield: 20.5 grams. The solid was slightly soluble in EtOAc and soluble in NMP.

Preparative Example MP8

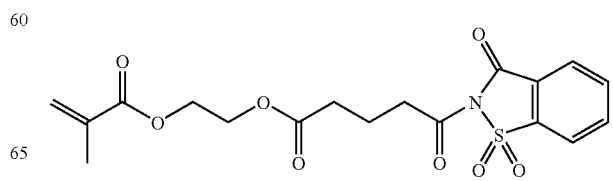

In a glass reaction vessel a solution of 2-hydroxyethyl methacrylate (22.31 grams), glutaric anhydride (20.54 grams) and triethyl amine (19.08 grams) in dry THF (167.5 milliliters) were stirred overnight at room temperature. The solution was concentrated using a rotary evaporator and the residue was dissolved in 400 milliliters of EtOAc. The organic phase washed successively with deionized water, saturated aqueous NaCl and dried over $MgSO_4$. The solution was filtered, treated with thionyl chloride (21.14 grams) and DMF (3 drops) in a glass reaction vessel. The mixture was stirred overnight and concentrated on a rotary evaporator. The concentrate was slowly added to a stirred suspension of dry Na saccharin (31.29 grams) in dry acetone (250 milliliters) chilled in an ice bath. The mixture was stirred overnight and allowed to warm to room temperature. The mixture was filtered, the filtrate was concentrated and slurried in chloroform, and filtered again. The filtrate was concentrated, diethyl ether was added and the precipitate was isolated by filtration and dried under a stream of nitrogen gas to give the desired product. Yield: 40.5 grams.

Preparative Example MP9

In a glass bottle, 1.0 gram of the product of Preparative Example MP2, 8.0 grams of methyl methacrylate, 1.0 gram of 3-methacryloxypropyl trimethoxysilane, and grams of EtOAc were mixed. To this mixture, 102 milligrams of VAZO 67 was added. The bottle was made inert with nitrogen gas and sealed. The sealed bottle was tumbled in a 60° C. water bath for 24 hours.

Preparative Example MP10

In a glass bottle, 1.0 gram of the product of Preparative Example MP2, 3.5 grams of methyl methacrylate, 0.5 grams of 3-methacryloxypropyl trimethoxysilane, 0.8 grams of 3-mercaptopropyl trimethoxysilane, and 20 grams of EtOAc were mixed. To this mixture, 100 milligrams of VAZO 67 was added. The bottle was made inert with nitrogen gas and sealed. The sealed bottle was tumbled in a 60° C. water bath for 24 hours.

Preparative Example MP11

In a glass bottle, 1.0 gram of the product of Preparative Example MP2, 2.0 grams of methyl methacrylate, 0.5 grams of 3-mercaptopropyl trimethoxysilane, and 20 grams of EtOAc were mixed. To this mixture, 101 milligrams of VAZO 67 was added. The bottle was made inert with nitrogen gas and sealed. The sealed bottle was tumbled in a 60° C. water bath for 24 hours.

Preparative Example MP12

In a glass bottle, 2.0 grams of the product of Preparative Example MP7, 8.0 grams of methyl acrylate, 10 grams of N-methylpyrrolidone, and 20 grams of EtOAc were mixed. To this mixture, 70 milligrams of VAZO 67 was added. The bottle was made inert with nitrogen gas and sealed. The sealed bottle was tumbled in a 60° C. water bath for 24 hours.

Preparative Example MP13

In a glass bottle, 2.0 grams of the product of Preparative Example MP7, 8.0 grams of methyl acrylate, and 10 grams of NMP were mixed. To this mixture, 70 milligrams of VAZO 67 was added. The bottle was made inert with nitrogen gas and sealed. The sealed bottle was tumbled in a 60° C. water bath for 24 hours.

Preparative Example MP14

In a glass bottle, 2.0 grams of the product of Preparative Example MP7, 8.0 grams of methyl methacrylate, and 20 grams of NMP were mixed. To this mixture, 65 milligrams of VAZO 67 was added. The bottle was made inert with nitrogen gas and sealed. The sealed bottle was tumbled in a 60° C. water bath for 24 hours.

Preparative Example MP15

In a glass bottle, 1.0 gram of the product of Preparative Example MP2, 8.0 grams of methyl methacrylate, 1.0 grams of 3-methacryloxypropyltrimethoxysilane and 30 grams of EtOAc were mixed. To this mixture, 102 milligrams of VAZO 67 was added. The bottle was made inert with nitrogen gas and sealed. The sealed bottle was tumbled in a 60° C. water bath for 24 hours.

Preparative Example MP16

In a glass bottle, 1.0 gram of the product of Preparative Example MP2, 3.5 grams of methyl methacrylate, 0.5 grams of 3-methacryloxypropyltrimethoxysilane, 0.8 grams of 3-mercaptopropyltrimethoxysilane and 20 grams of EtOAc were mixed. To this mixture, 100 milligrams of VAZO 67 was added. The bottle was made inert with nitrogen gas and sealed. The sealed bottle was tumbled in a 60° C. water bath for 24 hours.

Preparative Example MP17

In a glass bottle, 1.0 gram of the product of Preparative Example MP2, 2.0 grams of methyl methacrylate, 0.5 grams of 3-mercaptopropyltrimethoxysilane and 20 grams of EtOAc were mixed. To this mixture, 101 milligrams of VAZO 67 was added. The bottle was made inert with nitrogen gas and sealed. The sealed bottle was tumbled in a 60° C. water bath for 24 hours.

Preparative Example MP18

In a glass bottle, 0.24 grams of the product of Preparative Example MP1, 4.8 grams of N,N-diethyl acrylamide, 4.6 grams of ACN and 3.0 grams of THF were mixed. To this mixture, 50 milligrams of VAZO 67 was added. The bottle was made inert with nitrogen gas and sealed. The sealed bottle was tumbled in a 60° C. water bath for 24 hours.

Preparative Example MP19

In a glass bottle, 0.295 grams of the product of Preparative Example MP2, 4.8 grams of N,N-dimethyl acrylamide, 6.9 grams of ACN and 0.8 grams of THF were mixed. To this mixture, 51 milligrams of VAZO 67 was added. The bottle was made inert with nitrogen gas and sealed. The sealed bottle was tumbled in a 60° C. water bath for 24 hours.

Preparative Example MP20

In a glass bottle, 0.17 grams of the product of Preparative Example MP4, 2.7 grams of N,N-dimethyl acrylamide, 0.017 grams of 3-mercaptopropyltrimethoxysilane and 4.3 grams of ACN were mixed. To this mixture, 29 milligrams of VAZO 67 was added. The bottle was made inert with nitrogen gas and sealed. The sealed bottle was tumbled in a 60° C. water bath for 24 hours.

Preparative Example MP21

In a glass bottle, 0.33 grams of the product of Preparative Example MP6, 0.87 grams of N,N-dimethyl acrylamide, 1.6 grams of ACN and 0.2 grams of THF were mixed. To this mixture, 12 milligrams of VAZO 67 was added. The bottle was made inert with nitrogen gas and sealed. The sealed bottle was tumbled in a 60° C. water bath for 24 hours.

Preparative Example MP22

In a glass bottle, 1.00 gram of the product of Preparative Example MP8, 1.50 grams of methyl acrylate, 6.75 grams of ACN and 0.75 grams of THF were mixed. To this mixture, 17.5 milligrams of VAZO 67 was added. The bottle was made inert with nitrogen gas and sealed. The sealed bottle was tumbled in a 55° C. water bath for 24 hours.

Preparative Example MP23

In a glass bottle, 1.00 gram of the product of Preparative Example MP8, 4.00 grams of methyl methacrylate, 0.025 grams of acryloxybenzophenone, 6.75 grams of ACN and 0.75 grams of THF were mixed. To this mixture, 17.5 milligrams of VAZO 67 was added. The bottle was made inert with nitrogen gas and sealed. The sealed bottle was tumbled in a 55° C. water bath for 24 hours.

Preparative Example MP24

In a glass bottle, 1.50 grams of the product of Preparative Example MP8, 1.50 grams of N,N-dimethyl acrylamide, 6.75 grams of ACN and 0.75 grams of THF were mixed. To this mixture, 17.5 milligrams of VAZO 67 was added. The bottle was made inert with nitrogen gas and sealed. The sealed bottle was tumbled in a 55° C. water bath for 24 hours Preparative Example MP25

In a glass bottle, 1.00 gram of the product of Preparative Example MP8, 3.00 grams of methyl methacrylate, 1.00 gram of isobornyl methacrylate, 0.025 grams of 4-acryloxybenzophenone, 13.50 grams of ACN and 1.50 grams of THF were mixed. To this mixture, 17.5 milligrams of VAZO 67 was added. The bottle was made inert with nitrogen gas and sealed. The sealed bottle was tumbled in a 55° C. water bath for 24 hours.

Preparative Example MP26 (Terpolymer)

In a glass bottle, 30 grams of the product of Preparative Example MP8, 35 grams of methyl methacrylate, 35 grams of isobornyl methacrylate, 0.30 grams of 4-acryloxybenzophenone, 233 grams of butyl acetate/acetonitrile were mixed. To this mixture, 0.3 grams of VAZO 67 was added. The bottle was made inert with nitrogen gas and sealed. The sealed bottle was tumbled in a 60° C. water bath for 20 hours.

Preparative Example MP27 (Copolymer)

In a glass bottle, 15 grams of methyl methacrylate, 15 grams of isobornyl methacrylate, 70 grams of butyl acetate were mixed. To this mixture, 0.09 grams of VAZO 67 was added. The bottle was made inert with nitrogen gas and sealed. The sealed bottle was tumbled in a 60° C. water bath for 20 hours. The resulting polymer was ready for dilution and spin coating.

Preparative Example MM1

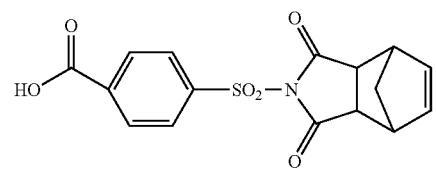

In a glass reaction vessel, a mixture of norbornene-2,3-dicarboxylic anhydride (26.9 grams), p-sulfamylbenzoic acid (30.0 grams), TEA (49.8 grams) and DMF (82 grams) were stirred and heated to 50° C. under a nitrogen atmosphere for two hours followed by heating overnight at 90° C. The mixture was cooled to room temperature and acetic anhydride (18.3 grams) was added to the flask. The mixture was stirred overnight at room temperature, poured into aqueous 1N HCl and the resultant solid was isolated by filtration and dried using a vacuum oven. The resulting solid was recrystallized from glacial acetic acid to give the desired product. Yield: 12.6 grams.

Preparative Example MM2

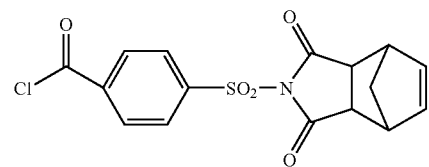

In a glass reaction vessel fitted with a reflux condenser and a nitrogen inlet, a mixture of the carboxylic acid product of Preparative Example MM1 (5.0 grams), thionyl chloride (2.2 grams), DMF (1 drop) and ACN (28.9 milliliters) were stirred under a nitrogen atmosphere and heated to reflux for one hour. The mixture was allowed to cool to room temperature and the volatile components were removed using a rotary evaporator. The resultant solid washed into a fritted glass funnel, washed with diethyl ether, and then dried at room temperature under a stream of nitrogen gas to afford the desired product. Yield: 4.7 grams.

Preparative Example MM3

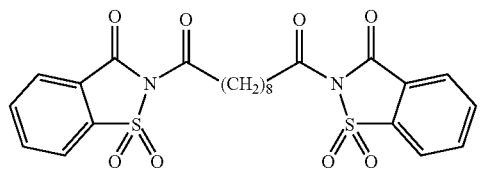

To a stirred slurry of dry Na saccharin (10.25 grams, 0.50 mol) and 200 milliliters of acetone was added sebacoyl chloride (6.0 grams, 0.025 mol) under a nitrogen atmosphere. The resulting mixture was stirred for 20 hours at room temperature. IR spectroscopy showed the absence of peaks for —COCl. The mixture was filtered and washed with acetone to give 11.8 grams of white solid. The acetone was removed from the wash solution to yield 3.7 grams tan solid which was combined with the filtrate, washed with water and dried to give the desired product (structure conformed by NMR) which was slightly soluble in ACN, acetone and 2-butanone. Yield: 9.1 grams.

Preparative Example MM4

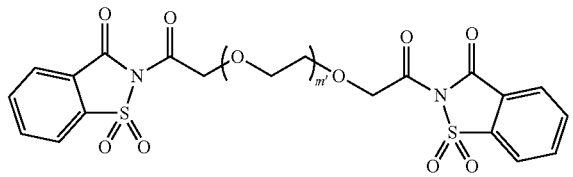

To a mixture of PEG 600 diacid (30 grams, 0.05 mol, where m' is approximately 14) in 100 milliliters $CH_2Cl_2$ was added 10 milliliters $SOCl_2$ with immediate evolution of HCl. After 20 hours, the solvent was removed under vacuum to give 33.6 grams of pale yellow oil. Of this, 6.4 grams (0.01 mol) was added to dry Na saccharin (4.1 grams, 0.02 mol) and the resulting slurry was stirred for 24 hours, filtered and dried under vacuum to give the desired product as a pale tan syrup. Yield: 9.3 grams.

Preparative Example MM5

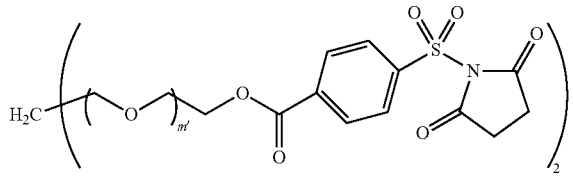

In a glass reaction vessel, a sample of the chlorocarbonyl product of Preparative Example M2 (1.0 grams) was dissolved in NMP (3.6 grams) and chilled in an ice bath. A solution of PEG 3400 (3.54 grams, where m' is approximately 77) in THF (3.54 grams) was slowly added to the flask. The mixture was stirred for overnight as the mixture warmed to room temperature. The mixture was concentrated, recrystallized with IPA and the resulting white solid was filtered and rinsed with chilled IPA to give the desired product. Yield: 4.17 grams. A hydrogel was formed by the addition of polyethylenimine, average molecular weight ($M_w$) is approximately 2,000, 50 wt-% solution in water (0.17 grams) to an aqueous solution of this product (0.50 grams), at 50 wt-%.

Preparative Example MM6

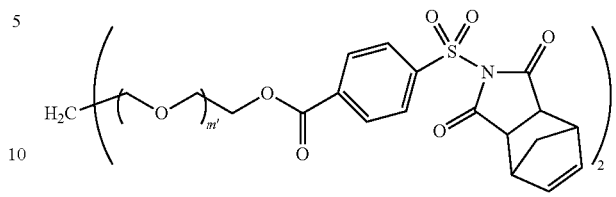

In a glass reaction vessel, a sample of the chlorocarboxy product of Preparative Example MM2 (1.99 grams) was dissolved in THF (10 grams). A solution of PEG 3400 (8.20 grams, where m' is approximately 77), pyridine (0.48 grams) and THF (3.54 grams) was slowly added and the resulting mixture was stirred overnight. The mixture was concentrated, recrystallized with IPA and the resulting white solid was filtered and rinsed with chilled IPA to give the desired product. Yield: 9.0 grams.

Preparative Example MM7

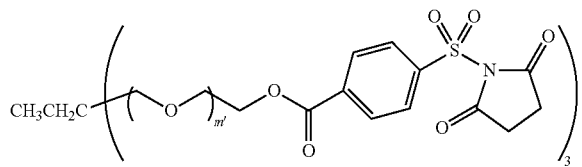

In a glass reaction vessel, a sample of the chlorocarbonyl product of Preparative Example M2 (2.00 grams) was dissolved in THF (8 grams). A solution of TPEG 990 (2.07 grams, where m' is approximately 22), TEA (0.70 grams) and THF (8.0 grams) was slowly added and the resulting mixture was stirred overnight. IR spectroscopy showed the absence of peaks for —COCl. The mixture was concentrated, reconstituted in EtOAc, and filtered to give a clear, colorless solution at 24.5% solids.

Waveguide Material Examples

Waveguide Example W1

A 50/50 copolymer of isobornyl methacrylate and methyl methacrylate (poly(IBMA/MMA)) was made as in Preparative Example MP27 and diluted to 7-10% solids in butyl acetate.

Waveguide Example W2

Polymethyl methacrylate (PMMA) was made by mixing 30 grams of methyl methacrylate and 70 grams of butyl acetate in a glass bottle. To this mixture, 0.09 grams of VAZO 67 was added. The bottle was made inert with nitrogen gas and sealed. The sealed bottle was tumbled in a 60° C. water bath for 20 hours. The resulting polymer was ready for dilution and spin coating. Spin coating was done with a solution diluted to 7-10% solids in butyl acetate.

Waveguide Example W3

Polyisobornyl methacrylate (PIBMA) was made by mixing 30 grams of isobornylmethacrylate and 70 grams of butyl acetate in a glass bottle. To this mixture, 0.09 grams of VAZO 67 was added. The bottle was made inert with nitrogen gas and sealed. The sealed bottle was tumbled in a 60° C. water bath for 20 hours. The resulting polymer was ready for dilution and spin coating. Spin coating was done with a solution diluted to 7-10% solids in butyl acetate.

Waveguide Example W4A

Polystyrene (PS) from Scientific Polymer Products (Ontario, N.Y.) ($M_w$=280 KDa) was made to 10% solids in 2-butoxy ethyl acetate.

Waveguide Example W4B

Polystyrene (PS) from Scientific Polymer Products (Ontario, N.Y.) ($M_w$=280 KDa) was made to 10% solids in toluene.

Waveguide Example W5

Poly(styrene/MeFBSEMA/A174), a copolymer mixture of 47.5% polystyrene, 47.5% N-Methyl perfluorobutanesulfonamidoethyl methacrylate, and 5% of Silane-A174 ([3-(methacryloyloxy)propyl]trimethoxysilane from GSF Chemicals, Tullytown, Pa.) was made by adding into a glass bottle 4.75 g styrene, 4.75 g N-methyl perfluorobutanesulfonamidoethyl methacylate, 0.5 g Silane-A174, 100 mg VAZO 67, and 25.0 g ethyl acetate. After purging with nitrogen, the sealed bottle was tumbled in a 60° C. water bath for 22 hours. The resulting polymer was ready for dilution and spin coating. Spin coating was done with a solution diluted to 7-10% solids in propyl acetate.

Waveguide Example W6

Poly(MMA MeFBSEMA/A174), a copolymer mixture of 47.5% polymethyl methacrylate, 47.5% N-Methyl perfluorobutanesulfonamido ethyl methacrylate, and 5% of Silane-A174 ([3-(methacryloyloxy)propyl]trimethoxysilane from GSF Chemicals, Tullytown, Pa.) was made by adding into a glass bottle 4.75 g methyl methacrylate, 4.75 g N-methylperfluorobutanesulfonamidoethyl methacylate, 0.5 g Silane-A174, 100 mg VAZO 67, and 25.0 g ethyl acetate. After purging with nitrogen, the sealed bottle was tumbled in a 60° C. water bath for 40 hours. The resulting polymer (28% solids) was ready for dilution and spin coating. Spin coating was done with a solution diluted to 7-10% solids in propyl acetate.

Waveguide Example W7A

Poly(N-vinylcarbazole) (PVK), available from Polymer Source (Montreal, Canada) molecular weight 58.6 KDa was made to 7-10% solids in toluene.

Waveguide Example W7B

Poly(N-vinylcarbazole) (PVK), available from Polymer Source (Montreal, Canada) molecular weight 118 KDa was made to 7-10% solids in toluene.

Waveguide Example W8

Polyvinylidene fluoride (PVDF) available from Dyneon 11008/0003 (Oakdale, Minn.) was made to 6% solids in methyl ethyl ketone.

Waveguide Example W9

A terpolymer of tetrafluoroethylene, hexafluoropropylene and vinylidene fluoride (THV), available from Dyneon (Oakdale Minn.), as THV 220, was made to 8% solids in methyl ethyl ketone.

Waveguide Example W10A

A two part (1:1) room temperature curing epoxy was prepared with Part A: bisphenol A diepoxide (DER 317 Epoxy Resin, available from Dow Chemical, Midland, Mich.) in a diluent of O-Cresyl Glycidyl Ether, in a 90:10 ratio and Part B: amine curative (Resolution Performance Products Epi-Cure 3251), both parts diluted to 7-10% solids in xylene.

Waveguide Example W10B

A two part (1:2, A:B) room temperature curing epoxy was prepared with Part A: bisphenol A diepoxide (Dow Chemical DER 317 Epoxy Resin) in a diluent of O-Cresyl Glycidyl Ether, in a 90:10 ratio and Part B: amine curative (Resolution Performance Products Epi-Cure 3251), both parts diluted to 7-10% solids in xylene.

Waveguide Example W11

A Polyimide (PI) available as Pyralin PI 2610 was made to 10% solids in N-methyl-2-pyrrolidone from HD MicroSystems of Wilmington, Del.

Preparation of Sensors with Thermoplastic Waveguides

The waveguide materials described above in Examples W1-W11 were used to prepare sensors with waveguide materials coated, on them. All of the base sensors used were $LiTaO_3$ devices operating at 103 MHz provided by Sandia National Laboratories. The sensor edges were ground to reduce the bulk wave noise caused by diffraction. The dust was blown off using compressed air. The sensors were then washed with methyl ethyl ketone followed by isopropyl alcohol and de-ionized water. Sensors were placed on glass slide in large Pyrex watch glass and covered immediately with smaller Pyrex watch glass (to prevent contamination by dust). The watch glass was then placed under 2-15 Watts (2-15 joule/second) UV lights and illuminated for 20 minutes, as a method of cleaning.

The waveguide materials W1-W9 were spin coated onto the sensors, to obtain an approximate thickness of 0.8 to 1 micron waveguide material on the sensor, using a Spin Coater P6700 Series manufactured by Specialty Coating Systems, Inc. The spin coater was housed into a "clean box", a Plexiglas enclosed space under positive pressure, large enough for the spin coater and a small amount of working space for depositing waveguides, positioning the sensor, etc.

Using tweezers and wearing gloves, the sensors were placed onto chuck of the spin coater inside the clean box. A drop of waveguide solution was placed in the middle of sensor, and then other drops were "dragged" around successive edges. Finally, another 3-4 drops of waveguide material was placed onto middle of sensor to flood the sensor surface. Solution was either deposited via a syringe through a 0.2 µm filter or filtered beforehand (with a 0.2 µm filter) and deposited with a small pipette. Spin coating was done for a time of 60 seconds with a ramp of 5 seconds at a speed of approximately 1100 rpm (rpm depends on material viscosity, desired thickness).

The electrical contacts pads for the interdigitated electrodes on the sensor were cleaned twice using a cotton swab lightly soaked with the waveguide diluent. After the pad-cleaning step, the sensors were heated in the clean box, on a hot plate at 90° C. for at least 5 minutes. The sensors were further heated in a nitrogen-purged oven at 150° C. and allowed to cool to room temperature in the oven, after heating for 45 minutes.

Waveguide material W10 was prepared into sensors following similar preparation steps as done for W1-W9 and W11, but with the following exceptions. After cleaning the pads, the W10 (epoxy) coated sensor was left to cross-link at room temperature before the dry and wet measurements.

Dry & Wet Measurements of Waveguide Materials and Tables of Results

Dry measurements were taken by LabView software configured with an Agilent 8753ET network analyzer and a passive circuit board where measurement of the two channels present on each sensor are performed sequentially (e.g., channel A is measured first, followed by channel B). To characterize the change in the insertion loss of the sensor due to the presence of the waveguide layer, two sensors were used for each waveguide material. Since each sensor has two channels, a total of four data points were obtained from the two sensors measured. For a given waveguide material, the insertion loss was measured for the uncoated sensors (no waveguide) first, and then again after coating the same sensor with the waveguide layer. The insertion loss was measured at the operating frequency that gave the optimum signal for both uncoated and waveguide coated sensors. That optimum operating frequency corresponds to the resonant frequency of the device (103 MHz±1 MHz for the Sandia sensor). The table below (Acoustic Characterization of Dry Sensors) shows an average of these four measurements and its standard deviation. All measurements are for dry sensors (e.g., the sensor is measured in air).

To characterize acoustic stability of the waveguide coated sensor under a liquid, wet measurements were taken using the same hardware as dry measurements except an active electronics board was used instead of a passive board, i.e. the system was capable of reading both channel A and channel B of the sensor simultaneously. Data collected included ten points dry, followed by PBS (phosphate buffer solution, 0.20 M NaPO$_4$ and 0.15 M NaCl with a pH of 7.5) injection. The steady-state buffer flow rate was 0.03 mL/min. The initial ten data points (equivalent to a time elapsed of 5 minutes) allowed the system to come to thermal equilibrium and provided stability of the sensor under dry conditions. An additional seventy points of data (equivalent to a time elapsed of 35 minutes) were collected after buffer flow was initiated. The measurement frequency was fixed at the optimum operating frequency for each sensor measured, and the data was collected as a function of time. Collection of data in the time domain (fixed frequency) allowed a quantitative characterization of waveguide stability. Drifts could be observed in insertion loss, and phase. For each waveguide material, the table below (Acoustic Stability of Sensors Under Water) reports the change (drift) in both insertion loss and phase that occurred over the first 30 minutes after buffer flow over the sensor was initiated. Also reported are the standard deviations for these values. The reported values consist of the average of four measurements (two sensors with two channels each).

In a similar manner we also characterized the acoustic stability of sensors coated with different combinations of waveguide and immobilization chemistry materials, under a liquid (PBS buffer solution as described above). The immobilization chemistries were Terpolymer (Preparative Example MP26), UV curable (Preparative Example MP23) and Disaccharin (Preparative Example MM3). The immobilization chemistries were applied using the spin coating procedure described above. These measurements were performed in the same manner as the ones described for the characterization of the wet acoustic stability of sensors coated by only a waveguide. For each given combination of the waveguide and immobilization chemistry, the table below (Acoustic Stability of Sensors with Waveguide Materials+Immobilization Chemistry) reports the change (drift) in insertion loss that occurred over the first 30 minutes after buffer flow over the sensor was initiated. Also reported are the changes in insertion loss when the sensor goes from the dry state (in air) to the wet state (under the buffer solution). The reported values consist of the average of four measurements (two sensor with two channels each). The measurements for the sensors with no immobilization chemistry represent new experimental replicates.

TABLE 1

ACOUSTIC CHARACTERIZATION OF DRY SENSORS

| Waveguide Polymer Example | Change in Insertion Loss (dry) (dB) | Error in Insertion Loss (dB) |
|---|---|---|
| W1 = P(IBMA/MMA | −0.15 | 2.6 |
| W2 = PMMA | −4.2 | 3.1 |
| W3 = PIBMA | 2.2 | 4.5 |
| W4A = PS in toluene | 4.4 | 3.7 |
| W4B = PS in 2-butoxy ethyl acetate | −3.0 | 3.3 |
| W5 = P(Styrene/MeFBSEMA/A174) | 0.9 | 5.3 |
| W6 = P(MMA/MeFBSEMA/A174) | 3.8 | 4.0 |
| W7A = PVK with MW 58.6K | −2.1 | 3.0 |
| W7B = PVK with MW 118K | −3.8 | 4.4 |
| W8 = PVDF | −34.1 | 8.6 |
| W9 = THV | −25.8 | 8.0 |
| W10 = Epoxy | 0.7 | 3.2 |

TABLE 2

ACOUSTIC STABILITY of SENSORS UNDER WATER
(PBS Buffer Solution)

| Waveguide Polymer Example | Absolute Change in Insertion Loss (wet) (dB) | Error in Absolute Change in Magnitude (wet) (dB) | Absolute Change in Phase (wet) (degrees) | Error in Absolute Change in Phase (wet) (degrees) |
|---|---|---|---|---|
| W1 | 1.4 | 1.2 | 3.0 | 3.9 |
| W2 | 21.7 | 2.5 | 63.3 | 24.9 |
| W3 | 3.0 | 1.9 | 9.2 | 2.3 |
| W4A | 4.6 | 3.3 | 11.5 | 7.8 |
| W4B | 7.3 | 4.3 | 110.3 | 130.1 |
| W5 | 1.0 | 1.0 | 14.3 | 20.0 |
| W6 | 5.2 | 2.0 | 55.9 | 26.4 |
| W7A | 12.4 | 0.6 | 50.8 | 18.5 |
| W7B | 1.1 | 0.7 | 14.7 | 12.0 |
| W8 | — | — | — | — |
| W9 | — | — | — | — |
| W10 | 0.5 | 0.3 | 4.3 | 1.1 |
| W11 | 0.2 | 0.1 | 1.8 | 1.0 |

TABLE 3

ACOUSTIC STABILITY OF SENSORS WITH WAVEGUIDE MATERIAL + IMMOBILIZATION CHEMISTRY

| Waveguide Polymer | Immobilization Chemistry | Change in Insertion Loss from dry to wet (dB) | Absolute Change in Insertion Loss over 30 minutes (PBS Buffer) exposure |
|---|---|---|---|
| W1 | None | −17.6 | 0.6 |
| W1 | Terpolymer | −17.5 | 2.5 |
| W1 | UV Curable | −23.4 | 0.5 |
| W10 | None | −9.4 | 1.8 |
| W10 | Terpolymer | −12.4 | 0.4 |
| W10 | UV Curable | −16.3 | 0.4 |
| W10 | Disaccharin | −16.3 | 0.4 |

Waveguide Example 12

Waveguide Material with Capture/Immobilization

Polymer prepared as in Preparative Example MP26 (terpolymer) was spin-coated on the sensors, which were ground and cleaned, as in the earlier example. The coating conditions were maintained the same as before except for the rpm levels set at 1500. A mixture of butylacetate and acetonitrile (50/50) was used as solvent. The sensor pads were cleaned with the same solvent. The coated sensors were bonded to the flex circuit to make electrical contact using 3M 7313 z-axis adhesive. The rabbit anti S. aureus antibody in CHES buffer (pH 9) at a concentration of 50 µg/ml was used to react with the surface. A 15 µl sample of the solution was placed on each channel and allowed to react for 30 minutes (mins). The sensors were washed with PBS buffer followed by PBS with 0.05% TWEEN 20 and finally with PBS buffer. The sensor was placed in the flow cartridge and dry and wet measurements were taken using the procedure described above.

Insertion loss at the start of measurement was −10.61 db for channel A and −11.47 db for channel B. The change in insertion loss at the end of the measurement was 0.2 db for channel A and 0.1 db for channel B. The change in phase was measured as 0.5 degrees for channel A and 0.25 degrees for channel B.

Capture/Detection Examples

Capture Example 1

Capture of S. aureus to S. aureus Antibody Bound to the Terpolymer:
Waveguide Coating A polymer prepared as in Preparative Example MP26 was dissolved in a mixture of acetonitrile and butylacetate (50/50) to give a 1% solution for spin coating. The solution was spin coated as described previously on a cleaned glass slide. The glass slide was cleaned in a base bath followed by washing with water and ethanol and dried in air before coating. The thickness of the coating was measured to be 0.8 microns.
Antibody Binding Antibody was then bound to the surface by transferring the antibody solution to the coated waveguide sensor. Rabbit IgG antibody specific to Staphylococcus aureus was obtained from Accurate Chemical and Scientific, Westbury, N.Y., as a 4.52 mg/ml solution. This solution was diluted with CHES buffer to give a solution with a concentration of the IgG of 50 µg/ml. The antibody solution was placed on the terpolymer coating for 30 minutes. The sample washed with phosphate buffered saline buffer. "PBS buffer" solution consisted of 0.02 M Sodium Phosphate (Sigma-Aldrich) and 0.15 M Sodium Chloride (Sigma-Aldrich). The sample was then washed further with PBS buffer containing 0.05% (v/v) polyoxyethylene(20) sorbitan monolaurate, (trade designation TWEEN 20 available from, Sigma-Aldrich, St. Louis, Mo.), followed by a PBS buffer.
Staining with Acridine Orange Acridine orange solution was obtained from Molecular Probes (catalog number A3568, Eugene, Oreg.) at a concentration of 10 mg/ml. It was diluted to 0.01 mg/ml with distilled water and used for staining. S. aureus (ATCC 25923) in PBS buffer containing 0.2% (w/v) PLURONIC L64 Surfactant (BASF Corporation, Mount Olive, N.J., PBS-L64 buffer) was stained with acridine orange. A 500 µl solution of S. aureus bacteria was mixed with 500 µl of acridine orange diluted solution and allowed to stand for 15 mins at room temperature. The solution was vortexed and centrifuged for 5 mins at 8000 revolutions per minute (rpm). The supernatant was removed and 500 µl of distilled water added, vortexed, and centrifuged again. This washing procedure was repeated two more times and then the bacteria were dispersed in PBS-L64 buffer and vortexed well to break the clumps. The concentration of stained S. aureus in the buffer was $10^9$ colony forming units per milliliter ($10^9$ cfu/ml).
Capture on Surface A 50 µl of the S. Aureus (ATCC 25923) in PBS-L64 stained with acridine orange was placed on the antibody surface for 10 mins. The sample was then washed with PBS buffer, PBS with TWEEN 20, followed by PBS buffer. The samples were stored in PBS buffer until it was observed through confocal microscope.

The sample was analyzed by confocal microscopy using a Model Olympus FV-300 confocal microscope (available from Leeds Precision, Inc., Minneapolis, Minn.). S. aureus was determined to be bound by presence of contrasting spots against the dark background in the microscope images of the surface.

Capture Example 2

Capture on Epoxy Waveguides: Epoxy Waveguide Mixed with Silane:

A two part, room temperature curing epoxy was used to make a waveguide coating. Part A was bisphenol A diepoxide (Dow Chemical DER 317 Epoxy resin, Midland, Mich.) in a diluent (O-Cresyl Glycidyl Ether) in a 90/10 ratio. Part B was an amine curative (Resolution Performance Products Epi-Cure 3251, Houston, Tex.). Both part A and B were diluted 8% solids in xylene and were mixed 1:1. Glycidoxy silane (Silane A187, GSF Chemicals, Tullytown, Pa.) was mixed into the epoxy solution at 1% to make a waveguide material for coating on a sensor. The epoxy system was spin coated as in the above waveguide examples.

Saccharin silane as prepared in Preparative Example M8 was dissolved in dichloromethane at a 1% concentration. The epoxy waveguide coated sensor with Silane A187 (GSF Chemicals, Tullytown, Pa.) mixed in the epoxy was immersed in saccharin silane solution for 15 mins. The sensor was removed and washed with solvent and dried using laboratory air supply.

Antibody was applied to the sensor as above. Stained S. aureus in the buffer was applied to the sensor surface as above. The sample was analyzed by confocal microscopy as above. S. aureus bacteria was determined to be bound to the surface of the sample.

Capture Example 3

Epoxy Waveguide with Increased Curative:

The two-part epoxy used in Capture Example 2 was used to make a waveguide only the ratio of Part A to Part B was 1:2. The coating was applied and cured as in Capture Example 2. The coated sensor was reacted with disaccharin prepared as in Preparative Example MM3). The epoxy coated sensor was placed in a 1% solution of disaccharin in N-methylpyrrolidinone (NMP) for 15 mins. The dip coated sample was then washed with NMP further and dried using laboratory air.

Antibody was applied to the sensor as above. Stained S. aureus in the buffer was applied to the sensor surface as above. The sample was analyzed by confocal microscopy as above. S. aureus bacteria was determined to be bound to the surface of the sample.

Capture Example 4

Epoxy Waveguide with Terpolymer:

A two-part epoxy waveguide with increased amount of curative was prepared as in Capture Example 3. Polymer as described in Preparative Example MP26 (terpolymer) dissolved in acetonitrile/butylacetate mixture (50/50) at a 1% concentration was spin-coated on the epoxy coated sensor using the spin coating procedure previously described. Antibody was applied to the sensor as above. Stained S. aureus in the buffer was applied to the sensor surface as above. The sample was analyzed by confocal microscopy as above. S. aureus bacteria was determined to be bound to the surface of the sample.

Capture Example 5

Epoxy Waveguide with UV Curable Polymer:

A two-part epoxy waveguide with increased amount of curative was prepared as in Capture Example 3. A 1% UV curable polymer solution was made using Preparative Example MP23 dissolved in acetonitrile. This solution was spin coated as described above and UV cured by exposure to high intensity UV light.

Antibody was applied to the sensor as above. Stained S. aureus in the buffer was applied to the sensor surface as above. The sample was analyzed by confocal microscopy as above. S. aureus bacteria was determined to be bound to the surface of the sample.

Capture Example 6

Spray Jetting of Terpolymer onto the PMMA/IBMA Waveguide Spin-coated on Glass Slide; Protein A Beads Capture:

Glass slides were placed in a base bath, followed by distilled water and ethanol. The glass slides were dried in air. The PMMA/IBMA copolymer prepared as in Preparative Example MP27 was spin coated on the glass slide using the procedure described above.

The polymer coated glass slides were then spray-jetted with Terpolymer (Preparative Example 26MP) solution at a concentration of 1.0% in butylacetate/acetonitrile (50/50) using a flow rate of 30 cm³/min using an aerosol jet deposition system (Model M3D-101, available from Optomec, Inc., Albuquerque, N. Mex.).

Rabbit IgG antibody specific to *Staphylococcus aureus* obtained from Accurate Chemical and Scientific, Westbury, N.Y., as a 4.52 mg/ml solution was diluted with CHES buffer to give a solution with a concentration of the IgG of 50 µg/ml.

The antibody solution was placed on the terpolymer coating for 30 mins. The sample was washed with PBS buffer, PBS buffer containing 0.05% TWEEN 20 followed by PBS buffer. A 50 µl volume of fluorescent Protein A beads 1 micron size obtained from Polysciences, Inc., Warrington, Pa. (available as Protein A Fluoresbrite YG polystyrene Microspheres, Catalog No. 17845) was placed on the surface for 15 mins. The concentration of Protein A beads in the bottle 204 µg/ml, in a buffer of: 0.02 M Sodium phosphate (pH 7.4), 8 mg/ml NaCl, 10 mg/ml BSA, 0.1% sodium azide, and 5% glycerol. The sample washed with PBS buffer and then distilled water and observed through a confocal microscope (same as above). The Protein A beads were then counted. This procedure was repeated changing the concentration of Terpolymer to give the results shown in the Table 4 below.

TABLE 4

| Protein A Bead Capture | |
|---|---|
| Terpolymer Concentration Wt-% in solvent | Bead Count |
| 0 | 1947 |
| 0.25 | 16,634 |
| 0.50 | 10,793 |
| 1.0 | 11,970 |

Capture Example 7

Capture of Protein A Beads on Sensor Coated with PMMA/IBMA Waveguide, Spray-jetted with Terpolymer and Flowed with Protein A Beads:

The Sandia 103 LiTaO₃ sensors (described above) were coated with PMMA/IBMA (Preparative Example MP27) polymer to provide a waveguide at 0.8 µm thickness. The terpolymer was spray-jetted as described above onto the waveguide. Rabbit anti S. aureus antibody from Accurate Chemicals was hand-coated on the channels using the antibody coating procedure from above. The sensor was mounted in a flow cartridge after bonding to the flex circuit as described above. PBS was flowed over the sensor first at a rate of 3 ml/min to remove the bubbles in the system, after which the system was equilibrated for a period of 30 mins by flowing at a rate of 0.03 ml/min. A 250 µl volume of Protein A beads in PBS-L64 solution was injected and was run at 0.03 ml/min. This injection was followed by further equilibration with PBS and washing at a rate of 4 ml/min. The sensor was removed and observed through a confocal microscope and beads were observed attached to the surface.

Capture Example 8

Protein A on Acoustic Biosensor:

A LiTaO₃ based Shear horizontal wave acoustic sensor operating at 103 MHz and fabricated in Sandia National Laboratories was used in these experiments. Single-side polished 36° YX LiTaO₃ (Sawyer Research Products Inc., Eastlake, Ohio) wafers were initially cleaned by rinsing with acetone, methanol, isopropanol, and 18 MΩcm water, respectively, then dried with nitrogen. A lift-off procedure was used to define the interdigital transducers for each delay line. To promote adhesion, a 100 angstrom titanium (Ti) binding layer was evaporated on the LiTaO₃ wavers using an e-beam evaporator (CVC Products Inc., Rochester, N.Y.). An 800 angstrom gold layer was then deposited on the Ti film by resistive evaporation.

The sensor was spin coated with PMMA/IBMA (Preparative Example MP26) polymer to provide a waveguide at 0.8 μm thickness. The sensor was then bonded to the flex circuit using z-axis adhesive. Polymer prepared as in Preparative Example MP26 (terpolymer) was dissolved in butyl acetate at 1% and spray-jetted onto the waveguide layer using an aerosol jet deposition system (Model M3D-101, available from Optomec, Inc., Albuquerque, N. Mex.).

The active channel of the sensor was then hand-coated with Rabbit anti *Staphylococcus aureus* antibody obtained from Accurate chemicals and Chicken antibody obtained from Jackson Immuno Research on the reference channel. The antibody concentration was adjusted to be around 50 μg/ml in CHES buffer (from Sigma chemicals) at pH 9.0. The antibody was allowed to react for 30 mins and then washed with PBS buffer followed by the same buffer containing TWEEN 20 and with a last rinse of PBS buffer. The sensor on flex was then secured in a flow cartridge. The temperature of this cartridge was maintained at 28° C. by the fluid circulating from a constant temperature bath.

The sensor was equilibrated for 30 mins by running PBS-L64 buffer delivered through a syringe pump attached to a six port valve. The flow rate was adjusted to 3 ml/min to remove the air bubbles in the system followed by a flow at 30 μl/min. When equilibrated, a solution of Protein A at a concentration of 1 μg/ml Protein A (Protein A obtained from Zymed, San Francisco, Calif.) was injected through the one of the six-port valves. The loop size was adjusted such that only 500 μl of the sample was injected into the sensor pod. After this sample of was delivered to the cartridge, buffer at 30 μl/min flow rate was resumed.

Phase data was collected for each channel of the sensor over a 1.8 MHz frequency span around 103 MHz. The measurements were collected using an Agilent 8753ES network analyzer and LabView software for data acquisition. A straight signal path in a printed circuit board was used, which had an inline switch to achieve sole active or reference channel measurements to eliminate cross talk. Acquired data consisted of a phase vs. frequency vs. time matrix for both the active and reference channels.

The raw phase data was first processed by time domain gating, essentially functioning to filter noise from the primary acoustic wave signal. The phase was extracted at a fixed frequency (103 MHz). Data extraction occurred for both the active and reference channel individually. Phase was used to determine a response. The final step in data analysis was subtracting the reference channel signal from the active channel signal to remove environmental noise factors that occurred during an experiment. This generated a single curve consisting two basic regions: a baseline phase prior to analyte injection over the sensor surface and an offset phase after injection. The magnitude of the offset was dependent on the type and concentration of analyte.

The above procedure was repeated with varying concentrations of Protein A in solution and the sensor response recorded and phase change determined with the results in Table 5 below.

TABLE 5

Capture/Detection of Protein A

| Concentration (μg/ml) | Average phase shift |
|---|---|
| 0.13 | 0.13 |
| 0.25 | 0.33 |

TABLE 5-continued

Capture/Detection of Protein A

| Concentration (μg/ml) | Average phase shift |
|---|---|
| 0.33 | 0.40 |
| 0.5 | 0.60 |
| 1 | 0.64 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An acoustic sensor comprising a surface comprising:
a soluble polymer having two or more pendant groups independently selected from the group consisting of functional groups having the following formulas:

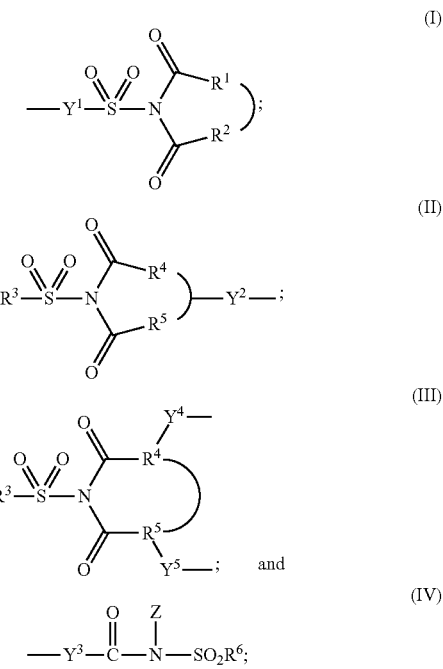

wherein:
$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;
$R^3$ is an alkyl, aryl, aralkyl, or —$NR^aR^b$ wherein $R^a$ and $R^b$ are each an alkyl group or taken together with the nitrogen atom to which they are attached form a four to eight membered heterocyclic group;

R[4] and R[5] together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

R[6] is an alkyl, fluoroalkyl, chloroalkyl, aryl, —NR$^c$R$^d$ wherein R$^c$ and R$^d$ are each an alkyl group or taken together with the nitrogen atom to which they are attached form a four to eight membered cyclic group, or R[6] taken together with R$^e$ and the groups to which they are attached form the four to eight membered heterocyclic or heterobicyclic group that can be fused to the optional aromatic group, optional saturated or unsaturated cyclic group, or optional saturated or unsaturated bicyclic group;

Z is an alkyl, aryl, or —(CO)R$^e$ wherein R$^e$ together with R[6] and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

Y[1], Y[2], and Y[3] are each independently a single bond or a divalent group selected from the group consisting of an alkylene, heteroalkylene, arylene, carbonyl, carbonyloxy, carbonylimino, oxy, thio, —NR$^f$— where R$^f$ is hydrogen or alkyl, and combinations thereof; and Y[4] and Y[5] are each a bond.

2. The acoustic sensor of claim 1 which is a surface acoustic wave sensor.

3. The acoustic sensor of claim 2 which is a shear horizontal surface acoustic wave sensor.

4. The acoustic sensor of claim 3 which can operate in the Love mode.

5. The acoustic sensor of claim 1 comprising a waveguide layer and an immobilization overlayer.

6. The acoustic sensor of claim 5 wherein the immobilization layer comprises the soluble polymer having two or more pendant groups independently selected from the group consisting of functional groups (I), (II), (III), and (IV).

7. The acoustic sensor of claim 6 wherein the soluble polymer is a random polymer having a molecular weight of at least 1000, and is of the following formula:

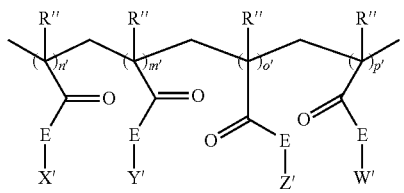

wherein:
each R' is independently H or CH$_3$;
each E is —O— or —NR$^f$—, where R$^f$ is hydrogen or alkyl;
m', n', o', p' represent the number of times each moiety is present in the polymer;
X', Y', Z', and W' are independently selected from the group consisting of alkyl, aryl, hydroxy ester, alkoxyalkyl, alkoxyaryl, ether, fluoroalkyl, trialkoxysilylalkyl, and N-containing groups; and at least one of X', Y', Z', or W' includes an acylsulfonamide group of the following formula:

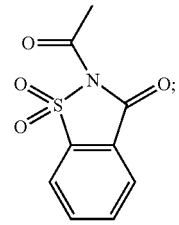

and
the polymer includes at least two distinct moieties.

8. The acoustic sensor of claim 7 wherein at least one of X', Y', Z', or W' is the following group:

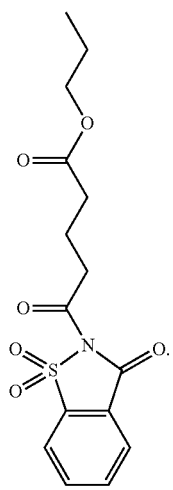

9. The acoustic sensor of claim 8 wherein the soluble polymer is selected from the group consisting of:

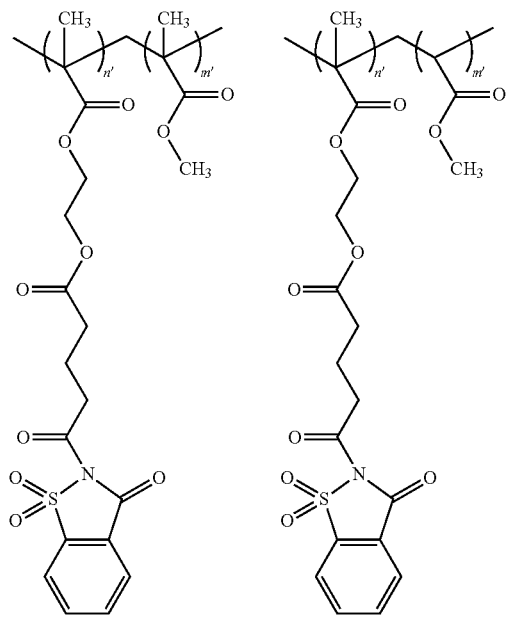

75

-continued

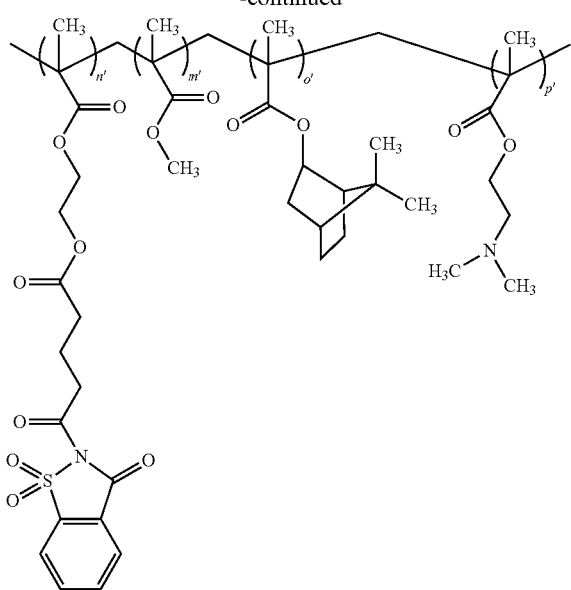

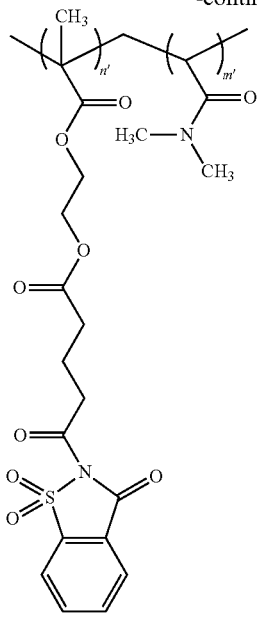

wherein m', n', o', and p' represent the number of times each moiety is present in the polymer.

10. The acoustic sensor of claim 9 wherein the soluble polymer has the formula:

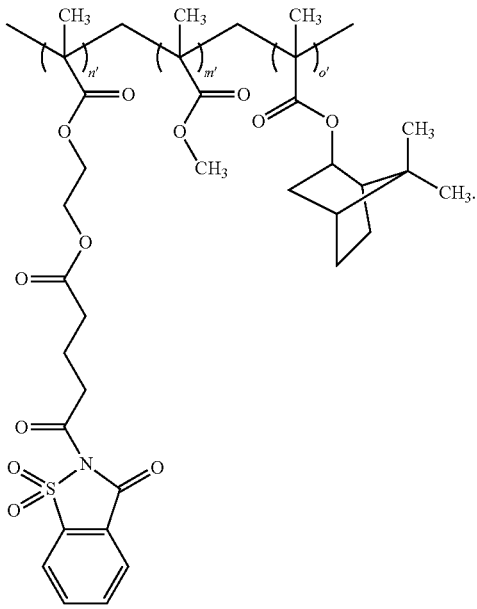

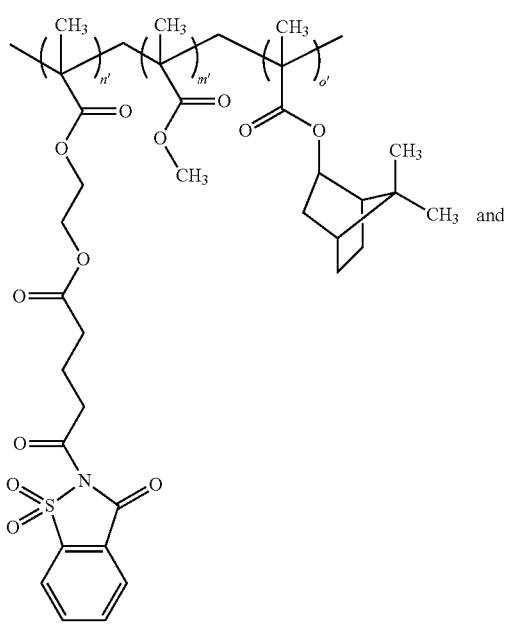

and

11. The acoustic sensor of claim 5 wherein the waveguide layer comprises a polymer derived from two or more different monomers wherein at least one is a (meth)acrylate monomer, the polymer derived from N-vinylcarbazole, the polyepoxide, the $VF_2$-containing fluoropolymer, or combinations thereof.

12. The acoustic sensor of claim 11 wherein the waveguide layer comprises the polymer derived from two or more different monomers wherein at least one is a (meth)acrylate monomer, the polyepoxide, or combinations thereof.

13. The acoustic sensor of claim 11 wherein the immobilization layer comprises the soluble polymer having two or more pendant groups independently selected from the group consisting of functional groups (I), (II), (III), and (IV).

14. The acoustic sensor of claim 1 comprising an immobilizing waveguide layer.

15. The acoustic sensor of claim 14 wherein the immobilizing waveguide layer comprises the soluble polymer having two or more pendant groups independently selected from the group consisting of functional groups (I), (II), (III), and (IV).

16. The acoustic sensor of claim 15 wherein the immobilizing waveguide layer comprises a random polymer having a molecular weight of at least 1000, and is of the following formula:

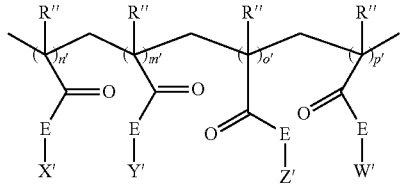

wherein:
each R" is independently H or CH$_3$;
each E is —O— or —NR$^f$—, where R$^f$ is hydrogen or alkyl;
m', n', o', p' represent the number of times each moiety is present in the polymer;
X', Y', Z', and W' are independently selected from the group consisting of alkyl, aryl, hydroxy ester, alkoxyalkyl, alkoxyaryl, ether, fluoroalkyl, trialkoxysilylalkyl, and N-containing groups; and
at least one of X', Y', Z', or W' includes an acylsulfonamide group of the following formula:

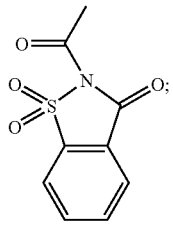

and
the polymer includes at least two distinct moieties.

17. The acoustic sensor of claim 16 wherein at least one of X', Y', Z', or W' is the following group:

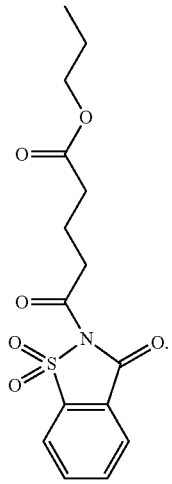

18. The acoustic sensor of claim 17 wherein the soluble polymer is selected from the group consisting of:

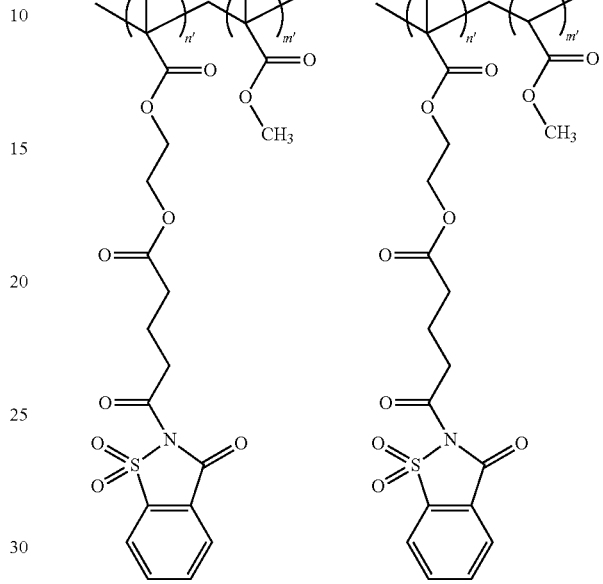

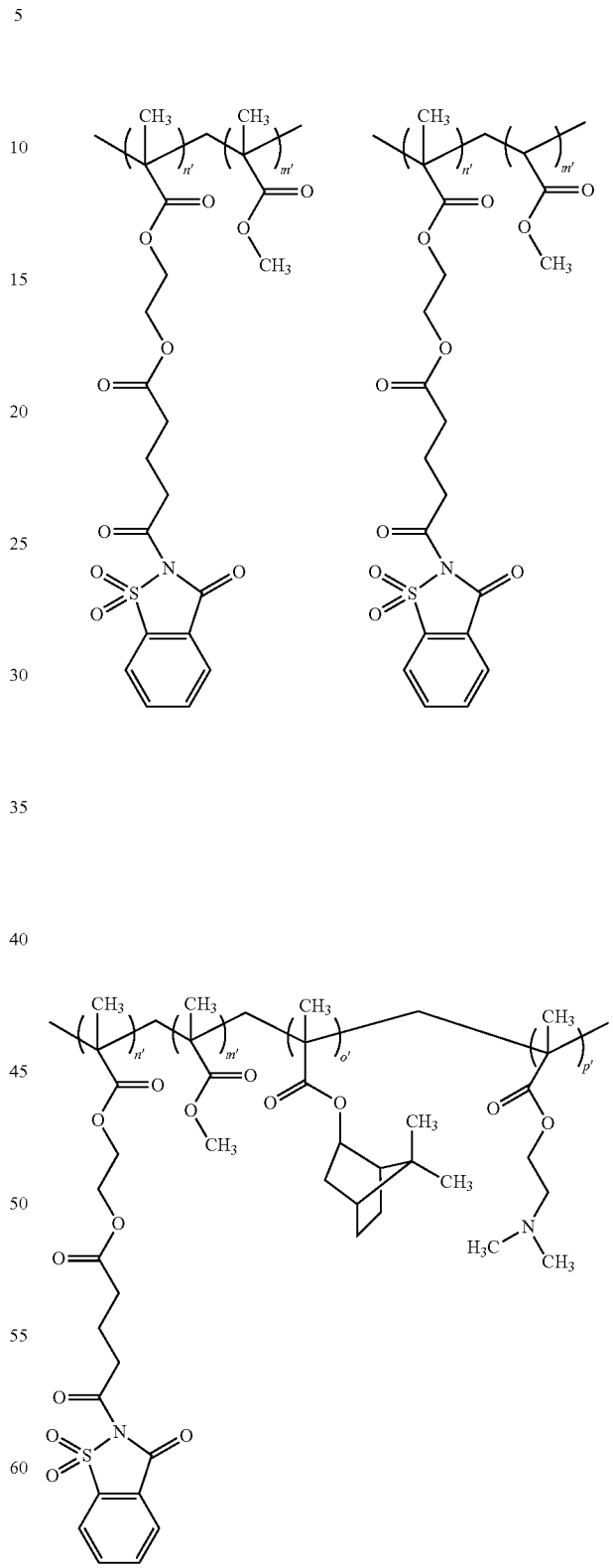

-continued

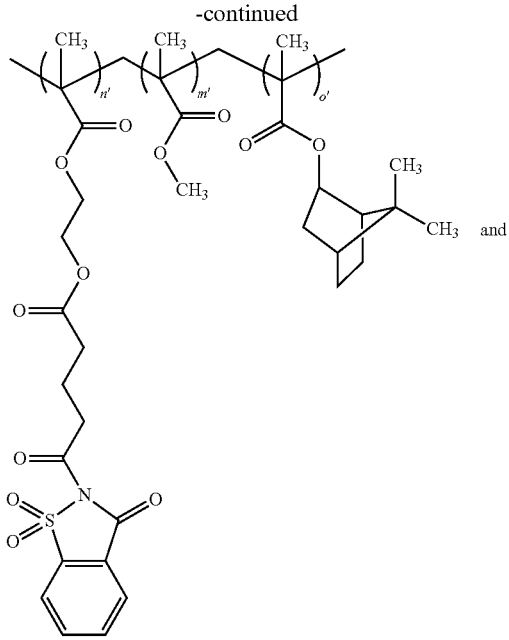

and

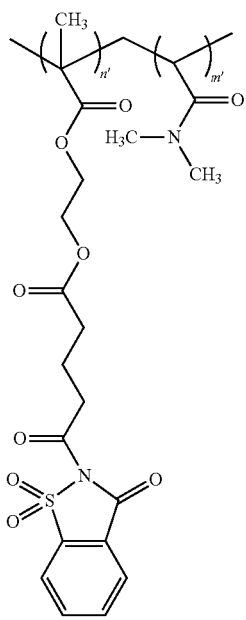

wherein m', n', o', and p' represent the number of times each moiety is present in the polymer.

19. The acoustic sensor of claim 18 wherein the soluble polymer has the formula:

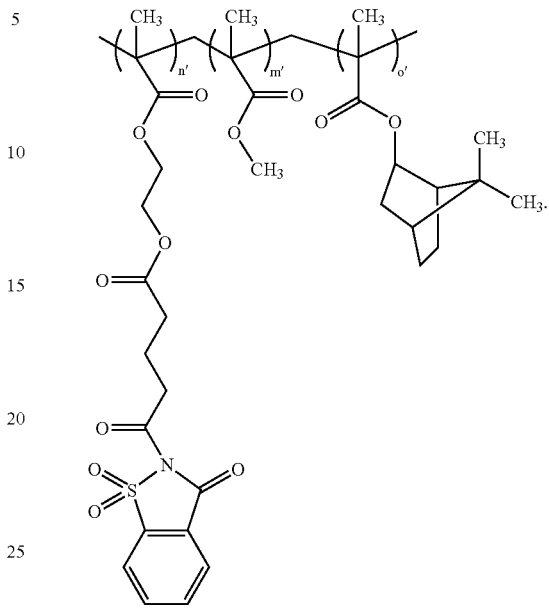

20. An acoustic sensor comprising a soluble polymer having two or more pendant groups independently selected from the group consisting of functional groups having the following formulas:

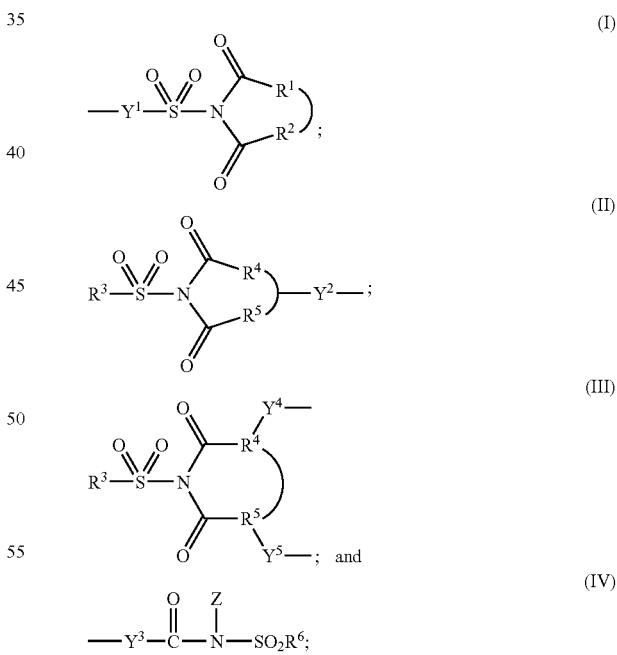

wherein:
R$^1$ and R$^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

R³ is an alkyl, aryl, aralkyl, or —NRᵃRᵇ wherein Rᵃ and Rᵇ are each an alkyl group or taken together with the nitrogen atom to which they are attached form a four to eight membered heterocyclic group;

R⁴ and R⁵ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

R⁶ is an alkyl, fluoroalkyl, chloroalkyl, aryl, —NRᶜRᵈ wherein Rᶜ and Rᵈ are each an alkyl group or taken together with the nitrogen atom to which they are attached form a four to eight membered cyclic group, or R⁶ taken together with Rᵉ and the groups to which they are attached form the four to eight membered heterocyclic or heterobicyclic group that can be fused to the optional aromatic group, optional saturated or unsaturated cyclic group, or optional saturated or unsaturated bicyclic group;

Z is an alkyl, aryl, or —(CO)Rᵉ wherein Rᵉ together with R⁶ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

Y¹, Y², and Y³ are each independently a single bond or a divalent group selected from the group consisting of an alkylene, heteroalkylene, arylene, carbonyl, carbonyloxy, carbonylimino, oxy, thio, —NRᶠ— where Rᶠ is hydrogen or alkyl, and combinations thereof; and Y⁴ and Y⁵ are each a bond.

21. The acoustic sensor of claim 20 comprising an immobilizing waveguide layer, wherein the immobilizing waveguide layer comprises the soluble polymer.

22. The acoustic sensor of claim 21 wherein the soluble polymer is a random polymer having a molecular weight of at least 1000, and is of the following formula:

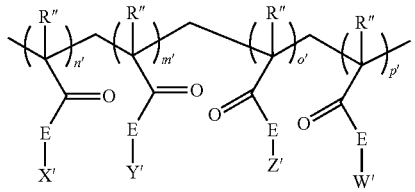

wherein:
each R″ is independently H or CH₃;
each E is —O— or —NRᶠ—, where Rᶠ is hydrogen or alkyl;
m′, n′, o′, p′ represent the number of times each moiety is present in the polymer;
X′, Y′, Z′, and W′ are independently selected from the group consisting of alkyl, aryl, hydroxy ester, alkoxyalkyl, alkoxyaryl, ether, fluoroalkyl, trialkoxysilylalkyl, and N-containing groups; and at least one of X′, Y′, Z′, or W′ includes an acylsulfonamide group of the following formula:

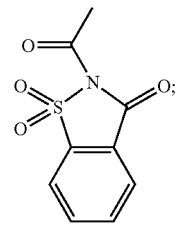

and
the polymer includes at least two distinct moieties.

23. The acoustic sensor of claim 22 wherein at least one of X′, Y′, Z′, or W′ is the following group:

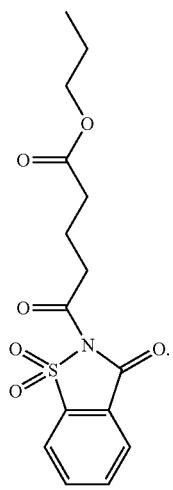

24. The acoustic sensor of claim 23 wherein the soluble polymer is selected from the group consisting of:

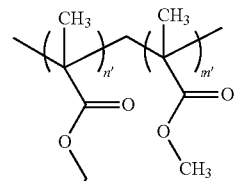
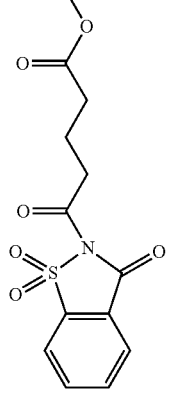

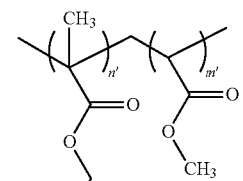
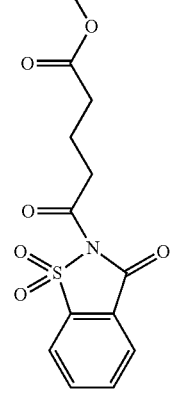

-continued

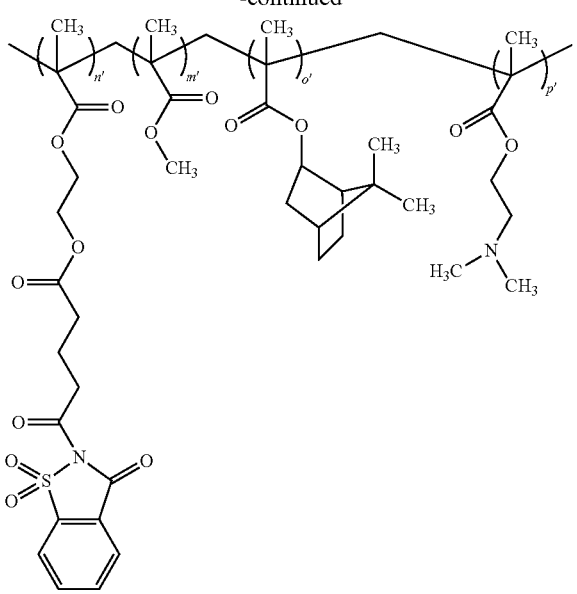

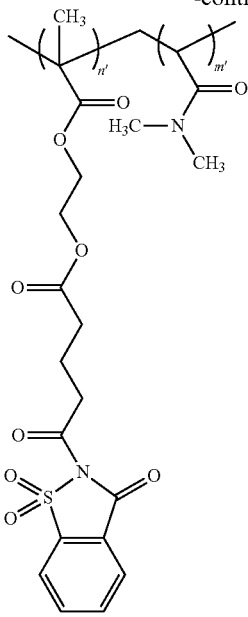

wherein m', n', o', and p' represent the number of times each moiety is present in the polymer.

25. The acoustic sensor of claim 24 wherein the soluble polymer has the formula:

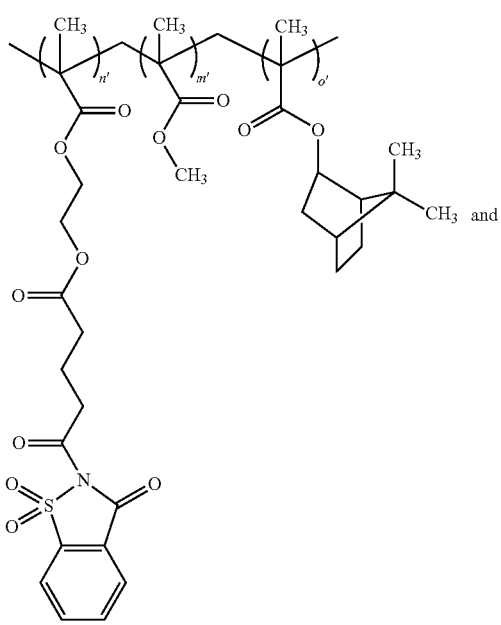

and

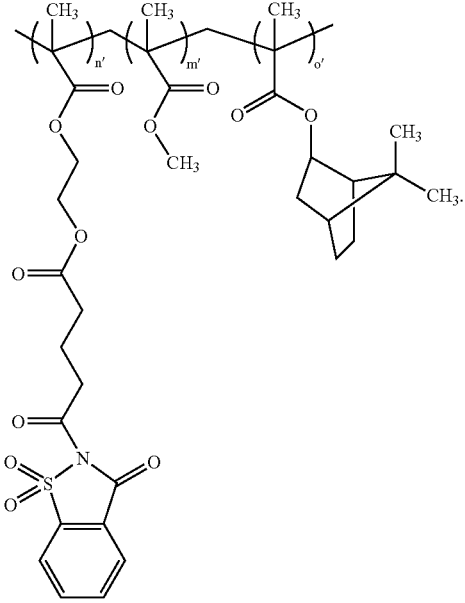

26. The acoustic sensor of claim 20 comprising a waveguide layer and an immobilization overlayer, wherein the immobilization overlayer comprises the soluble polymer.

27. The acoustic sensor of claim 26 wherein the waveguide layer comprises a polyepoxide, a polymer derived from one or more (meth)acrylate monomers, a styrene-containing polymer, a polymer derived from N-vinylcarbazole and optionally other ethylenically unsaturated monomers, a polyimide, a $VF_2$-containing fluoropolymer, or combinations thereof.

* * * * *

UNITED STATES PATENT AND TRADEMARK OFFICE
CERTIFICATE OF CORRECTION

| | | |
|---|---|---|
| PATENT NO. | : 7,943,388 B2 | |
| APPLICATION NO. | : 10/596953 | |
| DATED | : May 17, 2011 | |
| INVENTOR(S) | : John Patrick Baetzold | |

It is certified that error appears in the above-identified patent and that said Letters Patent is hereby corrected as shown below:

Title Page, Column 2 (Other Publications)
Line 5, Delete "AlChE" and insert in place thereof -- AIChE --.

Title Page, Column 2 (Abstract)
Line 3, After "soluble" insert in place thereof -- polymers, monomers (optionally --.

Title Page 2, Column 2 (Other Publications)
Line 6, Delete "2-Substitued" and insert in place thereof -- 2-Substituted --.

Column 3
Line 7, Delete "(II)," and insert in place thereof -- (III), --.

Column 5
Line 44, Delete "III," and insert in place thereof -- I, II, --.

Column 7
Lines 51-52, Delete "substitutents" and insert in place thereof -- substituents --.

Line 54, Delete "CO)—." and insert in place thereof -- —(CO)—. --.

Column 8
Line 23, Delete "—." and insert in place thereof -- —S—. --.

Line 38, Delete "substitutent" and insert in place thereof -- substituent --.

Line 40, Delete "substitutent" and insert in place thereof -- substituent --.

Column 12
Line 60, Delete "AlChE" and insert in place thereof -- AICheE --.

Signed and Sealed this
Eighth Day of May, 2012

David J. Kappos
*Director of the United States Patent and Trademark Office*

Column 14
Line 62 (Approx.), Delete "I" and insert in place thereof -- II --.

Column 16
Line 37 (Approx.), Delete "$Y^2$" and insert in place thereof -- $Y^2$, --.

Column 27
Line 39 (Approx.), Delete "RCH=CH-P+Q-A/R/G→RCH=CH-U-A/R/G" and insert in place thereof -- RCH=CH-P+Q-A/R/G→RCH=CH-U-A/R/G --.

Line 51, Before "which" insert -- allow variation of the length, hydrophilicity, and rotational freedom of the tether, all of --.

Column 37
Line 23, Delete "m," and insert in place thereof -- III, --.

Lines 25-31, Delete "Suitable (meth)acrylates,......are alkyl(meth)acrylates." and insert the same on Column 37, Line 26 as a new paragraph.

Line 34, Delete "C(R')" and insert in place thereof -- $C(R^1)$ --.

Column 38
Line 21, Delete "of" and insert in place thereof -- of: --.

Line 30 (Approx.), Delete "naphtyl," and insert in place thereof -- naphthyl --.

Column 40
Line 14, Delete "also," and insert in place thereof -- also --.

Column 50
Line 49, Delete "(2-methlbutyronitrile)," and insert in place thereof -- (2-methylbutyronitrile), --.

Column 51
Line 64, Before "washed" insert -- was --.

Column 52
Line 37, Before "washed" insert -- was --.

Column 54
Line 17 (Approx.), Delete "N11" and insert in place thereof -- MP1 --.

Column 56
Line 29, Before "washed" insert -- was --.

Column 57
Line 7, Before "washed" insert -- was --.

Line 27, Before "grams" insert -- 30 --.

Column 58
Line 48, Delete "N,N-diethyl" and insert in place thereof -- N,N-dimethyl --.

Column 59
Line 41 (Approx.), Delete "hours" and insert in place thereof -- hours. --.

Column 60
Line 51, Before "washed" insert -- was --.

Column 63
Line 42 (Approx.), Delete "Poly(MMA MeFBSEMA/A174)," and insert in place thereof -- Poly(MMA/MeFBSEMA/A174), --.

Column 64
Line 43, Delete "coated," and insert in place thereof -- coated --.

Column 67
Line 66, Before "washed" insert -- was --.

Column 70
Line 11 (Approx.), Before "washed" insert -- was --.

Column 73
Line 60, In Claim 7, delete "R'" and insert in place thereof -- R" --.

Column 77
Line 23 (Approx.), In Claim 16, delete "p'" and insert in place thereof -- and p' --.

Column 81
Line 61, In Claim 22, delete "p'" and insert in place thereof -- and p' --.